US012509443B2

(12) United States Patent
Kostik et al.

(10) Patent No.: US 12,509,443 B2
(45) Date of Patent: Dec. 30, 2025

(54) CSF-1R INHIBITORS AND METHODS OF USE THEREOF

(71) Applicant: Deciphera Pharmaceuticals, LLC, Waltham, MA (US)

(72) Inventors: Elena Kostik, Waltham, MA (US); Ann Gelormini, Waltham, MA (US); Michael D. Kaufman, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 19/299,588

(22) Filed: Aug. 14, 2025

(65) Prior Publication Data

US 2025/0368621 A1 Dec. 4, 2025

Related U.S. Application Data

(63) Continuation of application No. PCT/US2025/027042, filed on Apr. 30, 2025.

(60) Provisional application No. 63/641,028, filed on May 1, 2024.

(51) Int. Cl.
*C07D 401/14* (2006.01)
*A61K 31/444* (2006.01)

(52) U.S. Cl.
CPC .......... *C07D 401/14* (2013.01); *A61K 31/444* (2013.01)

(58) Field of Classification Search
CPC .................................................... C07D 401/14
USPC ......................................................... 514/272
See application file for complete search history.

(56) References Cited

U.S. PATENT DOCUMENTS

| | | | |
|---|---|---|---|
| 7,144,911 | B2 | 12/2006 | Flynn et al. |
| 7,202,257 | B2 | 4/2007 | Flynn et al. |
| 7,279,576 | B2 | 10/2007 | Flynn et al. |
| 7,342,037 | B2 | 3/2008 | Flynn et al. |
| 7,531,566 | B2 | 5/2009 | Flynn et al. |
| 7,666,895 | B2 | 2/2010 | Flynn et al. |
| 7,737,283 | B2 | 6/2010 | Flynn et al. |
| 7,790,756 | B2 | 9/2010 | Flynn et al. |
| 7,897,762 | B2 | 3/2011 | Flynn et al. |
| 8,143,293 | B2 | 3/2012 | Flynn et al. |
| 8,163,756 | B2 | 4/2012 | Flynn et al. |
| 8,188,113 | B2 | 5/2012 | Flynn et al. |
| 8,278,331 | B2 | 10/2012 | Flynn et al. |
| 8,461,179 | B1 | 6/2013 | Flynn et al. |
| 8,486,951 | B2 | 7/2013 | Flynn et al. |
| 8,569,319 | B2 | 10/2013 | Flynn et al. |
| 8,586,565 | B2 | 11/2013 | Flynn et al. |
| 8,637,672 | B2 | 1/2014 | Flynn et al. |
| 8,741,911 | B2 | 6/2014 | Allgeier et al. |
| 8,921,565 | B2 | 12/2014 | Flynn et al. |
| 8,940,756 | B2 | 1/2015 | Flynn et al. |
| 9,012,635 | B2 | 4/2015 | Flynn et al. |
| 9,133,183 | B2 | 9/2015 | Flynn et al. |
| 9,181,223 | B2 | 11/2015 | Kaufman et al. |
| 9,187,474 | B2 | 11/2015 | Flynn et al. |
| 9,193,719 | B2 | 11/2015 | Flynn et al. |
| 9,309,224 | B2 | 4/2016 | Flynn et al. |
| 9,334,267 | B2 | 5/2016 | Flynn et al. |
| 9,382,228 | B2 | 7/2016 | Flynn et al. |
| 9,387,202 | B2 | 7/2016 | Flynn et al. |
| 9,457,019 | B2 | 10/2016 | Flynn et al. |
| 11,103,507 | B2 | 8/2021 | Flynn et al. |
| 11,679,110 | B2 | 6/2023 | Flynn et al. |
| 12,285,430 | B2 | 4/2025 | Flynn et al. |
| 2008/0214544 | A1 | 9/2008 | Bellon et al. |
| 2008/0255155 | A1 | 10/2008 | Raeppel et al. |
| 2010/0120806 | A1 | 5/2010 | Flynn et al. |
| 2010/0166699 | A1 | 7/2010 | Thompson et al. |
| 2011/0053906 | A1 | 3/2011 | Huck et al. |
| 2014/0145025 | A1 | 5/2014 | Fang et al. |
| 2015/0073129 | A1 | 3/2015 | Herting et al. |
| 2019/0091217 | A1 | 3/2019 | Flynn et al. |
| 2020/0129489 | A1 | 4/2020 | Flynn et al. |
| 2020/0352920 | A1 | 11/2020 | Flynn et al. |
| 2020/0354346 | A1 | 11/2020 | Flynn et al. |
| 2020/0354352 | A1 | 11/2020 | Flynn et al. |

(Continued)

FOREIGN PATENT DOCUMENTS

| | | | |
|---|---|---|---|
| CN | 105120864 | A | 12/2015 |
| CN | 105473617 | A | 4/2016 |
| CN | 113880812 | A | 1/2022 |

(Continued)

OTHER PUBLICATIONS

U.S. Appl. No. 11/450,850, filed Jun. 9, 2006, Expired, US 2008-0299639 A1.

(Continued)

*Primary Examiner* — Taofiq A Solola
(74) *Attorney, Agent, or Firm* — Goodwin Procter LLP

(57) ABSTRACT

Provided herein, in part, is a compound of Formula (I)

(I)

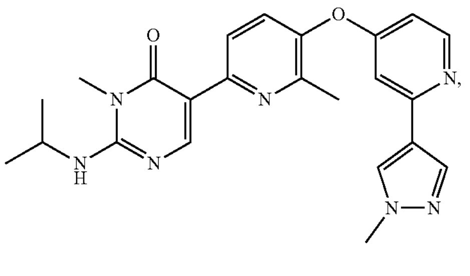

or a hydrate thereof, essentially free of one or more impurities, compositions thereof, and methods of use thereof.

21 Claims, 2 Drawing Sheets

(56) References Cited

U.S. PATENT DOCUMENTS

| | | | |
|---|---|---|---|
| 2021/0015801 A1 | 1/2021 | Flynn et al. |
| 2023/0414614 A1 | 12/2023 | Flynn et al. |

FOREIGN PATENT DOCUMENTS

| | | | |
|---|---|---|---|
| CN | 116283919 A | 6/2023 |
| EP | 3632907 A1 | 4/2020 |
| EP | 3682881 A1 | 7/2020 |
| JP | 6364472 B2 | 7/2018 |
| RU | 2330024 C2 | 7/2008 |
| WO | WO-2003/000660 A1 | 1/2003 |
| WO | WO-2008/079291 A2 | 7/2008 |
| WO | WO-2010051373 | 5/2010 |
| WO | WO-2014145015 | 9/2014 |
| WO | WO-2014145025 | 9/2014 |
| WO | WO-2014145028 | 9/2014 |
| WO | WO-2020139828 A1 | 7/2020 |
| WO | WO-2022247786 A1 | 12/2022 |

OTHER PUBLICATIONS

U.S. Appl. No. 11/963,740, filed Dec. 21, 2007, Granted, U.S. Pat. No. 8,163,756.
U.S. Appl. No. 12/829,561, filed Jul. 2, 2010, Granted, U.S. Pat. No. 8,586,565.
U.S. Appl. No. 11/870,388, filed Oct. 10, 2007, Granted, U.S. Pat. No. 7,790,756.
U.S. Appl. No. 11/854,354, filed Sep. 12, 2007, Granted, U.S. Pat. No. 8,188,113.
U.S. Appl. No. 12/105,408, filed Apr. 18, 2008, Expired, US 2008-0261965 A1.
U.S. Appl. No. 13/590,955, filed Aug. 21, 2012, Expired, US 2013-0079362 A1.
U.S. Appl. No. 13/559,170, filed Jul. 26, 2012, Expired, US 2012-0322834 A1.
U.S. Appl. No. 14/214,134, filed Mar. 14, 2014, Granted, U.S. Pat. No. 9,133,183.
U.S. Appl. No. 13/785,575, filed Mar. 5, 2013, Published, US 2013-0252977 A1.
U.S. Appl. No. 14/383,803, filed Mar. 5, 2013, Granted, U.S. Pat. No. 9,187,474.
U.S. Appl. No. 13/491,394, filed Jun. 7, 2012, Granted, U.S. Pat. No. 8,461,179.
U.S. Appl. No. 13/801,753, filed Mar. 13, 2013, Granted, U.S. Pat. No. 8,940,756.
U.S. Appl. No. 16/387,315, filed Apr. 17, 2019, Granted, U.S. Pat. No. Re. 48,731.
U.S. Appl. No. 14/214,160, filed Mar. 14, 2014, Granted, U.S. Pat. No. 9,193,719.
U.S. Appl. No. 14/214,171, filed Mar. 14, 2014, Granted, U.S. Pat. No. 9,181,223.
U.S. Appl. No. 14/214,185, filed Mar. 14, 2014, Granted, U.S. Pat. No. 9,382,228.
U.S. Appl. No. 14/214,179, filed Mar. 14, 2014, Granted, U.S. Pat. No. 9,309,224.
U.S. Appl. No. 14/535,900, filed Nov. 7, 2014, Granted, U.S. Pat. No. 9,457,019.
U.S. Appl. No. 17/845,275, filed Jun. 21, 2022, Published, US 2022-0370423 A1.
U.S. Appl. No. 17/845,278, filed Jun. 21, 2022, Pending, US 2022-0370424 A1.
U.S. Appl. No. 16/943,821, filed Jul. 30, 2020, Granted, U.S. Pat. No. 11,986,463.
U.S. Appl. No. 18/631,891, filed Apr. 10, 2024, Published, US 2024-0415818 A1.
U.S. Appl. No. 16/943,871, filed Jul. 30, 2020, Granted, U.S. Pat. No. 12,102,620.
U.S. Appl. No. 18/815,054, filed Aug. 26, 2024, Pending, US 2025-0090506 A1.
U.S. Appl. No. 16/725,282, filed Dec. 23, 2019, Granted, U.S. Pat. No. 11,103,507.
U.S. Appl. No. 17/358,137, filed Jun. 25, 2021, Granted, U.S. Pat. No. 11,679,110.
U.S. Appl. No. 18/140,942, filed Apr. 28, 2023, Granted, U.S. Pat. No. 12,285,430.
U.S. Appl. No. 19/079,727, filed Mar. 14, 2025, Allowed, US 2025-0205237 A1.
U.S. Appl. No. 16/870,384, filed May 8, 2020, Granted, U.S. Pat. No. 11,530,206.
U.S. Appl. No. 17/833,272, filed Jun. 6, 2022, Granted, U.S. Pat. No. 12,071,432.
U.S. Appl. No. 18/770,318, filed Jul. 11, 2024, Published, US 2025-0084073 A1.
U.S. Appl. No. 16/870,418, filed May 8, 2020, Granted, U.S. Pat. No. 11,518,758.
U.S. Appl. No. 17/832,224, filed Jun. 3, 2022, Allowed, US 2023-0047915 A1.
U.S. Appl. No. 16/902,989, filed Jun. 16, 2020, Granted, U.S. Pat. No. 11,590,134.
U.S. Appl. No. 18/152,993, filed Jan. 11, 2023, Granted, U.S. Pat. No. 12,377,097.
U.S. Appl. No. 19/235,263, filed Jun. 11, 2025, Pending.
U.S. Appl. No. 16/991,644, filed Aug. 12, 2020, Published, US 2023-0277522 A1.
U.S. Appl. No. 17/180,234, filed Feb. 19, 2021, Granted, U.S. Pat. No. 11,185,535.
U.S. Appl. No. 17/504,133, filed Oct. 18, 2021, Granted, U.S. Pat. No. 11,576,903.
U.S. Appl. No. 18/314,348, filed May 9, 2023, Granted, U.S. Pat. No. 11,801,237.
U.S. Appl. No. 18/463,498, filed Sep. 8, 2023, Published, US 2024-0197696 A1.
U.S. Appl. No. 17/028,640, filed Sep. 22, 2020, Granted, U.S. Pat. No. 10,966,966.
U.S. Appl. No. 17/180,218, filed Feb. 19, 2021, Granted, U.S. Pat. No. 11,266,635.
U.S. Appl. No. 17/583,977, filed Jan. 25, 2022, Granted, U.S. Pat. No. 11,426,390.
U.S. Appl. No. 17/583,985, filed Jan. 25, 2022, Granted, U.S. Pat. No. 11,344,536.
U.S. Appl. No. 17/727,307, filed Apr. 22, 2022, Granted, U.S. Pat. No. 11,534,432.
U.S. Appl. No. 17/735,678, filed May 3, 2022, Granted, U.S. Pat. No. 11,529,336.
U.S. Appl. No. 17/735,682, filed May 3, 2022, Granted, U.S. Pat. No. 11,576,904.
U.S. Appl. No. 17/735,862, filed May 3, 2022, Granted, U.S. Pat. No. 11,433,056.
U.S. Appl. No. 17/869,108, filed Jul. 20, 2022, Granted, U.S. Pat. No. 11,969,414.
U.S. Appl. No. 18/091,743, filed Dec. 30, 2022, Granted, U.S. Pat. No. 11,813,251.
U.S. Appl. No. 18/500,549, filed Nov. 2, 2023, Granted, U.S. Pat. No. 12,059,410.
U.S. Appl. No. 18/500,650, filed Nov. 2, 2023, Granted, U.S. Pat. No. 12,023,325.
U.S. Appl. No. 18/500,730, filed Nov. 2, 2023, Granted, U.S. Pat. No. 12,023,327.
U.S. Appl. No. 18/500,792, filed Nov. 2, 2023, Granted, U.S. Pat. No. 12,059,411.
U.S. Appl. No. 18/500,686, filed Nov. 2, 2023, Granted, U.S. Pat. No. 12,023,326.
U.S. Appl. No. 18/750,014, filed Jun. 21, 2024, Granted, U.S. Pat. No. 12,295,944.
U.S. Appl. No. 18/750,032, filed Jun. 21, 2024, Granted, U.S. Pat. No. 12,318,373.
U.S. Appl. No. 19/194,583, filed Apr. 30, 2025, Pending.
U.S. Appl. No. 17/180,241, filed Feb. 19, 2021, Granted, U.S. Pat. No. 11,395,818.
U.S. Appl. No. 17/735,820, filed May 3, 2022, Granted, U.S. Pat. No. 11,612,591.

(56) References Cited

OTHER PUBLICATIONS

U.S. Appl. No. 18/148,766, filed Dec. 30, 2022, Granted, U.S. Pat. No. 11,896,585.
U.S. Appl. No. 18/178,789, filed Mar. 6, 2023, Granted, U.S. Pat. No. 11,793,795.
U.S. Appl. No. 18/448,309, filed Aug. 11, 2023, Granted, U.S. Pat. No. 11,850,240.
U.S. Appl. No. 18/448,312, filed Aug. 11, 2023, Granted, U.S. Pat. No. 11,903,933.
U.S. Appl. No. 18/448,347, filed Aug. 11, 2023, Granted, U.S. Pat. No. 11,844,788.
U.S. Appl. No. 18/448,333, filed Aug. 11, 2023, Granted, U.S. Pat. No. 11,850,241.
U.S. Appl. No. 18/518,093, filed Nov. 22, 2023, Granted, U.S. Pat. No. 12,064,422.
U.S. Appl. No. 18/490,188, filed Oct. 19, 2023, Granted, U.S. Pat. No. 11,911,370.
U.S. Appl. No. 18/490,197, filed Oct. 19, 2023, Granted, U.S. Pat. No. 11,918,564.
U.S. Appl. No. 18/518,100, filed Nov. 22, 2023, Granted, U.S. Pat. No. 11,969,415.
U.S. Appl. No. 18/518,110, filed Nov. 22, 2023, Granted, U.S. Pat. No. 12,023,328.
U.S. Appl. No. 18/758,007, filed Jun. 28, 2024, Granted, U.S. Pat. No. 12,318,374.
U.S. Appl. No. 18/795,711, filed Aug. 6, 2024, Granted, U.S. Pat. No. 12,226,406.
U.S. Appl. No. 18/795,683, filed Aug. 6, 2024, Granted, U.S. Pat. No. 12,213,967.
U.S. Appl. No. 18/795,731, filed Aug. 6, 2024, Granted, U.S. Pat. No. 12,213,968.
U.S. Appl. No. 19/085,149, filed Mar. 20, 2025, Pending.
U.S. Appl. No. 17/528,478, filed Nov. 17, 2021, Granted, U.S. Pat. No. 11,912,668.
U.S. Appl. No. 18/408,956, filed Jan. 10, 2024, Published, US 2024-0376058 A1.
U.S. Appl. No. 18/512,447, filed Nov. 17, 2023, Pending.
U.S. Appl. No. 17/534,795, filed Nov. 24, 2021, Allowed, US 2022-0193083 A1.
U.S. Appl. No. 17/534,768, filed Nov. 24, 2021, Granted, U.S. Pat. No. 11,801,238.
U.S. Appl. No. 18/073,886, filed Dec. 2, 2022, Published, US 2023-0382915 A1.
U.S. Appl. No. 18/505,396, filed Nov. 9, 2023, Published, US 2024-0122906 A1.
U.S. Appl. No. 18/683,078, filed Feb. 12, 2024, Published, US 2025-0127790 A1.
U.S. Appl. No. 18/078,269, filed Dec. 9, 2022, Published, US 2023-0357179 A1.
U.S. Appl. No. 18/078,271, filed Dec. 9, 2022, Granted, U.S. Pat. No. 12,319,655.
U.S. Appl. No. 19/001,282, filed Dec. 24, 2024, Published, US 2025-0250235 A1.
U.S. Appl. No. 18/073,721, filed Dec. 2, 2022, Published, US 2024-0116877 A1.
U.S. Appl. No. 18/456,831, filed Aug. 28, 2023, Published, US 2024-0150368 A1.
U.S. Appl. No. 17/938,353, filed Oct. 6, 2022, Granted, U.S. Pat. No. 11,779,572.
U.S. Appl. No. 18/464,519, filed Sep. 11, 2023, Published, US 2024-0261270 A1.
U.S. Appl. No. 18/389,888, filed Dec. 20, 2023, Published, US 2024-0245660 A1.
U.S. Appl. No. 18/985,885, filed Dec. 18, 2024, Published, US 2025-0206729 A1.
U.S. Appl. No. 15/999,530, filed Aug. 17, 2018, Granted, U.S. Pat. No. 11,077,113.
U.S. Appl. No. 17/362,763, filed Jun. 29, 2021, Granted, U.S. Pat. No. 11,633,403.
U.S. Appl. No. 18/181,046, filed Mar. 9, 2023, Published, US 2024-0050439 A1.
U.S. Appl. No. 15/999,432, filed Aug. 17, 2018, Granted, U.S. Pat. No. 11,179,399.
U.S. Appl. No. 17/501,407, filed Oct. 14, 2021, Published, US 2022-0175788 A1.
U.S. Appl. No. 16/638,727, filed Feb. 12, 2020, Granted, U.S. Pat. No. 11,498,919.
U.S. Appl. No. 18/045,605, filed Oct. 11, 2022, Published, US 2023-0322772 A1.
U.S. Appl. No. 16/639,895, filed Feb. 18, 2020, Granted, U.S. Pat. No. 11,219,618.
U.S. Appl. No. 17/644,486, filed Dec. 15, 2021, Published, US 2022-0218688 A1.
U.S. Appl. No. 16/639,900, filed Feb. 18, 2020, Granted, U.S. Pat. No. 11,208,423.
U.S. Appl. No. 17/530,119, filed Nov. 18, 2021, Granted, U.S. Pat. No. 11,780,858.
U.S. Appl. No. 18/457,682, filed Aug. 29, 2023, Pending.
U.S. Appl. No. 16/639,902, filed Feb. 18, 2020, Granted, U.S. Pat. No. 11,560,374.
U.S. Appl. No. 18/084,208, filed Dec. 19, 2022, Published, US 2023-0234949 A1.
U.S. Appl. No. 18/457,825, filed Aug. 29, 2023, Published, US 2024-0180923 A1.
U.S. Appl. No. 18/980,378, filed Dec. 13, 2024, Published, US 2025-0236609 A1.
U.S. Appl. No. 18/971,800, filed Dec. 6, 2024, Published, US 2025-0206720 A1.
U.S. Appl. No. 19/079,010, filed Mar. 13, 2025, Pending, US 2025-0243182 A1.
U.S. Appl. No. 18/971,846, filed Dec. 6, 2024, Published, US 2025-0205161 A1.
U.S. Appl. No. 19/079,070, filed Mar. 13, 2025, Published, US 2025-0205236 A1.
U.S. Appl. No. 19/295,254, filed Aug. 8, 2025, Pending.
U.S. Appl. No. 19/299,605, filed Aug. 14, 2025, Pending.
U.S. Appl. No. 19/079,965, filed Mar. 14, 2025, Pending.
U.S. Appl. No. 18/980,426, filed Dec. 13, 2024, Published, US 2025-0195487 A1.
U.S. Appl. No. 17/437,552, filed Sep. 9, 2021, Published, US 2022-0144825 A1.
"Deciphera Pharmaceuticals Announces Positive, Preliminary, Top-Line Clinical Data for the Ongoing Phase 1 Clincial Study with DCC-3014 and an Update on Future Development Plans," 2019, 1-3.
"History of Changes for Study: NCT03069469 Study of DCC-3014 in Patients with Advanced Malignancies," ClinicalTrials.gov Archive, 2018, 1-5.
Al-Muhsen et al., "The Expression of Stem Cell Factor and c-Kit Receptor in Human Asthmatic Airways," Clinical and Experimental Allergy, 2004, 34: 911-917.
Attoub et al., "The C-Kit Tyrosine Kinase Inhibitor STI571 for Colorectal Cancer Therapy," Cancer Research, 2002, 62: 4879-4883.
Blay, JY et al., "P63: Patient-Reported Outcomes Following Treatment with Vimseltinib for Tenosynovial Giant Cell Tumour in a Phase 2 Expansion Study", Value in Health, Elsevier, Amsterdam, NL, vol. 25, No. 12 (Dec. 1, 2022), XP087229982.
Boisson et al., "c-Kit and c-kit mutations in mastocytosis and other hematological diseases," Journal of Leukocyte Biology, 2000, 67(2):135-148.
Brinkmann et al., "Fingolimod (FTY720): Discovery and Development of an Oral Drug to Treat Multiple Sclerosis," Nature Reviews | Drug Discovery, 2010, 9: 883-897.
Brunton et al., "Chemotherapy of Neoplastic Diseases," in, Goodman and Gilman's: The Pharmacological Basis of Therapeutics, 2008, 11th ed.: 853-908.
Burns et al., "C-FMS Inhibitors: A Patent Review," Expert Opinion on Therapeutic Patents, 2011, 147-165.
Caira M. R. et al. "Crystalline Polymorphism of Organic Compounds", Design of Organic Solids. Topics in Current Chemistry, vol. 198, p. 163-208 (1998).

(56) References Cited

OTHER PUBLICATIONS

Caldwell, T. M. et al., "Discovery of vimseltinib (DCC-3014), a highly selective CSF1R switch-control kinase inhibitor, in clinical development for the treatment of Tenosynovial Giant Cell Tumor (TGCT)," Biorg. Med. Chem. Lett. 74, (2022) 128928, 7 pages.
Carvajal et al., "KIT as a Therapeutic Target in Metastatic Melanoma," Journal of the American Medical Association, 2011, 305(22): 2327-2334.
Dewar et al., "Inhibition of c-fms by Imatinib: expanding the spectrum of treatment," Cell Cycle, 2005, 4(7):851-853.
Dewar et al., "Macrophage Colony-Stimulating Factor Receptor C-Fms is a Novel Target of Imatinib," Blood, 2005, 105(8): 3127-3132.
Di Lorenzo et al., "Expression of Proto-Oncogene C-Kit in High Risk Prostate Cancer," European Journal of Surgical Oncology, 2004, 30: 987-992.
Dorwald, "Side Reactions in Organic Synthesis," Wiley: VCH Weinhem Preface, 2005, 1-15 & 8: 279-308.
El Agamy et al., "Targeting c-Kit in the Therapy of Mast Cell Disorders: Current Update," European Journal of Pharmacology, 2012, 690: 1-3.
Fang Z. et al. Conformational restriction: an effective tactic in 'follow-on'-based drug discovery, Fugure Med Chem. 2014, 6(8): 885-901.
Fine et al., "Neoplasms of the Central Nervous System," Cancer Principles & Practice of Oncology, 2005, 1834-1887.
Fogarty et al., "Development of Protein Kinase Activators: AMPK as a Target in Metabolic Disorders and Cancer," Biochimica et Biophysica Acta, 2010, 1804: 581-591.
Gelderblom, H. et al., "475P: Safety and Efficacy of Vimseltinib in Tenosynovial Giant Cell Tumour (TGCT)): Long-term Phase I Update", Annals of Oncology, vol. 33, (Sep. 1, 2022), p. S757, XP093241096.
Gelderblom, H. et al., "Vimseltinib versus placebo for tenosynovial giant cell tumour (Motion): a multicentre, randomised, double-blind, placebo-controlled, phase 3 trial", The Lancet, vol. 403, No. 10445, (Jun. 3, 2024), pp. 2709-2719, XP093241015.
Girouard et al., "Neurovascular Coupling in the Normal Brain and in Hypertension, Stroke, and Alzheimer Disease," J. Appl Physiol., 2006, 100: 328-335.
Gupta et al., "IL-3 Inhibits Human Osteoclastogenesis and Bone Resorption through Downregulation of c-Fms and Diverts the Cells to Dendritic Cell Lineage," The Journal of Immunology, 2010, 2261-2272.
Heinrich et al., "Inhibition of c-kit receptor tyrosine kinase activity by STI 571, a selective tyrosine kinase inhibitor," Blood, 2000, 96(3):925-932.
Henriksen et al., "Assessment of Osteoclast Number and Function: Application in the Development of New and Improved Treatment Modalities for Bone Diseases," Osteoporosis International, 2006, 18: 681-685.
International Search Report and Written Opinion for International Patent Application No. PCT/US2014/029661 mailed Jun. 11, 2014.
International Search Report and Written Opinion for International Patent Application No. PCT/US2014/029664 mailed Jun. 11, 2014.
International Search Report and Written Opinion for International Patent Application No. PCT/US2024/053261 mailed Feb. 6, 2025.
Judge et al., "Potassium Channel Blockers in Multiple Sclerosis: Neuronal Kv Channels and Effects of Symptomatic Treatment," Pharmacology & Therapeutics, 2006, 224-259.
Khadka, P. et al., Pharmaceutical particle technologies: An approach to improve drug solubility, dissolution and bioavailability, Asian Journal of Pharmaceutical Sciences, 9(6): 304-316 (2014).
Kumari A. et al. 3D-QSAR analysis of anilinoquinoline inhibitors of colony stimulating factor-1 kinase(cFMS): implementation of field-based molecular alignment, Med Chem Res 22, 5167-5183 (2013).
Kung et al., "Structure Activity Relationships of Quinoline-Containing c-Met Inhibitors," European Journal of Medicinal Chemistry 43, 2008, 1321-1329.
Kuster et al., "Kinase Inhibitors Methods and Protocols," Methods in Molecular Biology, 2012, 1-46.
Lewitt, "Levodopa for the Treatment of Parkinson's Disease," New England Journal of Medicine, 2008, 359: 2468-2476.
Luo et al., "Principles of Cancer Therapy: Oncogene and Non-oncogene Addiction," Cell, 2009, 36: 823-837.
Minkin, "Bone Acid Phosphatase: Tartrate-Resistant Acid Phosphatase as a Marker of Osteoclast Function," Calcified Tissue International, 1982, 34: 285-290.
Mitchell et al., "Amyotrophic Lateral Sclerosis," The Lancet, 2007, 369: 2031-2041.
National Cancer Institute (http://www.cancer.gov) 2014.
O'Brien et al., "Vascular Cognitive Impairment," The Lancet Neurology, 2003, 2: 89-98.
Ohno et al., "A c-fms tyrosine kinase inhibitor, Ki20227, suppresses osteoclast differentiation and osteolytic bone destruction in a bone metastasis model," Mol Cancer Ther., 2006, 5(11):2634-2643.
PCT/US2019/068311 International Search Report and Written Opinion mailed Jul. 2, 2020.
PCT/US2024/058988 International Search Report and Written Opinion dated Mar. 24, 2025.
PCT/US2024/058998 International Search Report and Written Opinion mailed Jun. 2, 2025, 11 pages.
PCT/US2024/060067 International Search Report and Written Opinion mailed Apr. 10, 2025, 48 pages.
PCT/US2025/027042 International Search Report and Written Opinion mailed Jul. 23, 2025, 12 pages.
Pyonteck et al., "CSF-1R inhibition alters macrophage polarization and blocks glioma progression," Nature Medicine, 2013, 19(10):1264-1274.
Reber et al., "Stem Cell Factor and its Receptor c-Kit as Targets for Inflammatory Diseases," European Journal of Pharmacology, 2006, 533: 327-340.
Roberts et al., "Antiangiogenic and Antitumor Activity of a Selective PDGFR Tyrosine Kinase Inhibitor, CP-673, 451," Cancer Research, 2005, 957-966.
Rubin et al., "KIT activation is a ubiquitous feature of gastrointestinal stromal tumors," Cancer Research, 2001, 61(22):8118-8121.
Shah et al., "Current Approaches in the Treatment of Alzheimer's Disease," Biomedicine & Pharmacotherapy, 2008, 62: 199-207.
Silverman R.B. et al. Lead Discovery, The Organic Chemistry of Drug Design and Drug Action, 3rd Ed, Chapter 2, pp. 19-122, Elsevier (2014).
Smith, B. D. et al., "Vimseltinib: A Precision CSF1R Therapy for Tenosynovial Giant Cell Tumors and Diseases Promoted by Macrophages", Molecular Cancer Therapeutics, vol. 20, No. 11, (Aug. 25, 2021), pp. 2098-2109, XP093171464.
Tap et al., "Pexidartinib Versus Placebo for Advanced Tenosynovial Giant Cell Tumour (Enliven): a Randomised Phase 3 Trial, " Lancet, 2019, 394: 478-487.
Tap et al., "Structure-Guided Blockade of CSF1R Kinase in Tenosynovial Giant-Cell Tumor," New England Journal of Medicine, 2015, 373(5):428-437.
Tap, W. D. et al., "Efficacy, safety, and patient-reported outcomes of vimseltinib in patients with tenosynovial giant cell tumor: Results from the phase 3 Motion trial", Journal of Clinical Oncology, vol. 42, No. 16_suppl, (Jun. 1, 2024), pp. 11500-11500, XP093241007.
Tap, W. D. et al., "Motion: A randomized, phase 3, placebo-controlled, double-blind study of vimseltinib (DCC-3014) for the treatment of tenosynovial giant cell tumour", Journal of Clinical Oncology, vol. 40, No. 16_suppl., (Jun. 2, 2022), pp. TPS11590-TPS11590, XP093241022.
Wen et al., "Osteosarcoma Cell-Intrinsic Colony Stimulating Factor-1 Receptor Functions to Promote Tumor Cell Metastasis Through JAG1 Signaling," American Journal of Cancer Research, 2017, 7(4): 801-815.
Yasuda et al., "The Stem Cell Factor/C-Kit Receptor Pathway Enhance Proliferation and Invasion of Pancreatic Cancer Cells," Molecular Cancer, 2006, 5(46): 1-10.

CSF-1R INHIBITORS AND METHODS OF USE THEREOF

CROSS-REFERENCE

This application is a continuation of International Application Number PCT/US2025/027042 filed Apr. 30, 2025, which claims priority to U.S. Provisional Application No. 63/641,028 filed May 1, 2024, the contents of which are incorporated herein by reference.

The present disclosure relates to high purity compound represented by Formula (I), or a hydrate thereof, compositions comprising said compound represented by Formula (I), or a hydrate thereof, and methods of use thereof.

BACKGROUND

Colony-stimulating factor 1 receptor (CSF-1R) and its ligand, colony stimulating factor 1 (CSF-1) together form a lineage dependency for normal macrophage development and differentiation from monocytes. As such, tumor-associated macrophages (TAMs) are dependent on CSF-1R (also known as FMS) kinase activity for proliferation, and maintenance of their differentiated state and immunosuppressive phenotype. The role of TAMs in promoting an invasive and immunosuppressive tumor microenvironment is well established. TAMs mediate tumor growth, angiogenesis, invasiveness, metastasis, and immunosuppression through the secretion of and response to a variety of cytokines or other soluble factors. TAMs are educated by tumors to enable escape from immune surveillance by dampening a cytotoxic T cell immune response, thereby shielding the tumor from T cell eradication. For example, TAMs express PD-L1, a known immunosuppressive checkpoint that induces T cell anergy.

Several inhibitors targeting CSF-1R have advanced into the clinic as direct antitumor therapies and potential immunotherapies. Many of these drugs also inhibit the closely related Type III receptor tyrosine kinases KIT, PDGFRα/β and FLT3, which may limit their utility due to off-target toxicity. Antibodies targeting CSF-1R are much more specific yet result in >10,000-fold increases in plasma levels of CSF-1, the ligand for CSF-1R, due to blockade of CSF-1 clearance, among other drawbacks.

Tenosynovial giant cell tumor (TGCT) is a proliferative and inflammatory disease that includes entities formerly known as pigmented villonodular synovitis (PVNS), and giant cell tumor of the tendon sheath (GCTTS), intraarticular or extraarticular. It is a rare neoplasm of the joint or tendon sheath, with destructive proliferation of synovial like mononuclear cells, admixed with multinucleate giant cells, foam cells, siderophages and inflammatory cells. There are two types of TGCT: the local or nodular form (where the tumor involves the tendons that support the joint, or in one area of the joint) and the diffuse form (where the entire lining of the joint is involved). Treatment is surgical excision of the tumor. However, it is often difficult to perform a marginal excision for the diffuse form of TGCT resulting in a high recurrence rate. It can be characterized by overexpression of CSF-1.

Thus, there is a need for selective small-molecule CSF-1R inhibitors that are useful in the treatment of disorders associated with the proliferation of TAMs including solid tumors of various cancers and treatment of mesenchymal tumors including TGCT and diffuse-type tenosynovial giant cell tumor (DTGCT).

Certain impurities may be incompatible with other substances in a composition when formulated into pharmaceutical compositions comprising the active pharmaceutical ingredient and a pharmaceutically acceptable carrier; reduce shelf life of the composition; cause difficulties during formulation and use of the composition; cause physical and chemical instabilities of the compositions; lower therapeutic effects of the composition; show adverse biological effects such as genotoxicity; or change the odor, color, or taste of the composition. Therefore, there is a need for a highly pure active pharmaceutical ingredient. Provided herein, in some embodiments, is a highly pure compound represented by Formula (I), compositions, and methods of use thereof.

SUMMARY

Described herein, in part, is a compound of Formula (I)

(I)

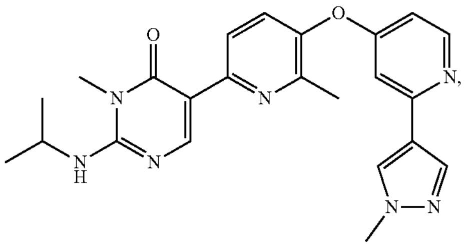

or a hydrate thereof, essentially free of one or more impurities.

Provided herein, in some embodiments, is a compound of Formula (I)

(I)

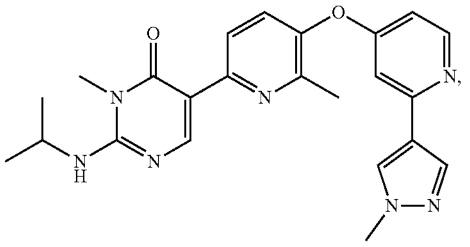

or a hydrate thereof, essentially free of a compound of Formula (II)

(II)

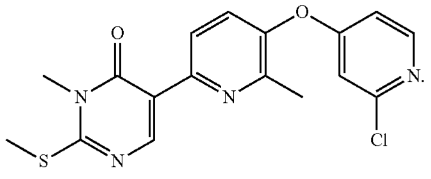

Provided herein, in some embodiments, is a compound of Formula (I)

(I)

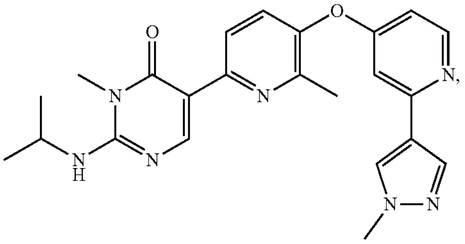

or a hydrate thereof,
with no more than about 50 ppm to about 1000 ppm of a compound of Formula (II)

(II)

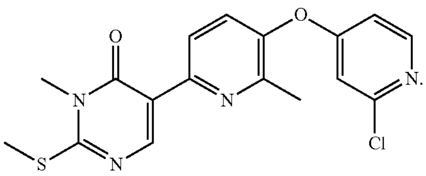

Provided herein, in some embodiments, is a compound of Formula (I)

(I)

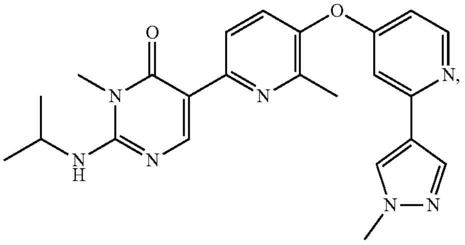

or a hydrate thereof,
with no more than about 1% to about 5% by weight/weight of one or more impurities.

Provided herein, in some embodiments, is a compound of Formula (I)

(I)

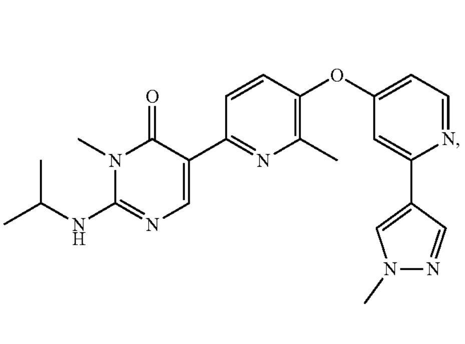

or a hydrate thereof,
that is substantially free of one or more impurities.

In some embodiments, provided herein are pharmaceutical compositions comprising a compound of Formula (I), or a hydrate thereof, and a pharmaceutically acceptable carrier.

Provided herein, in part, are methods of treating diseases and conditions including, but not limited to a tenosynovial giant cell tumor (TGCT) including diffuse-type tenosynovial giant cell tumor (DTGCT) and localized tenosynovial giant cell tumor. Provided herein, in part, are methods of treating diseases and conditions including, but not limited to graft versus host disease (GVHD) including chronic graft versus host disease (cGVHD) and acute graft versus host disease (aGVHD). Provided herein, in part, are methods of treating diseases and conditions including, but not limited to a neurodegenerative diseases or conditions including Parkinson's disease (PD), Alzheimer's Disease (AD), frontotemporal dementia (FTD), amyotrophic lateral sclerosis (ALS), mild cognitive impairment, and Huntington's Disease (HD). Provided herein, in part, are methods of treating diseases and conditions including, but not limited to, solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, wherein solid tumors include, but are not limited to, ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumors. Provided herein, in part, are methods of treating diseases and conditions including, but not limited to tumors known to have expression of colony-stimulating factor 1 receptor (CSF-1R) or its ligands, colony stimulating factor-1 (CSF-1), or interleukin (IL)-34 (IL-34). Provided herein, in part, are methods of treating diseases and conditions including, but not limited to metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis. Provided herein, in part, are methods of treating diseases and conditions using the compound represented by Formula (I), or a hydrate thereof, and pharmaceutical compositions and/or pharmaceutical formulations thereof.

DETAILED DESCRIPTION

Figure 1:
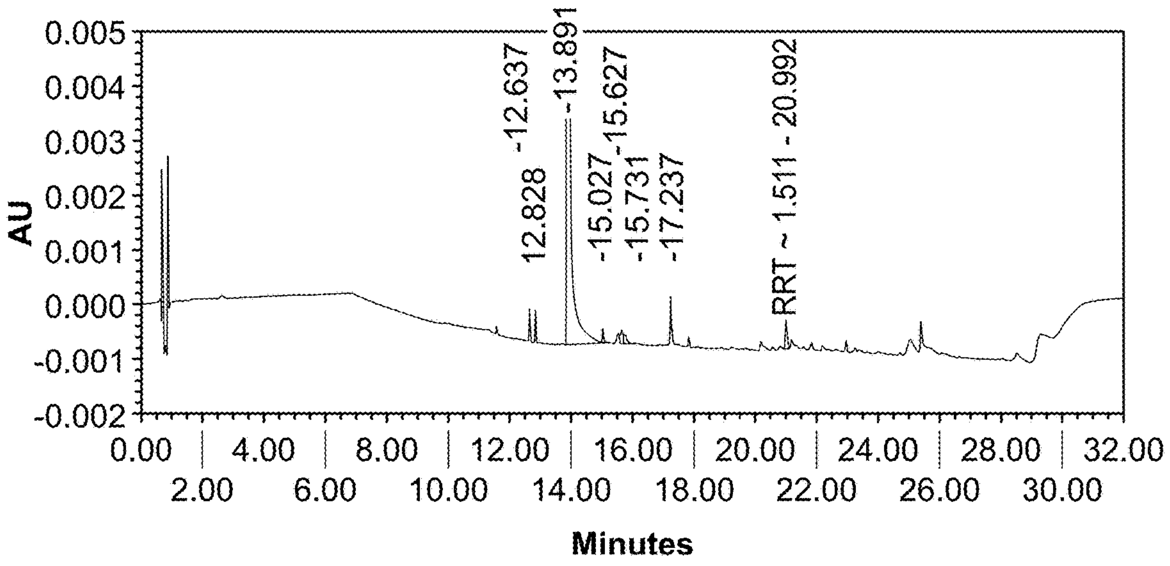
FIG. 1 shows an ultra-high-performance liquid chromatography (UHPLC) chromatogram of an exemplary batch of a dihydrate of the compound of Formula (I).

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

Terms used in the singular will also include the plural. For example, "a" means one or more unless indicated otherwise.

The compound represented by Formula (I) as described herein is also referred to as "vimseltinib." The compound represented by Formula (I) as described herein also refers to 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one.

As used herein, the crystalline dihydrate form of the compound represented by Formula (I) is

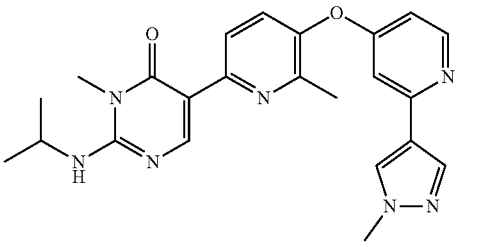

•2 $H_2O$.

The crystalline dihydrate form of the compound represented by Formula (I) is also referred to herein as "vimseltinib dihydrate."

All ranges recited herein include the endpoints, including those that recite a range "between" two values. The terms "substantially" and "about" are to be construed as modifying a term or value such that it is not an absolute. This includes, at very least, the degree of expected experimental variance, experimental error, technique variance, technique error and instrument variance, instrumental error for a given technique used to measure a value.

As used herein, "about" includes and describes the value or parameter per se. For example, "about x" includes and describes "x" per se. In some embodiments, the term "about" when used in association with a measurement, or used to modify a value, a unit, a constant, or a range of values, refers to variations of ±10%.

As used herein, the term "adding" does not limit the order, method or how the materials being added are combined, unless indicated otherwise. For instance, "adding X to Y" may also describe "adding Y to X." Furthermore, "adding X and Y to Z" may also describe the various other combinations such as "adding X to Y and Z," "adding X and Z to Y," "adding Y to X and Z," "adding Y and Z to X," and "adding Z to X and Y."

As used herein, the term "excipient" refers to a substance that may be beneficial to include in a composition with an active agent. The term "excipient" includes inert substances as well as functional excipients that may result in beneficial properties of the composition. Exemplary excipients include but are not limited to polymers, glidants, sugars, lubricants, salts, buffers, fats, fillers, disintegrating agents, binders, surfactants, high surface area substrates, flavorants, carriers, matrix materials, diluents, and so forth.

As used herein, the terms "individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

As used herein, the terms "pharmaceutically acceptable" or "pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards as required by FDA standards.

As used herein, the term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

As used herein, the term "pharmaceutical composition" as used herein refers to a composition comprising at least one compound as disclosed herein Formulated together with one or more pharmaceutically acceptable carriers, excipients or diluents.

As used herein, the term "pharmaceutically acceptable salt(s)" refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, the term "therapeutically effective amount" means the amount of the subject compound that will elicit the biological or medical response of a tissue, system or animal, (e.g., mammal or human) that is being sought by the researcher, veterinarian, medical doctor or other clinician. A compound described herein, e.g., the compound represented by Formula (I), is administered in therapeutically effective amounts to treat a condition, e.g., TGCT, GVHD, or neurodegenerative diseases. Alternatively, a therapeutically effective amount of a compound is the quantity required to achieve a desired therapeutic and/or prophylactic effect, such as an amount which results in the prevention of or a decrease in the symptoms associated with the condition.

As used herein and unless otherwise indicated, the terms "treat," "treating" and "treatment" refer to the alleviation of a disease or disorder and/or at least one of its attendant symptoms, and includes any effect, e.g., lessening, reducing, modulating, or eliminating, that results in the improvement of the condition, disease, disorder and the like.

As used herein and unless otherwise indicated, the terms “prevent,” “preventing” and “prevention” refer to the inhibition of a symptom of a disease or disorder or the disease itself.

As used herein, the term “active agent” means a drug, medicament, pharmaceutical, therapeutic agent, for example, the compound represented by Formula (I), as described herein.

As used herein, the term “oral formulation,” refers to a composition or medium used to administer a compound as disclosed herein (e.g., the compound represented by Formula (I)) to a subject in need thereof by oral administration. Typically, an oral formulation is administered via the mouth, however, “oral formulation” as used herein is intended to cover any substance which is administered to a subject and is absorbed across a membrane, e.g., a mucosal membrane, of the gastrointestinal tract, including, e.g., the mouth, esophagus, stomach, small intestine, large intestine, and colon. In one embodiment, the oral formulation is a solid oral formulation. In one embodiment, the oral formulation is a solid oral formulation administered to a subject in need thereof via the mouth.

A reaction mixture may be characterized herein as being at or allowed to come to “room temperature” or “ambient temperature,” often abbreviated as “RT” or “rt.” This means that the temperature of the thing is close to, or the same as, that of the space, e.g., the room or fume hood, in which the thing is located. In some embodiments, room temperature is about 20° C. to about 30° C. In some embodiments, room temperature is about 22° C. to about 27° C. In some embodiments, room temperature is about 25° C.

The amount of solvent employed in a chemical process, e.g., a reaction, may be referred to herein as a number of “volumes” or “vol” or “V.” In this context, this expression would be understood to mean milliliters of the solvent per gram of the material being suspended or dissolved. For example, a material may be referred to as being suspended or dissolved in 10 volumes (or 10 vol or 10V) of a solvent, such that suspending or dissolving 5 grams of a material in 10 volumes of a solvent means that the solvent is used in an amount of 10 milliliters (mL) per gram of the material that is being suspended or, in this example, 50 mL of the solvent. In another context, the term “v/v” may be used to indicate the number of volumes of a solvent that are added to a liquid mixture based on the volume of that mixture. For example, adding solvent X (1.5 v/v) to a 100 mL reaction mixture would indicate that 150 mL of solvent X was added.

A process or step may be referred to herein as being carried out “overnight.” This refers to a time interval, e.g., for the process or step, that spans the time during the night, when that process or step may not be actively observed. In some embodiments, “overnight” is about 8 hours to about 24 hours. In some embodiments, “overnight” is about 10 hours to about 18 hours. In some embodiments, “overnight” is about 16 hours.

As used herein, the term “reduced pressure” refers to a pressure that is less than atmospheric pressure, i.e., less than about 1013 millibars (1013 mbar). In some embodiments, a reduced pressure is about 10 mbar to about 50 mbar. In some embodiments, a reduced pressure is about 30 mbar to about 50 mbar.

As used herein, “essentially free” (e.g., as measured by a weight/weight %) refers to a compound (e.g., a compound of Formula (I), or a hydrate thereof) that contains about 10% or less, about 9% or less, about 8% or less, about 7% or less, about 6% or less, about 5% or less, about 4% or less, about 3% or less, about 2% or less, about 1% or less, about 0.5% or less, of one or more impurities. In some embodiments, essentially free refers to a compound (e.g., a compound of Formula (I), or a hydrate thereof) that contains an undetectable amount of one or more impurities.

As used herein and unless otherwise indicated, the term “substantially pure” when used to describe a compound (e.g., a compound of Formula (I), or a hydrate thereof) means said compound that is substantially free of other compounds such as impurities. A representative substantially pure compound comprises greater than about 80% by weight of said compound and less than about 20% by weight of other compounds such as impurities. In some embodiments, a representative substantially pure compound comprises greater than about 90% by weight of said compound and less than about 10% by weight of other compounds such as impurities. In some embodiments, a representative substantially pure compound comprises greater than about 95% by weight of said compound and less than about 5% by weight of other compounds such as impurities. In some embodiments, a representative substantially pure compound comprises greater than about 96% by weight of said compound and less than about 4% by weight of other compounds such as impurities. In some embodiments, a representative substantially pure compound comprises greater than about 97% by weight of said compound and less than about 3% by weight of other compounds such as impurities. In some embodiments, a representative substantially pure compound comprises greater than about 98% by weight of said compound and less than about 2% by weight of other compounds such as impurities. In some embodiments, a representative substantially pure compound comprises greater than about 99% by weight of said compound and less than about 1% by weight of other compounds such as impurities. The term “substantially pure” may also be measured in terms of other parameters, such as by % area under the curve by HPLC. A representative substantially pure compound comprises greater than about 80% area under the curve as measured by HPLC of said compound and less than about 20% area under the curve as measured by HPLC of other compounds such as impurities. In some embodiments, a representative substantially pure compound comprises greater than about 90% area under the curve as measured by HPLC of said compound and less than about 10% area under the curve as measured by HPLC of other compounds such as impurities. In some embodiments, a representative substantially pure compound comprises greater than about 95% area under the curve as measured by HPLC of said compound and less than about 5% area under the curve as measured by HPLC of other compounds such as impurities. In some embodiments, a representative substantially pure compound comprises greater than about 96% area under the curve as measured by HPLC of said compound and less than about 4% area under the curve as measured by HPLC of other compounds such as impurities. In some embodiments, a representative substantially pure compound comprises greater than about 97% area under the curve as measured by HPLC of said compound and less than about 3% area under the curve as measured by HPLC of other compounds such as impurities. In some embodiments, a representative substantially pure compound comprises greater than about 98% area under the curve as measured by HPLC of said compound and less than about 2% area under the curve as measured by HPLC of other compounds such as impurities. In some embodiments, a representative substantially pure compound comprises greater than about 99% area under the curve as measured by HPLC of said compound and less than about 1% area under the curve as measured by HPLC of other compounds such as impurities. In some embodiments, a representative substantially pure compound comprises greater than about 99.5% area under the curve as measured by HPLC of said compound and less than about 0.5% area under the curve as measured by HPLC of other compounds such as impurities. In some embodiments, a representative substantially pure compound comprises un undetectable amount as measured by HPLC of other compounds such as impurities. HPLC purity is based on a calculation of the area under a peak divided by the total area under the curve in an HPLC chromatogram.

As used herein, "AUC" refers to the area under the curve of a peak in liquid chromatography analysis disclosed herein. In some embodiments, the liquid chromatography analysis is a high performance liquid chromatography (HPLC) analysis. In some embodiments, the liquid chromatography analysis is an ultra-high performance liquid chromatography (UHPLC) analysis.

As used herein, "area %" or "% area under the curve" refers to the percentage of area under the curve (AUC) of a peak with respect to the total area under the curve of all peaks in a liquid chromatography analysis disclosed herein. The area % or % area under the curve of a peak in a liquid chromatography analysis disclosed herein is a measure of the amount of a compound with respect to the total amount of compounds present in the sample being analyzed. In some embodiments, the liquid chromatography analysis is a high performance liquid chromatography (HPLC) analysis. In some embodiments, the liquid chromatography analysis is an ultra-high-performance liquid chromatography (UHPLC) analysis.

As used herein, "TAM" refers to tumor-associated macrophage.

As used herein, "TGCT" refers to tenosynovial giant cell tumor.

As used herein, "DTGCT" refers to diffuse or diffuse-type tenosynovial giant cell tumor.

As used herein, "GCTTS" refers to giant cell tumor of the tendon sheath.

As used herein, "PVNS" refers to pigmented villonodular synovitis.

As used herein, "GVHD" refers to graft versus host disease.

As used herein, "AD" refers to Alzheimer's Disease.

As used herein, "PD" refers to Parkinson's Disease.

As used herein, "HD" refers to Huntington's Disease.

As used herein, "FTD" refers to frontotemporal dementia.

As used herein, "ALS" refers to amyotrophic lateral sclerosis.

Compounds

Provided herein in some embodiments is a compound of Formula (I)

(I)

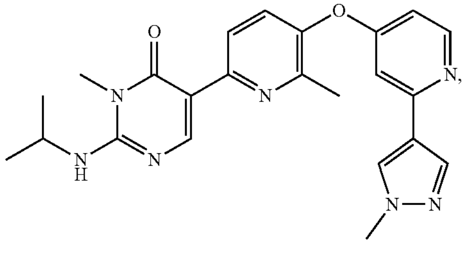

or a hydrate thereof, essentially free of one or more impurities.

Provided herein, in some embodiments, is a compound of Formula (I)

(I)

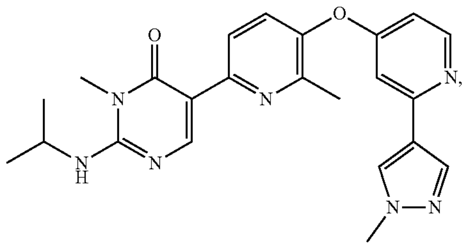

or a hydrate thereof, essentially free of a compound of Formula (II)

(II)

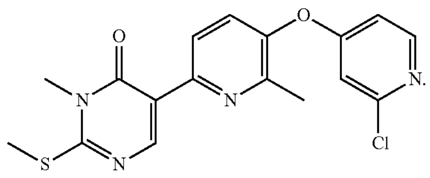

Provided herein, in some embodiments, is a compound of Formula (I)

(I)

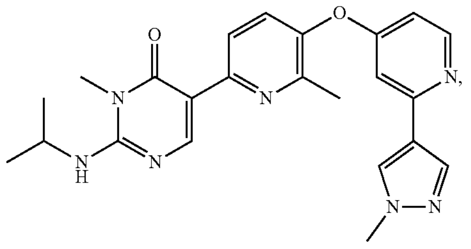

or a hydrate thereof, which is substantially pure.

Provided herein, in some embodiments, is a compound of Formula (I)

(I)

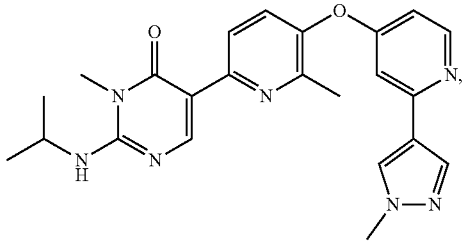

or a hydrate thereof, with no more than about 50 ppm to about 1000 ppm of a compound of Formula (II)

(II)

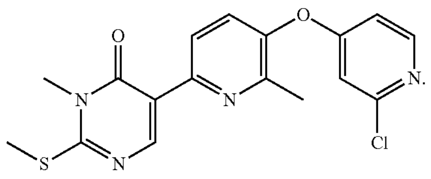

In some embodiments, the compound of Formula (I), or a hydrate thereof, comprises no more than about 100 ppm to about 900 ppm of the compound of Formula (II). In some embodiments, the compound of Formula (I), or a hydrate thereof, comprises no more than about 100 ppm to about 800 ppm of the compound of Formula (II). In some embodiments, the compound of Formula (I), or a hydrate thereof, comprises no more than about 100 ppm to about 700 ppm of the compound of Formula (II). In some embodiments, the compound of Formula (I), or a hydrate thereof, comprises no more than about 100 ppm to about 600 ppm of the compound of Formula (II). In some embodiments, the compound of Formula (I), or a hydrate thereof, comprises no more than about 100 ppm to about 500 ppm of the compound of Formula (II). In some embodiments, the compound of Formula (I), or a hydrate thereof, comprises no more than about 150 ppm to about 500 ppm of the compound of Formula (II). In some embodiments, the compound of Formula (I), or a hydrate thereof, comprises no more than about 150 ppm to about 400 ppm of the compound of Formula (II). In some embodiments, the compound of Formula (I), or a hydrate thereof, comprises no more than about 150 ppm to about 300 ppm of the compound of Formula (II). In some embodiments, the compound of Formula (I), or a hydrate thereof, comprises no more than about 5 ppm, 10 ppm, 15 ppm, 20 ppm, 25 ppm, 30 ppm, 35 ppm, 40 ppm, 45 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 210 ppm, 220 ppm, 230 ppm, 240 ppm, 250 ppm, 260 ppm, 270 ppm, 280 ppm, 290 ppm, 300 ppm, 310 ppm, 320 ppm, 330 ppm, 340 ppm, 350 ppm, 360 ppm, 370 ppm, 380 ppm, 390 ppm, 400 ppm, 410 ppm, 420 ppm, 430 ppm, 440 ppm, 450 ppm, 460 ppm, 470 ppm, 480 ppm, 490 ppm, or 500 ppm of the compound of Formula (II). In some embodiments, the compound of Formula (I), or a hydrate thereof, comprises no more than about 1000 ppm of the compound of Formula (II). In some embodiments, the compound of Formula (I), or a hydrate thereof, comprises no more than about 900 ppm of the compound of Formula (II). In some embodiments, the compound of Formula (I), or a hydrate thereof, comprises no more than about 800 ppm of the compound of Formula (II). In some embodiments, the compound of Formula (I), or a hydrate thereof, comprises no more than about 700 ppm of the compound of Formula (II). In some embodiments, the compound of Formula (I), or a hydrate thereof, comprises no more than about 600 ppm of the compound of Formula (II). In some embodiments, the compound of Formula (I), or a hydrate thereof, comprises no more than about 500 ppm of the compound of Formula (II). In some embodiments, the compound of Formula (I), or a hydrate thereof, comprises no more than about 450 ppm of the compound of Formula (II). In some embodiments, the compound of Formula (I), or a hydrate thereof, comprises no more than about 400 ppm of the compound of Formula (II). In some embodiments, the compound of Formula (I), or a hydrate thereof, comprises no more than about 350 ppm of the compound of Formula (II). In some embodiments, the compound of Formula (I), or a hydrate thereof, comprises no more than about 300 ppm of the compound of Formula (II). In some embodiments, the compound of Formula (I), or a hydrate thereof, comprises no more than about 250 ppm of the compound of Formula (II). In some embodiments, the compound of Formula (I), or a hydrate thereof, comprises no more than about 200 ppm of the compound of Formula (II). In some embodiments, the compound of Formula (I), or a hydrate thereof, comprises no more than about 150 ppm of the compound of Formula (II). In some embodiments, the compound of Formula (I), or a hydrate thereof, comprises no more than about 100 ppm of the compound of Formula (II). In some embodiments, the compound of Formula (I), or a hydrate thereof, comprises no more than about 90 ppm of the compound of Formula (II). In some embodiments, the compound of Formula (I), or a hydrate thereof, comprises no more than about 80 ppm of the compound of Formula (II). In some embodiments, the compound of Formula (I), or a hydrate thereof, comprises no more than about 70 ppm of the compound of Formula (II). In some embodiments, the compound of Formula (I), or a hydrate thereof, comprises no more than about 60 ppm of the compound of Formula (II). In some embodiments, the compound of Formula (I), or a hydrate thereof, comprises no more than about 50 ppm of the compound of Formula (II). In some embodiments, the compound of Formula (I), or a hydrate thereof, comprises no more than about 45 ppm of the compound of Formula (II). In some embodiments, the compound of Formula (I), or a hydrate thereof, comprises no more than about 40 ppm of the compound of Formula (II). In some embodiments, the compound of Formula (I), or a hydrate thereof, comprises no more than about 35 ppm of the compound of Formula (II). In some embodiments, the compound of Formula (I), or a hydrate thereof, comprises no more than about 30 ppm of the compound of Formula (II). In some embodiments, the compound of Formula (I), or a hydrate thereof, comprises no more than about 25 ppm of the compound of Formula (II). In some embodiments, the compound of Formula (I), or a hydrate thereof, comprises no more than about 20 ppm of the compound of Formula (II). In some embodiments, the compound of Formula (I), or a hydrate thereof, comprises no more than about 15 ppm of the compound of Formula (II). In some embodiments, the compound of Formula (I), or a hydrate thereof, comprises no more than about 10 ppm of the compound of Formula (II). In some embodiments, the compound of Formula (I), or a hydrate thereof, comprises no more than about 5 ppm of the compound of Formula (II). In some embodiments, the compound of Formula (I), or a hydrate thereof, comprises an undetectable amount of the compound of Formula (II).

Provided herein, in some embodiments, are compositions comprising a compound of Formula (I)

(I)

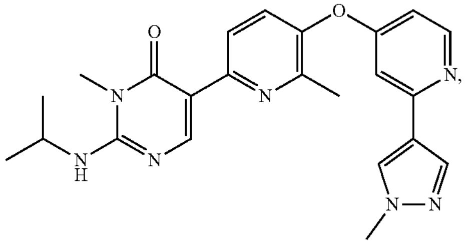

or a hydrate thereof, having a purity of greater than or equal to about 95% weight/weight of the composition, and a compound of Formula (II), wherein the compound of Formula (II) is present in the composition at no more than about 300 ppm.

In some embodiments, the compound of Formula (I), or a hydrate thereof, is characterized by a purity of greater than or equal to about 96% weight/weight of the composition. In some embodiments, the compound of Formula (I), or a hydrate thereof, is characterized by a purity of greater than or equal to about 97% weight/weight of the composition. In some embodiments, the compound of Formula (I), or a hydrate thereof, is characterized by a purity of greater than or equal to about 98% weight/weight of the composition. In some embodiments, the compound of Formula (I), or a hydrate thereof, is characterized by a purity of greater than or equal to about 99% weight/weight of the composition.

In some embodiments, the composition comprises no more than about 100 ppm to about 900 ppm of the compound of Formula (II). In some embodiments, the composition comprises no more than about 100 ppm to about 800 ppm of the compound of Formula (II). In some embodiments, the composition comprises no more than about 100 ppm to about 700 ppm of the compound of Formula (II). In some embodiments, the composition comprises no more than about 100 ppm to about 600 ppm of the compound of Formula (II). In some embodiments, the composition comprises no more than about 100 ppm to about 500 ppm of the compound of Formula (II). In some embodiments, the composition comprises no more than about 150 ppm to about 500 ppm of the compound of Formula (II). In some embodiments, the composition comprises no more than about 150 ppm to about 400 ppm of the compound of Formula (II). In some embodiments, the composition comprises no more than about 150 ppm to about 300 ppm of the compound of Formula (II). In some embodiments, the composition comprises no more than about 5 ppm, 10 ppm, 15 ppm, 20 ppm, 25 ppm, 30 ppm, 35 ppm, 40 ppm, 45 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 210 ppm, 220 ppm, 230 ppm, 240 ppm, 250 ppm, 260 ppm, 270 ppm, 280 ppm, 290 ppm, 300 ppm, 310 ppm, 320 ppm, 330 ppm, 340 ppm, 350 ppm, 360 ppm, 370 ppm, 380 ppm, 390 ppm, 400 ppm, 410 ppm, 420 ppm, 430 ppm, 440 ppm, 450 ppm, 460 ppm, 470 ppm, 480 ppm, 490 ppm, or 500 ppm of the compound of Formula (II). In some embodiments, the composition comprises no more than about 1000 ppm of the compound of Formula (II). In some embodiments, the composition comprises no more than about 900 ppm of the compound of Formula (II). In some embodiments, the composition comprises no more than about 800 ppm of the compound of Formula (II). In some embodiments, the composition comprises no more than about 700 ppm of the compound of Formula (II). In some embodiments, the composition comprises no more than about 600 ppm of the compound of Formula (II). In some embodiments, the composition comprises no more than about 500 ppm of the compound of Formula (II). In some embodiments, the composition comprises no more than about 450 ppm of the compound of Formula (II). In some embodiments, the composition comprises no more than about 400 ppm of the compound of Formula (II). In some embodiments, the composition comprises no more than about 350 ppm of the compound of Formula (II). In some embodiments, the composition comprises no more than about 300 ppm of the compound of Formula (II). In some embodiments, the composition comprises no more than about 250 ppm of the compound of Formula (II). In some embodiments, the composition comprises no more than about 200 ppm of the compound of Formula (II). In some embodiments, the composition comprises no more than about 150 ppm of the compound of Formula (II). In some embodiments, the composition comprises no more than about 100 ppm of the compound of Formula (II). In some embodiments, the composition comprises no more than about 90 ppm of the compound of Formula (II). In some embodiments, the composition comprises no more than about 80 ppm of the compound of Formula (II). In some embodiments, the composition comprises no more than about 70 ppm of the compound of Formula (II). In some embodiments, the composition comprises no more than about 60 ppm of the compound of Formula (II). In some embodiments, the composition comprises no more than about 50 ppm of the compound of Formula (II). In some embodiments, the composition comprises no more than about 45 ppm of the compound of Formula (II). In some embodiments, the composition comprises no more than about 40 ppm of the compound of Formula (II). In some embodiments, the composition comprises no more than about 35 ppm of the compound of Formula (II). In some embodiments, the composition comprises no more than about 30 ppm of the compound of Formula (II). In some embodiments, the composition comprises no more than about 25 ppm of the compound of Formula (II). In some embodiments, the composition comprises no more than about 20 ppm of the compound of Formula (II). In some embodiments, the composition comprises no more than about 15 ppm of the compound of Formula (II). In some embodiments, the composition comprises no more than about 10 ppm of the compound of Formula (II). In some embodiments, the composition comprises no more than about 5 ppm of the compound of Formula (II). In some embodiments, the composition comprises an undetectable amount of the compound of Formula (II).

Provided herein, in some embodiments, are compositions consisting essentially of a compound of Formula (I)

(I)

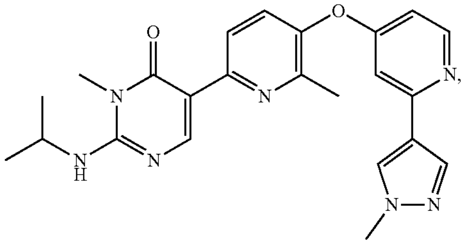

or a hydrate thereof, having a purity of greater than or equal to about 95% weight/weight of the composition, and a compound of Formula (II), wherein the compound of Formula (II) is present in the composition at no more than about 300 ppm.

In some embodiments, the compound of Formula (I), or a hydrate thereof, is characterized by a purity of greater than or equal to about 96% weight/weight of the composition. In some embodiments, the compound of Formula (I), or a hydrate thereof, is characterized by a purity of greater than or equal to about 97% weight/weight of the composition. In some embodiments, the compound of Formula (I), or a hydrate thereof, is characterized by a purity of greater than or equal to about 98% weight/weight of the composition. In some embodiments, the compound of Formula (I), or a hydrate thereof, is characterized by a purity of greater than or equal to about 99% weight/weight of the composition.

In some embodiments, the composition comprises no more than about 100 ppm to about 900 ppm of the compound of Formula (II). In some embodiments, the composition comprises no more than about 100 ppm to about 800 ppm of the compound of Formula (II). In some embodiments, the composition comprises no more than about 100 ppm to about 700 ppm of the compound of Formula (II). In some embodiments, the composition comprises no more than about 100 ppm to about 600 ppm of the compound of Formula (II). In some embodiments, the composition comprises no more than about 100 ppm to about 500 ppm of the compound of Formula (II). In some embodiments, the composition comprises no more than about 150 ppm to about 500 ppm of the compound of Formula (II). In some embodiments, the composition comprises no more than about 150 ppm to about 400 ppm of the compound of Formula (II). In some embodiments, the composition comprises no more than about 150 ppm to about 300 ppm of the compound of Formula (II). In some embodiments, the composition comprises no more than about 5 ppm, 10 ppm, 15 ppm, 20 ppm, 25 ppm, 30 ppm, 35 ppm, 40 ppm, 45 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 210 ppm, 220 ppm, 230 ppm, 240 ppm, 250 ppm, 260 ppm, 270 ppm, 280 ppm, 290 ppm, 300 ppm, 310 ppm, 320 ppm, 330 ppm, 340 ppm, 350 ppm, 360 ppm, 370 ppm, 380 ppm, 390 ppm, 400 ppm, 410 ppm, 420 ppm, 430 ppm, 440 ppm, 450 ppm, 460 ppm, 470 ppm, 480 ppm, 490 ppm, or 500 ppm of the compound of Formula (II). In some embodiments, the composition comprises no more than about 1000 ppm of the compound of Formula (II). In some embodiments, the composition comprises no more than about 900 ppm of the compound of Formula (II). In some embodiments, the composition comprises no more than about 800 ppm of the compound of Formula (II). In some embodiments, the composition comprises no more than about 700 ppm of the compound of Formula (II). In some embodiments, the composition comprises no more than about 600 ppm of the compound of Formula (II). In some embodiments, the composition comprises no more than about 500 ppm of the compound of Formula (II). In some embodiments, the composition comprises no more than about 450 ppm of the compound of Formula (II). In some embodiments, the composition comprises no more than about 400 ppm of the compound of Formula (II). In some embodiments, the composition comprises no more than about 350 ppm of the compound of Formula (II). In some embodiments, the composition comprises no more than about 300 ppm of the compound of Formula (II). In some embodiments, the composition comprises no more than about 250 ppm of the compound of Formula (II). In some embodiments, the composition comprises no more than about 200 ppm of the compound of Formula (II). In some embodiments, the composition comprises no more than about 150 ppm of the compound of Formula (II). In some embodiments, the composition comprises no more than about 100 ppm of the compound of Formula (II). In some embodiments, the composition comprises no more than about 90 ppm of the compound of Formula (II). In some embodiments, the composition comprises no more than about 80 ppm of the compound of Formula (II). In some embodiments, the composition comprises no more than about 70 ppm of the compound of Formula (II). In some embodiments, the composition comprises no more than about 60 ppm of the compound of Formula (II). In some embodiments, the composition comprises no more than about 50 ppm of the compound of Formula (II). In some embodiments, the composition comprises no more than about 40 ppm of the compound of Formula (II). In some embodiments, the composition comprises no more than about 40 ppm of the compound of Formula (II). In some embodiments, the composition comprises no more than about 35 ppm of the compound of Formula (II). In some embodiments, the composition comprises no more than about 30 ppm of the compound of Formula (II). In some embodiments, the composition comprises no more than about 25 ppm of the compound of Formula (II). In some embodiments, the composition comprises no more than about 20 ppm of the compound of Formula (II). In some embodiments, the composition comprises no more than about 15 ppm of the compound of Formula (II). In some embodiments, the composition comprises no more than about 10 ppm of the compound of Formula (II). In some embodiments, the composition comprises no more than about 5 ppm of the compound of Formula (II). In some embodiments, the composition comprises an undetectable amount of the compound of Formula (II).

Provided herein, in some embodiments, is a compound of Formula (I)

(I)

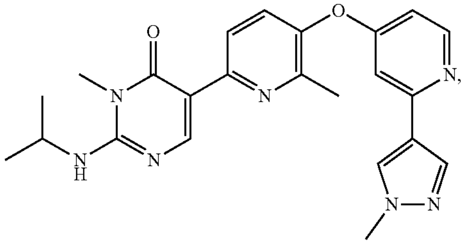

or a hydrate thereof, with no more than about 1% to about 5% by weight/weight of one or more impurities.

In some embodiments, the compound of Formula (I), or a hydrate thereof, comprises no more than about 1% to about 4.5% by weight/weight of one or more impurities. In some embodiments, the compound of Formula (I), or a hydrate thereof, comprises no more than about 1% to about 4% by weight/weight of one or more impurities. In some embodiments, the compound of Formula (I), or a hydrate thereof, comprises no more than about 1% to about 3.5% by weight/weight of one or more impurities. In some embodiments, the compound of Formula (I), or a hydrate thereof, comprises no more than about 1% to about 3% by weight/weight of one or more impurities. In some embodiments, the compound of Formula (I), or a hydrate thereof, comprises no more than about 1% to about 2.5% by weight/weight of one or more impurities. In some embodiments, the compound of Formula (I), or a hydrate thereof, comprises no more than about 1% to about 2% by weight/weight of one or more impurities. In some embodiments, the compound of Formula (I), or a hydrate thereof, comprises no more than about 1.5% to about 5% by weight/weight of one or more impurities. In some embodiments, the compound of Formula (I), or a hydrate thereof, comprises no more than about 1.5% to about 4.5% by weight/weight of one or more impurities. In some embodiments, the compound of Formula (I), or a hydrate thereof, comprises no more than about 1.5% to about 4% by weight/weight of one or more impurities. In some embodiments, the compound of Formula (I), or a hydrate thereof, comprises no more than about 1.5% to about 3.5% by weight/weight of one or more impurities. In some embodiments, the compound of Formula (I), or a hydrate thereof, comprises no more than about 1.5% to about 3% by weight/weight of one or more impurities. In some embodiments, the compound of Formula (I), or a hydrate thereof, comprises no more than about 1.5% to about 2.5% by weight/weight of one or more impurities. In some embodiments, the compound of Formula (I), or a hydrate thereof, comprises no more than about 1.5% to about 2% by weight/weight of one or more impurities. In some embodiments, the compound of Formula (I), or a hydrate thereof, comprises no more than about 2% to about 5% by weight/weight of one or more impurities. In some embodiments, the compound of Formula (I), or a hydrate thereof, comprises no more than about 2% to about 4.5% by weight/weight of one or more impurities. In some embodiments, the compound of Formula (I), or a hydrate thereof, comprises no more than about 2% to about 4% by weight/weight of one or more impurities. In some embodiments, the compound of Formula (I), or a hydrate thereof, comprises no more than about 2% to about 3.5% by weight/weight of one or more impurities. In some embodiments, the compound of Formula (I), or a hydrate thereof, comprises no more than about 2% to about 3% by weight/weight of one or more impurities. In some embodiments, the compound of Formula (I), or a hydrate thereof, comprises no more than about 2% to about 2.5% by weight/weight of one or more impurities.

In some embodiments, the compound of Formula (I), or a hydrate thereof, comprises no more than about 5% by weight/weight of one or more impurities. In some embodiments, the compound of Formula (I), or a hydrate thereof, comprises no more than about 4.5% by weight/weight of one or more impurities. In some embodiments, the compound of Formula (I), or a hydrate thereof, comprises no more than about 4% by weight/weight of one or more impurities. In some embodiments, the compound of Formula (I), or a hydrate thereof, comprises no more than about 3.5% by weight/weight of one or more impurities. In some embodiments, the compound of Formula (I), or a hydrate thereof, comprises no more than about 3% by weight/weight of one or more impurities. In some embodiments, the compound of Formula (I), or a hydrate thereof, comprises no more than about 2.5% by weight/weight of one or more impurities. In some embodiments, the compound of Formula (I), or a hydrate thereof, comprises no more than about 2% by weight/weight of one or more impurities. In some embodiments, the compound of Formula (I), or a hydrate thereof, comprises no more than about 1.5% by weight/weight of one or more impurities. In some embodiments, the compound of Formula (I), or a hydrate thereof, comprises no more than about 1% by weight/weight of one or more impurities.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

In some embodiments, the compound of Formula (I), or a hydrate thereof, comprises no more than about 0.1% to about 0.5% by weight/weight of a compound of Formula (III)

(III)

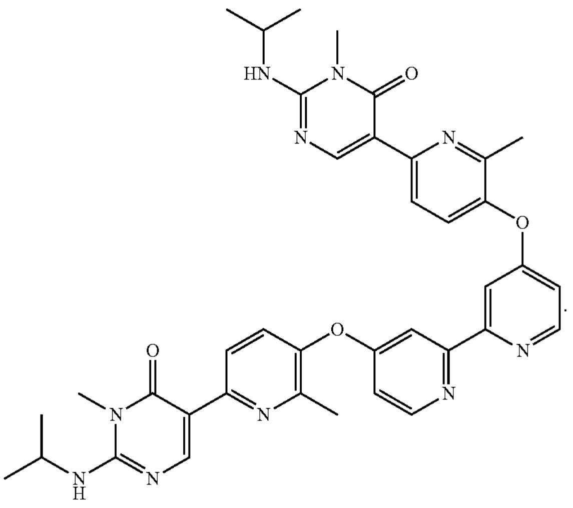

In some embodiments, the compound of Formula (I), or a hydrate thereof, comprises no more than about 0.1% to about 0.4% by weight/weight of the compound of Formula (III). In some embodiments, the compound of Formula (I), or a hydrate thereof, comprises no more than about 0.1% to about 0.3% by weight/weight of the compound of Formula (III). In some embodiments, the compound of Formula (I), or a hydrate thereof, comprises no more than about 0.1% to about 0.2% by weight/weight of the compound of Formula (III).

In some embodiments, the compound of Formula (I), or a hydrate thereof, comprises no more than about 0.2% to about 0.5% by weight/weight of the compound of Formula (III). In some embodiments, the compound of Formula (I), or a hydrate thereof, comprises no more than about 0.2% to about 0.4% by weight/weight of the compound of Formula (III). In some embodiments, the compound of Formula (I), or a hydrate thereof, comprises no more than about 0.2% to about 0.3% by weight/weight of the compound of Formula (III).

In some embodiments, the compound of Formula (I), or a hydrate thereof, comprises no more than about 0.5% by weight/weight of the compound of Formula (III). In some embodiments, the compound of Formula (I), or a hydrate thereof, comprises no more than about 0.4% by weight/weight of the compound of Formula (III). In some embodiments, the compound of Formula (I), or a hydrate thereof, comprises no more than about 0.3% by weight/weight of the compound of Formula (III). In some embodiments, the compound of Formula (I), or a hydrate thereof, comprises no more than about 0.2% by weight/weight of the compound of Formula (III). In some embodiments, the compound of Formula (I), or a hydrate thereof, comprises no more than about 0.1% by weight/weight of the compound of Formula (III).

In some embodiments, the compound of Formula (I), or a hydrate thereof, comprises no more than about 0.6% by weight/weight of the compound of Formula (III). In some embodiments, the compound of Formula (I), or a hydrate thereof, comprises no more than about 0.7% by weight/weight of the compound of Formula (III). In some embodiments, the compound of Formula (I), or a hydrate thereof, comprises no more than about 0.8% by weight/weight of the compound of Formula (III). In some embodiments, the compound of Formula (I), or a hydrate thereof, comprises no more than about 0.9% by weight/weight of the compound of Formula (III). In some embodiments, the compound of Formula (I), or a hydrate thereof, comprises no more than about 1% by weight/weight of the compound of Formula (III). In some embodiments, the compound of Formula (I), or a hydrate thereof, comprises no more than about 2% by weight/weight of the compound of Formula (III). In some embodiments, the compound of Formula (I), or a hydrate thereof, comprises no more than about 3% by weight/weight of the compound of Formula (III). In some embodiments, the compound of Formula (I), or a hydrate thereof, comprises no more than about 4% by weight/weight of the compound of Formula (III). In some embodiments, the compound of Formula (I), or a hydrate thereof, comprises no more than about 5% by weight/weight of the compound of Formula (III). In some embodiments, the compound of Formula (I), or a hydrate thereof, comprises no more than about 6% by weight/weight of the compound of Formula (III). In some embodiments, the compound of Formula (I), or a hydrate thereof, comprises no more than about 7% by weight/weight of the compound of Formula (III). In some embodiments, the compound of Formula (I), or a hydrate thereof, comprises no more than about 8% by weight/weight of the compound of Formula (III). In some embodiments, the compound of Formula (I), or a hydrate thereof, comprises no more than about 9% by weight/weight of the compound of Formula (III). In some embodiments, the compound of Formula (I), or a hydrate thereof, comprises no more than about 10% by weight/weight of the compound of Formula (III).

In some embodiments, the compound of Formula (I), or a hydrate thereof, comprises no more than about 0.1% to about 0.3% by weight/weight of a compound of Formula (IV)

(IV)

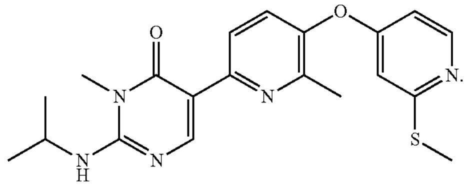

In some embodiments, the compound of Formula (I), or a hydrate thereof, comprises no more than about 0.1% to about 0.25% by weight/weight of the compound of Formula (IV). In some embodiments, the compound of Formula (I), or a hydrate thereof, comprises no more than about 0.1% to about 0.2% by weight/weight of the compound of Formula (IV). In some embodiments, the compound of Formula (I), or a hydrate thereof, comprises no more than about 0.1% to about 0.18% by weight/weight of the compound of Formula (IV). In some embodiments, the compound of Formula (I), or a hydrate thereof, comprises no more than about 0.1% to about 0.15% by weight/weight of the compound of Formula (IV).

In some embodiments, the compound of Formula (I), or a hydrate thereof, comprises no more than about 0.3% by weight/weight of the compound of Formula (IV). In some embodiments, the compound of Formula (I), or a hydrate thereof, comprises no more than about 0.25% weight/weight of the compound of Formula (IV). In some embodiments, the compound of Formula (I), or a hydrate thereof, comprises no more than about 0.2% weight/weight of the compound of Formula (IV). In some embodiments, the compound of Formula (I), or a hydrate thereof, comprises no more than about 0.18% weight/weight of the compound of Formula (IV). In some embodiments, the compound of Formula (I), or a hydrate thereof, comprises no more than about 0.15% weight/weight of the compound of Formula (IV). In some embodiments, the compound of Formula (I), or a hydrate thereof, comprises no more than about 0.13% weight/weight of the compound of Formula (IV). In some embodiments, the compound of Formula (I), or a hydrate thereof, comprises no more than about 0.1% weight/weight of the compound of Formula (IV).

In some embodiments, the compound of Formula (I), or a hydrate thereof, comprises no more than about 0.4% by weight/weight of the compound of Formula (IV). In some embodiments, the compound of Formula (I), or a hydrate thereof, comprises no more than about 0.5% by weight/weight of the compound of Formula (IV). In some embodiments, the compound of Formula (I), or a hydrate thereof, comprises no more than about 0.6% by weight/weight of the compound of Formula (IV). In some embodiments, the compound of Formula (I), or a hydrate thereof, comprises no more than about 0.7% by weight/weight of the compound of Formula (IV). In some embodiments, the compound of Formula (I), or a hydrate thereof, comprises no more than about 0.8% by weight/weight of the compound of Formula (IV). In some embodiments, the compound of Formula (I), or a hydrate thereof, comprises no more than about 0.9% by weight/weight of the compound of Formula (IV). In some embodiments, the compound of Formula (I), or a hydrate thereof, comprises no more than about 1% by weight/weight of the compound of Formula (IV). In some embodiments, the compound of Formula (I), or a hydrate thereof, comprises no more than about 2% by weight/weight of the compound of Formula (IV). In some embodiments, the compound of Formula (I), or a hydrate thereof, comprises no more than about 3% by weight/weight of the compound of Formula (IV). In some embodiments, the compound of Formula (I), or a hydrate thereof, comprises no more than about 4% by weight/weight of the compound of Formula (IV). In some embodiments, the compound of Formula (I), or a hydrate thereof, comprises no more than about 5% by weight/weight of the compound of Formula (IV). In some embodiments, the compound of Formula (I), or a hydrate thereof, comprises no more than about 6% by weight/weight of the compound of Formula (IV). In some embodiments, the compound of Formula (I), or a hydrate thereof, comprises no more than about 7% by weight/weight of the compound of Formula (IV). In some embodiments, the compound of Formula (I), or a hydrate thereof, comprises no more than about 8% by weight/weight of the compound of Formula (IV). In some embodiments, the compound of Formula (I), or a hydrate thereof, comprises no more than about 9% by weight/weight of the compound of Formula (IV). In some embodiments, the compound of Formula (I), or a hydrate thereof, comprises no more than about 10% by weight/weight of the compound of Formula (IV).

In some embodiments, the compound of Formula (I), or a hydrate thereof, comprises no more than about 0.1% to about 0.5% by weight/weight of a compound of Formula (V)

(V)

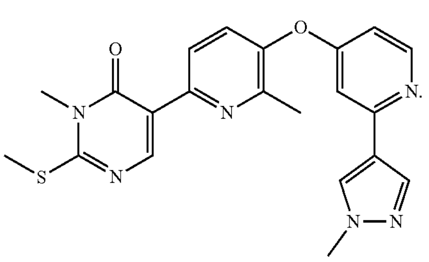

In some embodiments, the compound of Formula (I), or a hydrate thereof, comprises no more than about 0.1% to about 0.4% by weight/weight of the compound of Formula (V). In some embodiments, the compound of Formula (I), or a hydrate thereof, comprises no more than about 0.1% to about 0.3% by weight/weight of the compound of Formula (V). In some embodiments, the compound of Formula (I), or a hydrate thereof, comprises no more than about 0.1% to about 0.2% by weight/weight of the compound of Formula (V). In some embodiments, the compound of Formula (I), or a hydrate thereof, comprises no more than about 0.2% to about 0.5% by weight/weight of the compound of Formula (V). In some embodiments, the compound of Formula (I), or a hydrate thereof, comprises no more than about 0.2% to about 0.4% by weight/weight of the compound of Formula (V). In some embodiments, the compound of Formula (I), or a hydrate thereof, comprises no more than about 0.2% to about 0.3% by weight/weight of the compound of Formula (V).

In some embodiments, the compound of Formula (I), or a hydrate thereof, comprises no more than about 0.5% by weight/weight of the compound of Formula (V). In some embodiments, the compound of Formula (I), or a hydrate thereof, comprises no more than about 0.45% by weight/weight of the compound of Formula (V). In some embodiments, the compound of Formula (I), or a hydrate thereof, comprises no more than about 0.4% by weight/weight of the compound of Formula (V). In some embodiments, the compound of Formula (I), or a hydrate thereof, comprises no more than about 0.35% by weight/weight of the compound of Formula (V). In some embodiments, the compound of Formula (I), or a hydrate thereof, comprises no more than about 0.3% by weight/weight of the compound of Formula (V). In some embodiments, the compound of Formula (I), or a hydrate thereof, comprises no more than about 0.25% by weight/weight of the compound of Formula (V). In some embodiments, the compound of Formula (I), or a hydrate thereof, comprises no more than about 0.2% by weight/weight of the compound of Formula (V). In some embodiments, the compound of Formula (I), or a hydrate thereof, comprises no more than about 0.15% by weight/weight of the compound of Formula (V). In some embodiments, the compound of Formula (I), or a hydrate thereof, comprises no more than about 0.1% by weight/weight of the compound of Formula (V).

In some embodiments, the compound of Formula (I), or a hydrate thereof, comprises no more than about 0.6% by weight/weight of the compound of Formula (V). In some embodiments, the compound of Formula (I), or a hydrate thereof, comprises no more than about 0.7% by weight/weight of the compound of Formula (V). In some embodiments, the compound of Formula (I), or a hydrate thereof, comprises no more than about 0.8% by weight/weight of the compound of Formula (V). In some embodiments, the compound of Formula (I), or a hydrate thereof, comprises no more than about 0.9% by weight/weight of the compound of Formula (V). In some embodiments, the compound of Formula (I), or a hydrate thereof, comprises no more than about 1% by weight/weight of the compound of Formula (V). In some embodiments, the compound of Formula (I), or a hydrate thereof, comprises no more than about 2% by weight/weight of the compound of Formula (V). In some embodiments, the compound of Formula (I), or a hydrate thereof, comprises no more than about 3% by weight/weight of the compound of Formula (V). In some embodiments, the compound of Formula (I), or a hydrate thereof, comprises no more than about 4% by weight/weight of the compound of Formula (V). In some embodiments, the compound of Formula (I), or a hydrate thereof, comprises no more than about 5% by weight/weight of the compound of Formula (V). In some embodiments, the compound of Formula (I), or a hydrate thereof, comprises no more than about 6% by weight/weight of the compound of Formula (V). In some embodiments, the compound of Formula (I), or a hydrate thereof, comprises no more than about 7% by weight/weight of the compound of Formula (V). In some embodiments, the compound of Formula (I), or a hydrate thereof, comprises no more than about 8% by weight/weight of the compound of Formula (V). In some embodiments, the compound of Formula (I), or a hydrate thereof, comprises no more than about 9% by weight/weight of the compound of Formula (V). In some embodiments, the compound of Formula (I), or a hydrate thereof, comprises no more than about 10% by weight/weight of the compound of Formula (V).

In some embodiments, the compound of Formula (I), or a hydrate thereof, comprises no more than about 0.1% to about 0.5% by weight/weight of a compound of Formula (VI)

(VI)

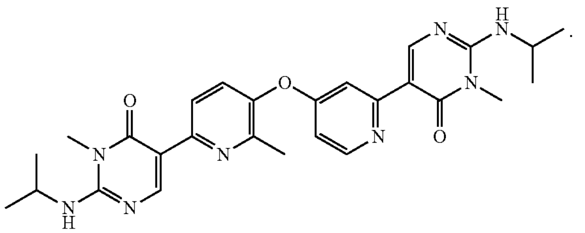

In some embodiments, the compound of Formula (I), or a hydrate thereof, comprises no more than about 0.1% to about 0.4% by weight/weight of the compound of Formula (VI). In some embodiments, the compound of Formula (I), or a hydrate thereof, comprises no more than about 0.1% to about 0.3% by weight/weight of the compound of Formula (VI). In some embodiments, the compound of Formula (I), or a hydrate thereof, comprises no more than about 0.1% to about 0.2% by weight/weight of the compound of Formula (VI). In some embodiments, the compound of Formula (I), or a hydrate thereof, comprises no more than about 0.2% to about 0.5% by weight/weight of the compound of Formula (VI). In some embodiments, the compound of Formula (I), or a hydrate thereof, comprises no more than about 0.2% to about 0.4% by weight/weight of the compound of Formula (VI). In some embodiments, the compound of Formula (I), or a hydrate thereof, comprises no more than about 0.2% to about 0.3% by weight/weight of the compound of Formula (VI).

In some embodiments, the compound of Formula (I), or a hydrate thereof, comprises no more than about 0.5% by weight/weight of the compound of Formula (VI). In some embodiments, the compound of Formula (I), or a hydrate thereof, comprises no more than about 0.45% by weight/weight of the compound of Formula (VI). In some embodiments, the compound of Formula (I), or a hydrate thereof, comprises no more than about 0.4% by weight/weight of the compound of Formula (VI). In some embodiments, the compound of Formula (I), or a hydrate thereof, comprises no more than about 0.35% by weight/weight of the compound of Formula (VI). In some embodiments, the compound of Formula (I), or a hydrate thereof, comprises no more than about 0.3% by weight/weight of the compound of Formula (VI). In some embodiments, the compound of Formula (I), or a hydrate thereof, comprises no more than about 0.25% by weight/weight of the compound of Formula (VI). In some embodiments, the compound of Formula (I), or a hydrate thereof, comprises no more than about 0.2% by weight/weight of the compound of Formula (VI). In some embodiments, the compound of Formula (I), or a hydrate thereof, comprises no more than about 0.15% by weight/weight of the compound of Formula (VI). In some embodiments, the compound of Formula (I), or a hydrate thereof, comprises no more than about 0.1% by weight/weight of the compound of Formula (VI).

In some embodiments, the compound of Formula (I), or a hydrate thereof, comprises no more than about 0.6% by weight/weight of the compound of Formula (VI). In some embodiments, the compound of Formula (I), or a hydrate thereof, comprises no more than about 0.7% by weight/weight of the compound of Formula (VI). In some embodiments, the compound of Formula (I), or a hydrate thereof, comprises no more than about 0.8% by weight/weight of the compound of Formula (VI). In some embodiments, the compound of Formula (I), or a hydrate thereof, comprises no more than about 0.9% by weight/weight of the compound of Formula (VI). In some embodiments, the compound of Formula (I), or a hydrate thereof, comprises no more than about 1% by weight/weight of the compound of Formula (VI). In some embodiments, the compound of Formula (I), or a hydrate thereof, comprises no more than about 2% by weight/weight of the compound of Formula (VI). In some embodiments, the compound of Formula (I), or a hydrate thereof, comprises no more than about 3% by weight/weight of the compound of Formula (VI). In some embodiments, the compound of Formula (I), or a hydrate thereof, comprises no more than about 4% by weight/weight of the compound of Formula (VI). In some embodiments, the compound of Formula (I), or a hydrate thereof, comprises no more than about 5% by weight/weight of the compound of Formula (VI). In some embodiments, the compound of Formula (I), or a hydrate thereof, comprises no more than about 6% by weight/weight of the compound of Formula (VI). In some embodiments, the compound of Formula (I), or a hydrate thereof, comprises no more than about 7% by weight/weight of the compound of Formula (VI). In some embodiments, the compound of Formula (I), or a hydrate thereof, comprises no more than about 8% by weight/weight of the compound of Formula (VI). In some embodiments, the compound of Formula (I), or a hydrate thereof, comprises no more than about 9% by weight/weight of the compound of Formula (VI). In some embodiments, the compound of Formula (I), or a hydrate thereof, comprises no more than about 10% by weight/weight of the compound of Formula (VI).

In some embodiments, the compound of Formula (I), or a hydrate thereof, comprises no more than about 0.05% to about 0.3% by weight/weight of a compound of Formula (VII)

(VII)

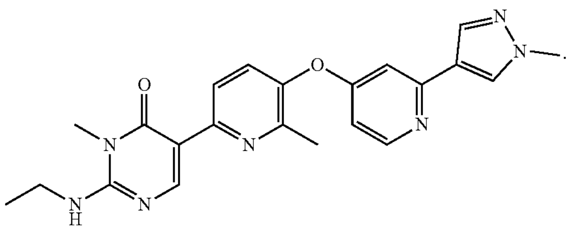

In some embodiments, the compound of Formula (I), or a hydrate thereof, comprises no more than about 0.05% to about 0.25% by weight/weight of the compound of Formula (VII). In some embodiments, the compound of Formula (I), or a hydrate thereof, comprises no more than about 0.05% to about 0.2% by weight/weight of the compound of Formula (VII). In some embodiments, the compound of Formula (I), or a hydrate thereof, comprises no more than about 0.05% to about 0.15% by weight/weight of the compound of Formula (VII). In some embodiments, the compound of Formula (I), or a hydrate thereof, comprises no more than about 0.05% to about 0.10% by weight/weight of the compound of Formula (VII).

In some embodiments, the compound of Formula (I), or a hydrate thereof, comprises no more than about 0.1% to about 0.3% by weight/weight of the compound of Formula (VII). In some embodiments, the compound of Formula (I), or a hydrate thereof, comprises no more than about 0.1% to about 0.25% by weight/weight of the compound of Formula (VII). In some embodiments, the compound of Formula (I), or a hydrate thereof, comprises no more than about 0.1% to about 0.2% by weight/weight of the compound of Formula (VII). In some embodiments, the compound of Formula (I), or a hydrate thereof, comprises no more than about 0.1% to about 0.15% by weight/weight of the compound of Formula (VII).

In some embodiments, the compound of Formula (I), or a hydrate thereof, comprises no more than about 0.3% by weight/weight of the compound of Formula (VII). In some embodiments, the compound of Formula (I), or a hydrate thereof, comprises no more than about 0.25% by weight/weight of the compound of Formula (VII). In some embodiments, the compound of Formula (I), or a hydrate thereof, comprises no more than about 0.2% by weight/weight of the compound of Formula (VII). In some embodiments, the compound of Formula (I), or a hydrate thereof, comprises no more than about 0.15% by weight/weight of the compound of Formula (VII). In some embodiments, the compound of Formula (I), or a hydrate thereof, comprises no more than about 0.1% by weight/weight of the compound of Formula (VII). In some embodiments, the compound of Formula (I), or a hydrate thereof, comprises no more than about 0.05% by weight/weight of the compound of Formula (VII).

In some embodiments, the compound of Formula (I), or a hydrate thereof, comprises no more than about 0.4% by weight/weight of the compound of Formula (VII). In some embodiments, the compound of Formula (I), or a hydrate thereof, comprises no more than about 0.5% by weight/weight of the compound of Formula (VII). In some embodiments, the compound of Formula (I), or a hydrate thereof, comprises no more than about 0.6% by weight/weight of the compound of Formula (VII). In some embodiments, the compound of Formula (I), or a hydrate thereof, comprises no more than about 0.7% by weight/weight of the compound of Formula (VII). In some embodiments, the compound of Formula (I), or a hydrate thereof, comprises no more than about 0.8% by weight/weight of the compound of Formula (VII). In some embodiments, the compound of Formula (I), or a hydrate thereof, comprises no more than about 0.9% by weight/weight of the compound of Formula (VII). In some embodiments, the compound of Formula (I), or a hydrate thereof, comprises no more than about 1% by weight/weight of the compound of Formula (VII). In some embodiments, the compound of Formula (I), or a hydrate thereof, comprises no more than about 2% by weight/weight of the compound of Formula (VII). In some embodiments, the compound of Formula (I), or a hydrate thereof, comprises no more than about 3% by weight/weight of the compound of Formula (VII). In some embodiments, the compound of Formula (I), or a hydrate thereof, comprises no more than about 4% by weight/weight of the compound of Formula (VII). In some embodiments, the compound of Formula (I), or a hydrate thereof, comprises no more than about 5% by weight/weight of the compound of Formula (VII). In some embodiments, the compound of Formula (I), or a hydrate thereof, comprises no more than about 6% by weight/weight of the compound of Formula (VII). In some embodiments, the compound of Formula (I), or a hydrate thereof, comprises no more than about 7% by weight/weight of the compound of Formula (VII). In some embodiments, the compound of Formula (I), or a hydrate thereof, comprises no more than about 8% by weight/weight of the compound of Formula (VII). In some embodiments, the compound of Formula (I), or a hydrate thereof, comprises no more than about 9% by weight/weight of the compound of Formula (VII). In some embodiments, the compound of Formula (I), or a hydrate thereof, comprises no more than about 10% by weight/weight of the compound of Formula (VII).

In some embodiments, the compound of Formula (I), or a hydrate thereof, comprises no more than about 0.1% to about 0.3% by weight/weight of a compound of Formula (VIII)

(VIII)

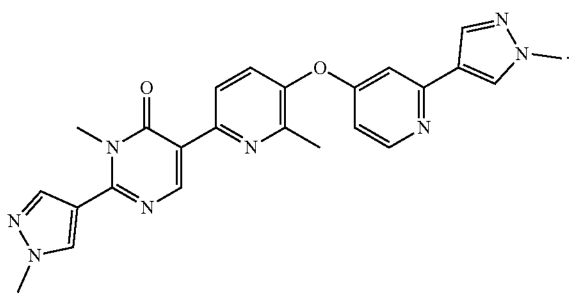

In some embodiments, the compound of Formula (I), or a hydrate thereof, comprises no more than about 0.1% to about 0.25% by weight/weight of the compound of Formula (VIII). In some embodiments, the compound of Formula (I), or a hydrate thereof, comprises no more than about 0.1% to about 0.2% by weight/weight of the compound of Formula (VIII). In some embodiments, the compound of Formula (I), or a hydrate thereof, comprises no more than about 0.1% to about 0.18% by weight/weight of the compound of Formula (VIII). In some embodiments, the compound of Formula (I), or a hydrate thereof, comprises no more than about 0.1% to about 0.15% by weight/weight of the compound of Formula (VIII).

In some embodiments, the compound of Formula (I), or a hydrate thereof, comprises no more than about 0.3% by weight/weight of the compound of Formula (VIII). In some embodiments, the compound of Formula (I), or a hydrate thereof, comprises no more than about 0.25% weight/weight of the compound of Formula (VIII). In some embodiments, the compound of Formula (I), or a hydrate thereof, comprises no more than about 0.2% weight/weight of the compound of Formula (VIII). In some embodiments, the compound of Formula (I), or a hydrate thereof, comprises no more than about 0.18% weight/weight of the compound of Formula (VIII). In some embodiments, the compound of Formula (I), or a hydrate thereof, comprises no more than about 0.15% weight/weight of the compound of Formula (VIII). In some embodiments, the compound of Formula (I), or a hydrate thereof, comprises no more than about 0.13% weight/weight of the compound of Formula (VIII). In some embodiments, the compound of Formula (I), or a hydrate thereof, comprises no more than about 0.1% weight/weight of the compound of Formula (VIII).

In some embodiments, the compound of Formula (I), or a hydrate thereof, comprises no more than about 0.4% by weight/weight of the compound of Formula (VIII). In some embodiments, the compound of Formula (I), or a hydrate thereof, comprises no more than about 0.5% by weight/weight of the compound of Formula (VIII). In some embodiments, the compound of Formula (I), or a hydrate thereof, comprises no more than about 0.6% by weight/weight of the compound of Formula (VIII). In some embodiments, the compound of Formula (I), or a hydrate thereof, comprises no more than about 0.7% by weight/weight of the compound of Formula (VIII). In some embodiments, the compound of Formula (I), or a hydrate thereof, comprises no more than about 0.8% by weight/weight of the compound of Formula (VIII). In some embodiments, the compound of Formula (I), or a hydrate thereof, comprises no more than about 0.9% by weight/weight of the compound of Formula (VIII). In some embodiments, the compound of Formula (I), or a hydrate thereof, comprises no more than about 1% by weight/weight of the compound of Formula (VIII). In some embodiments, the compound of Formula (I), or a hydrate thereof, comprises no more than about 2% by weight/weight of the compound of Formula (VIII). In some embodiments, the compound of Formula (I), or a hydrate thereof, comprises no more than about 3% by weight/weight of the compound of Formula (VIII). In some embodiments, the compound of Formula (I), or a hydrate thereof, comprises no more than about 4% by weight/weight of the compound of Formula (VIII). In some embodiments, the compound of Formula (I), or a hydrate thereof, comprises no more than about 5% by weight/weight of the compound of Formula (VIII). In some embodiments, the compound of Formula (I), or a hydrate thereof, comprises no more than about 6% by weight/weight of the compound of Formula (VIII). In some embodiments, the compound of Formula (I), or a hydrate thereof, comprises no more than about 7% by weight/weight of the compound of Formula (VIII). In some embodiments, the compound of Formula (I), or a hydrate thereof, comprises no more than about 8% by weight/weight of the compound of Formula (VIII). In some embodiments, the compound of Formula (I), or a hydrate thereof, comprises no more than about 9% by weight/weight of the compound of Formula (VIII). In some embodiments, the compound of Formula (I), or a hydrate thereof, comprises no more than about 10% by weight/weight of the compound of Formula (VIII).

In some embodiments, the compound of Formula (I), or a hydrate thereof, comprises no more than about 0.1% to about 0.3% by weight/weight of a compound of Formula (IX)

(IX)

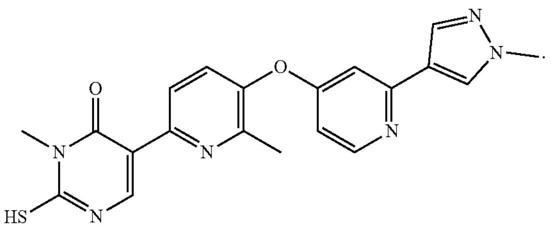

In some embodiments, the compound of Formula (I), or a hydrate thereof, comprises no more than about 0.1% to about 0.25% by weight/weight of the compound of Formula (IX). In some embodiments, the compound of Formula (I), or a hydrate thereof, comprises no more than about 0.1% to about 0.2% by weight/weight of the compound of Formula (IX). In some embodiments, the compound of Formula (I), or a hydrate thereof, comprises no more than about 0.1% to about 0.18% by weight/weight of the compound of Formula (IX). In some embodiments, the compound of Formula (I), or a hydrate thereof, comprises no more than about 0.1% to about 0.15% by weight/weight of the compound of Formula (IX).

In some embodiments, the compound of Formula (I), or a hydrate thereof, comprises no more than about 0.3% by weight/weight of the compound of Formula (IX). In some embodiments, the compound of Formula (I), or a hydrate thereof, comprises no more than about 0.25% weight/weight of the compound of Formula (IX). In some embodiments, the compound of Formula (I), or a hydrate thereof, comprises no more than about 0.2% weight/weight of the compound of Formula (IX). In some embodiments, the compound of Formula (I), or a hydrate thereof, comprises no more than about 0.18% weight/weight of the compound of Formula (IX). In some embodiments, the compound of Formula (I), or a hydrate thereof, comprises no more than about 0.15% weight/weight of the compound of Formula (IX). In some embodiments, the compound of Formula (I), or a hydrate thereof, comprises no more than about 0.13% weight/weight of the compound of Formula (IX). In some embodiments, the compound of Formula (I), or a hydrate thereof, comprises no more than about 0.1% weight/weight of the compound of Formula (IX).

In some embodiments, the compound of Formula (I), or a hydrate thereof, comprises no more than about 0.4% by weight/weight of the compound of Formula (IX). In some embodiments, the compound of Formula (I), or a hydrate thereof, comprises no more than about 0.5% by weight/weight of the compound of Formula (IX). In some embodiments, the compound of Formula (I), or a hydrate thereof, comprises no more than about 0.6% by weight/weight of the compound of Formula (IX). In some embodiments, the compound of Formula (I), or a hydrate thereof, comprises no more than about 0.7% by weight/weight of the compound of Formula (IX). In some embodiments, the compound of Formula (I), or a hydrate thereof, comprises no more than about 0.8% by weight/weight of the compound of Formula (IX). In some embodiments, the compound of Formula (I), or a hydrate thereof, comprises no more than about 0.9% by weight/weight of the compound of Formula (IX). In some embodiments, the compound of Formula (I), or a hydrate thereof, comprises no more than about 1% by weight/weight of the compound of Formula (IX). In some embodiments, the compound of Formula (I), or a hydrate thereof, comprises no more than about 2% by weight/weight of the compound of Formula (IX). In some embodiments, the compound of Formula (I), or a hydrate thereof, comprises no more than about 3% by weight/weight of the compound of Formula (IX). In some embodiments, the compound of Formula (I), or a hydrate thereof, comprises no more than about 4% by weight/weight of the compound of Formula (IX). In some embodiments, the compound of Formula (I), or a hydrate thereof, comprises no more than about 5% by weight/weight of the compound of Formula (IX). In some embodiments, the compound of Formula (I), or a hydrate thereof, comprises no more than about 6% by weight/weight of the compound of Formula (IX). In some embodiments, the compound of Formula (I), or a hydrate thereof, comprises no more than about 7% by weight/weight of the compound of Formula (IX). In some embodiments, the compound of Formula (I), or a hydrate thereof, comprises no more than about 8% by weight/weight of the compound of Formula (IX). In some embodiments, the compound of Formula (I), or a hydrate thereof, comprises no more than about 9% by weight/weight of the compound of Formula (IX). In some embodiments, the compound of Formula (I), or a hydrate thereof, comprises no more than about 10% by weight/weight of the compound of Formula (IX).

Provided herein, in some embodiments, are compositions comprising a compound of Formula (I)

(I)

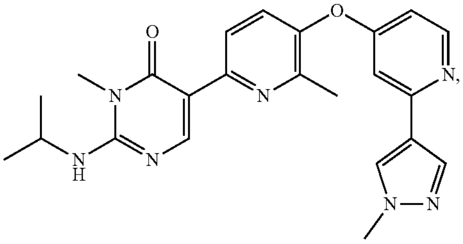

or a hydrate thereof,
having a purity of greater than or equal to about 95% weight/weight of the composition, and one or more impurities, wherein the one or more impurities are present in the composition at no more than about 5% weight/weight of the composition.

In some embodiments, the compound of Formula (I), or a hydrate thereof, is characterized by a purity of greater than or equal to about 96% weight/weight of the composition. In some embodiments, the compound of Formula (I), or a hydrate thereof, is characterized by a purity of greater than or equal to about 97% weight/weight of the composition. In some embodiments, the compound of Formula (I), or a hydrate thereof, is characterized by a purity of greater than or equal to about 98% weight/weight of the composition. In some embodiments, the compound of Formula (I), or a hydrate thereof, is characterized by a purity of greater than or equal to about 99% weight/weight of the composition.

In some embodiments, the one or more impurities are present in the composition at no more than about 4.5% weight/weight of the composition. In some embodiments, the one or more impurities are present in the composition at no more than about 4% weight/weight of the composition. In some embodiments, the one or more impurities are present in the composition at no more than about 3.5% weight/weight of the composition. In some embodiments, the one or more impurities are present in the composition at no more than about 3% weight/weight of the composition. In some embodiments, the one or more impurities are present in the composition at no more than about 2.5% weight/weight of the composition. In some embodiments, the one or more impurities are present in the composition at no more than about 2% weight/weight of the composition. In some embodiments, the one or more impurities are present in the composition at no more than about 1.5% weight/weight of the composition. In some embodiments, the one or more impurities are present in the composition at no more than about 1% weight/weight of the composition. In some embodiments, the one or more impurities are present in the composition at no more than about 0.5% weight/weight of the composition.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

Provided herein, in some embodiments, are compositions consisting essentially of a compound of Formula (I)

(I)

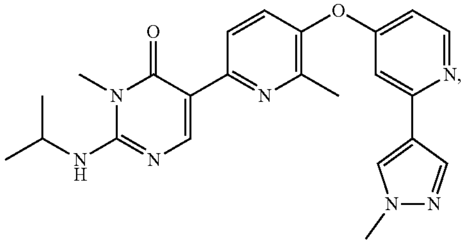

or a hydrate thereof,
having a purity of greater than or equal to about 95% weight/weight of the composition, and one or more impurities, wherein the one or more impurities are present in the composition at no more than about 5% weight/weight of the composition.

In some embodiments, the compound of Formula (I), or a hydrate thereof, is characterized by a purity of greater than or equal to about 96% weight/weight of the composition. In some embodiments, the compound of Formula (I), or a hydrate thereof, is characterized by a purity of greater than or equal to about 97% weight/weight of the composition. In some embodiments, the compound of Formula (I), or a hydrate thereof, is characterized by a purity of greater than or equal to about 98% weight/weight of the composition. In some embodiments, the compound of Formula (I), or a hydrate thereof, is characterized by a purity of greater than or equal to about 99% weight/weight of the composition.

In some embodiments, the one or more impurities are present in the composition at no more than about 4.5% weight/weight of the composition. In some embodiments, the one or more impurities are present in the composition at no more than about 4% weight/weight of the composition. In some embodiments, the one or more impurities are present in the composition at no more than about 3.5% weight/weight of the composition. In some embodiments, the one or more impurities are present in the composition at no more than about 3% weight/weight of the composition. In some embodiments, the one or more impurities are present in the composition at no more than about 2.5% weight/weight of the composition. In some embodiments, the one or more impurities are present in the composition at no more than about 2% weight/weight of the composition. In some embodiments, the one or more impurities are present in the composition at no more than about 1.5% weight/weight of the composition. In some embodiments, the one or more impurities are present in the composition at no more than about 1% weight/weight of the composition. In some embodiments, the one or more impurities are present in the composition at no more than about 0.5% weight/weight of the composition.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

Provided herein, in some embodiments, is a compound of Formula (I)

(I)

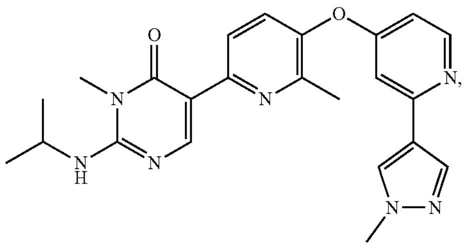

or a hydrate thereof, that is substantially free of one or more impurities.

In some embodiments, the amount of impurities is less than about 10% area under the curve when measured by HPLC. In some embodiments, the amount of impurities is less than about 9.5% area under the curve when measured by HPLC. In some embodiments, the amount of impurities is less than about 9% area under the curve when measured by HPLC. In some embodiments, the amount of impurities is less than about 8.5% area under the curve when measured by HPLC. In some embodiments, the amount of impurities is less than about 8% area under the curve when measured by HPLC. In some embodiments, the amount of impurities is less than about 7.5% area under the curve when measured by HPLC. In some embodiments, the amount of impurities is less than about 7% area under the curve when measured by HPLC. In some embodiments, the amount of impurities is less than about 6.5% area under the curve when measured by HPLC. In some embodiments, the amount of impurities is less than about 6% area under the curve when measured by HPLC. In some embodiments, the amount of impurities is less than about 5.5% area under the curve when measured by HPLC. In some embodiments, the amount of impurities is less than about 5% area under the curve when measured by HPLC. In some embodiments, the amount of impurities is less than about 4.5% area under the curve when measured by HPLC. In some embodiments, the amount of impurities is less than about 4% area under the curve when measured by HPLC. In some embodiments, the amount of impurities is less than about 3.5% area under the curve when measured by HPLC. In some embodiments, the amount of impurities is less than about 3% area under the curve when measured by HPLC. In some embodiments, the amount of impurities is less than about 2.5% area under the curve when measured by HPLC. In some embodiments, the amount of impurities is less than about 2% area under the curve when measured by HPLC. In some embodiments, the amount of impurities is less than about 1.5% area under the curve when measured by HPLC. In some embodiments, the amount of impurities is less than about 1% area under the curve when measured by HPLC. In some embodiments, the amount of impurities is less than about 0.5% area under the curve when measured by HPLC.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

In some embodiments, the compound of Formula (I), or a hydrate thereof, comprises no more than about 0.1% to about 0.5% area under the curve when measured by HPLC of a compound of Formula (III)

(III)

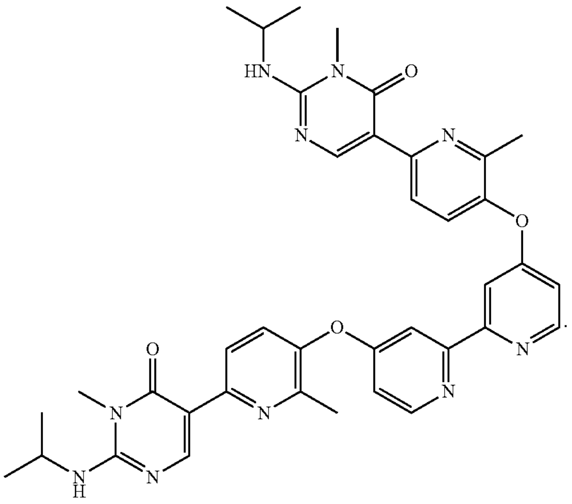

In some embodiments, the compound of Formula (I), or a hydrate thereof, comprises no more than about 0.1% to about 0.4% area under the curve when measured by HPLC of the compound of Formula (III). In some embodiments, the compound of Formula (I), or a hydrate thereof, comprises no more than about 0.1% to about 0.3% area under the curve when measured by HPLC of the compound of Formula (III).

In some embodiments, the compound of Formula (I), or a hydrate thereof, comprises no more than about 0.2% to about 0.5% area under the curve when measured by HPLC of the compound of Formula (III). In some embodiments, the compound of Formula (I), or a hydrate thereof, comprises no more than about 0.2% to about 0.4% area under the curve when measured by HPLC of the compound of Formula (III). In some embodiments, the compound of Formula (I), or a hydrate thereof, comprises no more than about 0.2% to about 0.3% area under the curve when measured by HPLC of the compound of Formula (III).

In some embodiments, the compound of Formula (I), or a hydrate thereof, comprises no more than about 0.5% area under the curve when measured by HPLC of the compound of Formula (III). In some embodiments, the compound of Formula (I), or a hydrate thereof, comprises no more than about 0.45% area under the curve when measured by HPLC of the compound of Formula (III). In some embodiments, the compound of Formula (I), or a hydrate thereof, comprises no more than about 0.4% area under the curve when measured by HPLC of the compound of Formula (III). In some embodiments, the compound of Formula (I), or a hydrate thereof, comprises no more than about 0.35% area under the curve when measured by HPLC of the compound of Formula (III). In some embodiments, the compound of Formula (I), or a hydrate thereof, comprises no more than about 0.3% area under the curve when measured by HPLC of the compound of Formula (III). In some embodiments, the compound of Formula (I), or a hydrate thereof, comprises no more than about 0.25% area under the curve when measured by HPLC of the compound of Formula (III). In some embodiments, the compound of Formula (I), or a hydrate thereof, comprises no more than about 0.2% area under the curve when measured by HPLC of the compound of Formula (III). In some embodiments, the compound of Formula (I), or a hydrate thereof, comprises no more than about 0.15% area under the curve when measured by HPLC of the compound of Formula (III). In some embodiments, the compound of Formula (I), or a hydrate thereof, comprises no more than about 0.1% area under the curve when measured by HPLC of the compound of Formula (III).

In some embodiments, the compound of Formula (I), or a hydrate thereof, comprises no more than about 0.6% area under the curve when measured by HPLC of the compound of Formula (III). In some embodiments, the compound of Formula (I), or a hydrate thereof, comprises no more than about 0.7% area under the curve when measured by HPLC of the compound of Formula (III). In some embodiments, the compound of Formula (I), or a hydrate thereof, comprises no more than about 0.8% area under the curve when measured by HPLC of the compound of Formula (III). In some embodiments, the compound of Formula (I), or a hydrate thereof, comprises no more than about 0.9% area under the curve when measured by HPLC of the compound of Formula (III). In some embodiments, the compound of Formula (I), or a hydrate thereof, comprises no more than about 1% area under the curve when measured by HPLC of the compound of Formula (III). In some embodiments, the compound of Formula (I), or a hydrate thereof, comprises no more than about 2% area under the curve when measured by HPLC of the compound of Formula (III). In some embodiments, the compound of Formula (I), or a hydrate thereof, comprises no more than about 3% area under the curve when measured by HPLC of the compound of Formula (III). In some embodiments, the compound of Formula (I), or a hydrate thereof, comprises no more than about 4% area under the curve when measured by HPLC of the compound of Formula (III). In some embodiments, the compound of Formula (I), or a hydrate thereof, comprises no more than about 5% area under the curve when measured by HPLC of the compound of Formula (III). In some embodiments, the compound of Formula (I), or a hydrate thereof, comprises no more than about 6% area under the curve when measured by HPLC of the compound of Formula (III). In some embodiments, the compound of Formula (I), or a hydrate thereof, comprises no more than about 7% area under the curve when measured by HPLC of the compound of Formula (III). In some embodiments, the compound of Formula (I), or a hydrate thereof, comprises no more than about 8% area under the curve when measured by HPLC of the compound of Formula (III). In some embodiments, the compound of Formula (I), or a hydrate thereof, comprises no more than about 9% area under the curve when measured by HPLC of the compound of Formula (III). In some embodiments, the compound of Formula (I), or a hydrate thereof, comprises no more than about 10% area under the curve when measured by HPLC of the compound of Formula (III).

In some embodiments, the compound of Formula (I), or a hydrate thereof, comprises no more than about 0.1% to about 0.3% area under the curve when measured by HPLC of a compound of Formula (IV)

(IV)

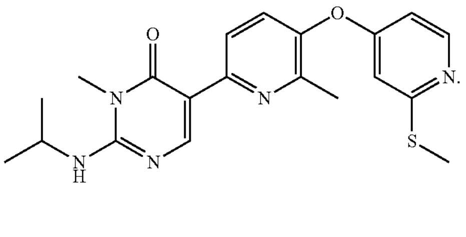

In some embodiments, the compound of Formula (I), or a hydrate thereof, comprises no more than about 0.1% to about 0.25% area under the curve when measured by HPLC of the compound of Formula (IV). In some embodiments, the compound of Formula (I), or a hydrate thereof, comprises no more than about 0.1% to about 0.2% area under the curve when measured by HPLC of the compound of Formula (IV). In some embodiments, the compound of Formula (I), or a hydrate thereof, comprises no more than about 0.1% to about 0.18% area under the curve when measured by HPLC of the compound of Formula (IV). In some embodiments, the compound of Formula (I), or a hydrate thereof, comprises no more than about 0.1% to about 0.15% area under the curve when measured by HPLC of the compound of Formula (IV).

In some embodiments, the compound of Formula (I), or a hydrate thereof, comprises no more than about 0.3% area under the curve when measured by HPLC of the compound of Formula (IV). In some embodiments, the compound of Formula (I), or a hydrate thereof, comprises no more than about 0.25% area under the curve when measured by HPLC of the compound of Formula (IV). In some embodiments, the compound of Formula (I), or a hydrate thereof, comprises no more than about 0.2% area under the curve when measured by HPLC of the compound of Formula (IV). In some embodiments, the compound of Formula (I), or a hydrate thereof, comprises no more than about 0.19% area under the curve when measured by HPLC of the compound of Formula (IV). In some embodiments, the compound of Formula (I), or a hydrate thereof, comprises no more than about 0.15% area under the curve when measured by HPLC of the compound of Formula (IV). In some embodiments, the compound of Formula (I), or a hydrate thereof, comprises no more than about 0.13% area under the curve when measured by HPLC of the compound of Formula (IV). In some embodiments, the compound of Formula (I), or a hydrate thereof, comprises no more than about 0.1% area under the curve when measured by HPLC of the compound of Formula (IV).

In some embodiments, the compound of Formula (I), or a hydrate thereof, comprises no more than about 0.4% area under the curve when measured by HPLC of the compound of Formula (IV). In some embodiments, the compound of Formula (I), or a hydrate thereof, comprises no more than about 0.5% area under the curve when measured by HPLC of the compound of Formula (IV). In some embodiments, the compound of Formula (I), or a hydrate thereof, comprises no more than about 0.6% area under the curve when measured by HPLC of the compound of Formula (IV). In some embodiments, the compound of Formula (I), or a hydrate thereof, comprises no more than about 0.7% area under the curve when measured by HPLC of the compound of Formula (IV). In some embodiments, the compound of Formula (I), or a hydrate thereof, comprises no more than about 0.8% area under the curve when measured by HPLC of the compound of Formula (IV). In some embodiments, the compound of Formula (I), or a hydrate thereof, comprises no more than about 0.9% area under the curve when measured by HPLC of the compound of Formula (IV). In some embodiments, the compound of Formula (I), or a hydrate thereof, comprises no more than about 1% area under the curve when measured by HPLC of the compound of Formula (IV). In some embodiments, the compound of Formula (I), or a hydrate thereof, comprises no more than about 2% area under the curve when measured by HPLC of the compound of Formula (IV). In some embodiments, the compound of Formula (I), or a hydrate thereof, comprises no more than about 3% area under the curve when measured by HPLC of the compound of Formula (IV). In some embodiments, the compound of Formula (I), or a hydrate thereof, comprises no more than about 4% area under the curve when measured by HPLC of the compound of Formula (IV). In some embodiments, the compound of Formula (I), or a hydrate thereof, comprises no more than about 5% area under the curve when measured by HPLC of the compound of Formula (IV). In some embodiments, the compound of Formula (I), or a hydrate thereof, comprises no more than about 6% area under the curve when measured by HPLC of the compound of Formula (IV). In some embodiments, the compound of Formula (I), or a hydrate thereof, comprises no more than about 7% area under the curve when measured by HPLC of the compound of Formula (IV). In some embodiments, the compound of Formula (I), or a hydrate thereof, comprises no more than about 8% area under the curve when measured by HPLC of the compound of Formula (IV). In some embodiments, the compound of Formula (I), or a hydrate thereof, comprises no more than about 9% area under the curve when measured by HPLC of the compound of Formula (IV). In some embodiments, the compound of Formula (I), or a hydrate thereof, comprises no more than about 10% area under the curve when measured by HPLC of the compound of Formula (IV).

In some embodiments, the compound of Formula (I), or a hydrate thereof, comprises no more than about 0.1% to about 0.5% area under the curve when measured by HPLC of a compound of Formula (V)

(V)

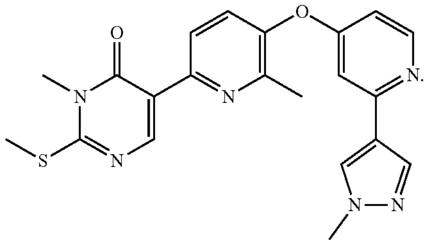

In some embodiments, the compound of Formula (I), or a hydrate thereof, comprises no more than about 0.1% to about 0.4% area under the curve when measured by HPLC of the compound of Formula (V). In some embodiments, the compound of Formula (I), or a hydrate thereof, comprises no more than about 0.1% to about 0.3% area under the curve when measured by HPLC of the compound of Formula (V). In some embodiments, the compound of Formula (I), or a hydrate thereof, comprises no more than about 0.1% to about 0.2% area under the curve when measured by HPLC of the compound of Formula (V). In some embodiments, the compound of Formula (I), or a hydrate thereof, comprises no more than about 0.2% to about 0.5% area under the curve when measured by HPLC of the compound of Formula (V). In some embodiments, the compound of Formula (I), or a hydrate thereof, comprises no more than about 0.2% to about 0.4% area under the curve when measured by HPLC of the compound of Formula (V). In some embodiments, the compound of Formula (I), or a hydrate thereof, comprises no more than about 0.2% to about 0.3% area under the curve when measured by HPLC of the compound of Formula (V).

In some embodiments, the compound of Formula (I), or a hydrate thereof, comprises no more than about 0.5% area under the curve when measured by HPLC of the compound of Formula (V). In some embodiments, the compound of Formula (I), or a hydrate thereof, comprises no more than about 0.45% area under the curve when measured by HPLC of the compound of Formula (V). In some embodiments, the compound of Formula (I), or a hydrate thereof, comprises no more than about 0.4% area under the curve when measured by HPLC of the compound of Formula (V). In some embodiments, the compound of Formula (I), or a hydrate thereof, comprises no more than about 0.35% area under the curve when measured by HPLC of the compound of Formula (V). In some embodiments, the compound of Formula (I), or a hydrate thereof, comprises no more than about 0.3% area under the curve when measured by HPLC of the compound of Formula (V). In some embodiments, the compound of Formula (I), or a hydrate thereof, comprises no more than about 0.29% area under the curve when measured by HPLC of the compound of Formula (V). In some embodiments, the compound of Formula (I), or a hydrate thereof, comprises no more than about 0.25% area under the curve when measured by HPLC of the compound of Formula (V). In some embodiments, the compound of Formula (I), or a hydrate thereof, comprises no more than about 0.2% area under the curve when measured by HPLC of the compound of Formula (V). In some embodiments, the compound of Formula (I), or a hydrate thereof, comprises no more than about 0.15% area under the curve when measured by HPLC of the compound of Formula (V). In some embodiments, the compound of Formula (I), or a hydrate thereof, comprises no more than about 0.14% area under the curve when measured by HPLC of the compound of Formula (V). In some embodiments, the compound of Formula (I), or a hydrate thereof, comprises no more than about 0.1% area under the curve when measured by HPLC of the compound of Formula (V).

In some embodiments, the compound of Formula (I), or a hydrate thereof, comprises no more than about 0.6% area under the curve when measured by HPLC of the compound of Formula (V). In some embodiments, the compound of Formula (I), or a hydrate thereof, comprises no more than about 0.7% area under the curve when measured by HPLC of the compound of Formula (V). In some embodiments, the compound of Formula (I), or a hydrate thereof, comprises no more than about 0.8% area under the curve when measured by HPLC of the compound of Formula (V). In some embodiments, the compound of Formula (I), or a hydrate thereof, comprises no more than about 0.9% area under the curve when measured by HPLC of the compound of Formula (V). In some embodiments, the compound of Formula (I), or a hydrate thereof, comprises no more than about 1% area under the curve when measured by HPLC of the compound of Formula (V). In some embodiments, the compound of Formula (I), or a hydrate thereof, comprises no more than about 2% area under the curve when measured by HPLC of the compound of Formula (V). In some embodiments, the compound of Formula (I), or a hydrate thereof, comprises no more than about 3% area under the curve when measured by HPLC of the compound of Formula (V). In some embodiments, the compound of Formula (I), or a hydrate thereof, comprises no more than about 4% area under the curve when measured by HPLC of the compound of Formula (V). In some embodiments, the compound of Formula (I), or a hydrate thereof, comprises no more than about 5% area under the curve when measured by HPLC of the compound of Formula (V). In some embodiments, the compound of Formula (I), or a hydrate thereof, comprises no more than about 6% area under the curve when measured by HPLC of the compound of Formula (V). In some embodiments, the compound of Formula (I), or a hydrate thereof, comprises no more than about 7% area under the curve when measured by HPLC of the compound of Formula (V). In some embodiments, the compound of Formula (I), or a hydrate thereof, comprises no more than about 8% area under the curve when measured by HPLC of the compound of Formula (V). In some embodiments, the compound of Formula (I), or a hydrate thereof, comprises no more than about 9% area under the curve when measured by HPLC of the compound of Formula (V). In some embodiments, the compound of Formula (I), or a hydrate thereof, comprises no more than about 10% area under the curve when measured by HPLC of the compound of Formula (V).

In some embodiments, the compound of Formula (I), or a hydrate thereof, comprises no more than about 0.05% to about 0.5% area under the curve when measured by HPLC of a compound of Formula (VI)

(VI)

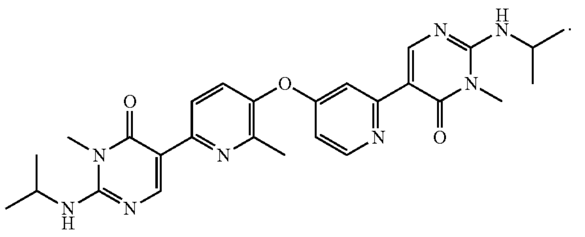

In some embodiments, the compound of Formula (I), or a hydrate thereof, comprises no more than about 0.1% to about 0.4% area under the curve when measured by HPLC of the compound of Formula (VI). In some embodiments, the compound of Formula (I), or a hydrate thereof, comprises no more than about 0.1% to about 0.3% area under the curve when measured by HPLC of the compound of Formula (VI). In some embodiments, the compound of Formula (I), or a hydrate thereof, comprises no more than about 0.1% to about 0.2% area under the curve when measured by HPLC of the compound of Formula (VI).

In some embodiments, the compound of Formula (I), or a hydrate thereof, comprises no more than about 0.2% to about 0.5% area under the curve when measured by HPLC of the compound of Formula (VI). In some embodiments, the compound of Formula (I), or a hydrate thereof, comprises no more than about 0.2% to about 0.4% area under the curve when measured by HPLC of the compound of Formula (VI). In some embodiments, the compound of Formula (I), or a hydrate thereof, comprises no more than about 0.2% to about 0.3% area under the curve when measured by HPLC of the compound of Formula (VI).

In some embodiments, the compound of Formula (I), or a hydrate thereof, comprises no more than about 0.5% area under the curve when measured by HPLC of the compound of Formula (VI). In some embodiments, the compound of Formula (I), or a hydrate thereof, comprises no more than about 0.45% area under the curve when measured by HPLC of the compound of Formula (VI). In some embodiments, the compound of Formula (I), or a hydrate thereof, comprises no more than about 0.4% area under the curve when measured by HPLC of the compound of Formula (VI). In some embodiments, the compound of Formula (I), or a hydrate thereof, comprises no more than about 0.35% area under the curve when measured by HPLC of the compound of Formula (VI). In some embodiments, the compound of Formula (I), or a hydrate thereof, comprises no more than about 0.3% area under the curve when measured by HPLC of the compound of Formula (VI). In some embodiments, the compound of Formula (I), or a hydrate thereof, comprises no more than about 0.25% area under the curve when measured by HPLC of the compound of Formula (VI). In some embodiments, the compound of Formula (I), or a hydrate thereof, comprises no more than about 0.2% area under the curve when measured by HPLC of the compound of Formula (VI). In some embodiments, the compound of Formula (I), or a hydrate thereof, comprises no more than about 0.15% area under the curve when measured by HPLC of the compound of Formula (VI). In some embodiments, the compound of Formula (I), or a hydrate thereof, comprises no more than about 0.1% area under the curve when measured by HPLC of the compound of Formula (VI). In some embodiments, the compound of Formula (I), or a hydrate thereof, comprises no more than about 0.05% area under the curve when measured by HPLC of the compound of Formula (VI).

In some embodiments, the compound of Formula (I), or a hydrate thereof, comprises no more than about 0.6% area under the curve when measured by HPLC of the compound of Formula (VI). In some embodiments, the compound of Formula (I), or a hydrate thereof, comprises no more than about 0.7% area under the curve when measured by HPLC of the compound of Formula (VI). In some embodiments, the compound of Formula (I), or a hydrate thereof, comprises no more than about 0.8% area under the curve when measured by HPLC of the compound of Formula (VI). In some embodiments, the compound of Formula (I), or a hydrate thereof, comprises no more than about 0.9% area under the curve when measured by HPLC of the compound of Formula (VI). In some embodiments, the compound of Formula (I), or a hydrate thereof, comprises no more than about 1% area under the curve when measured by HPLC of the compound of Formula (VI). In some embodiments, the compound of Formula (I), or a hydrate thereof, comprises no more than about 2% area under the curve when measured by HPLC of the compound of Formula (VI). In some embodiments, the compound of Formula (I), or a hydrate thereof, comprises no more than about 3% area under the curve when measured by HPLC of the compound of Formula (VI). In some embodiments, the compound of Formula (I), or a hydrate thereof, comprises no more than about 4% area under the curve when measured by HPLC of the compound of Formula (VI). In some embodiments, the compound of Formula (I), or a hydrate thereof, comprises no more than about 5% area under the curve when measured by HPLC of the compound of Formula (VI). In some embodiments, the compound of Formula (I), or a hydrate thereof, comprises no more than about 6% area under the curve when measured by HPLC of the compound of Formula (VI). In some embodiments, the compound of Formula (I), or a hydrate thereof, comprises no more than about 7% area under the curve when measured by HPLC of the compound of Formula (VI). In some embodiments, the compound of Formula (I), or a hydrate thereof, comprises no more than about 8% area under the curve when measured by HPLC of the compound of Formula (VI). In some embodiments, the compound of Formula (I), or a hydrate thereof, comprises no more than about 9% area under the curve when measured by HPLC of the compound of Formula (VI). In some embodiments, the compound of Formula (I), or a hydrate thereof, comprises no more than about 10% area under the curve when measured by HPLC of the compound of Formula (VI).

In some embodiments, the compound of Formula (I), or a hydrate thereof, comprises no more than about 0.05% to about 0.3% area under the curve when measured by HPLC of a compound of Formula (VII)

(VII)

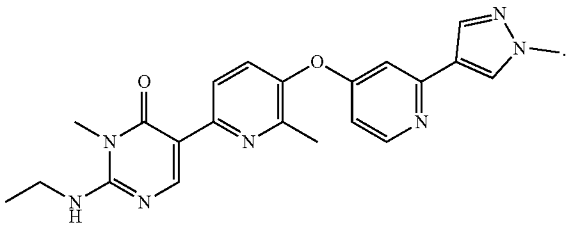

In some embodiments, the compound of Formula (I), or a hydrate thereof, comprises no more than about 0.05% to about 0.25% area under the curve when measured by HPLC of the compound of Formula (VII). In some embodiments, the compound of Formula (I), or a hydrate thereof, comprises no more than about 0.05% to about 0.2% area under the curve when measured by HPLC of the compound of Formula (VII). In some embodiments, the compound of Formula (I), or a hydrate thereof, comprises no more than about 0.05% to about 0.15% area under the curve when measured by HPLC of the compound of Formula (VII). In some embodiments, the compound of Formula (I), or a hydrate thereof, comprises no more than about 0.05% to about 0.15% area under the curve when measured by HPLC of the compound of Formula (VII).

In some embodiments, the compound of Formula (I), or a hydrate thereof, comprises no more than about 0.1% to about 0.3% area under the curve when measured by HPLC of the compound of Formula (VII). In some embodiments, the compound of Formula (I), or a hydrate thereof, comprises no more than about 0.1% to about 0.25% area under the curve when measured by HPLC of the compound of Formula (VII). In some embodiments, the compound of Formula (I), or a hydrate thereof, comprises no more than about 0.1% to about 0.2% area under the curve when measured by HPLC of the compound of Formula (VII). In some embodiments, the compound of Formula (I), or a hydrate thereof, comprises no more than about 0.1% to about 0.15% area under the curve when measured by HPLC of the compound of Formula (VII). In some embodiments, the compound of Formula (I), or a hydrate thereof, comprises no more than about 0.1% to about 0.15% area under the curve when measured by HPLC of the compound of Formula (VII).

In some embodiments, the compound of Formula (I), or a hydrate thereof, comprises no more than about 0.3% area under the curve when measured by HPLC of the compound of Formula (VII). In some embodiments, the compound of Formula (I), or a hydrate thereof, comprises no more than about 0.25% area under the curve when measured by HPLC of the compound of Formula (VII). In some embodiments, the compound of Formula (I), or a hydrate thereof, comprises no more than about 0.2% area under the curve when measured by HPLC of the compound of Formula (VII). In some embodiments, the compound of Formula (I), or a hydrate thereof, comprises no more than about 0.15% area under the curve when measured by HPLC of the compound of Formula (VII). In some embodiments, the compound of Formula (I), or a hydrate thereof, comprises no more than about 0.11% area under the curve when measured by HPLC of the compound of Formula (VII). In some embodiments, the compound of Formula (I), or a hydrate thereof, comprises no more than about 0.1% area under the curve when measured by HPLC of the compound of Formula (VII). In some embodiments, the compound of Formula (I), or a hydrate thereof, comprises no more than about 0.05% area under the curve when measured by HPLC of the compound of Formula (VII).

In some embodiments, the compound of Formula (I), or a hydrate thereof, comprises no more than about 0.4% area under the curve when measured by HPLC of the compound of Formula (VII). In some embodiments, the compound of Formula (I), or a hydrate thereof, comprises no more than about 0.5% area under the curve when measured by HPLC of the compound of Formula (VII). In some embodiments, the compound of Formula (I), or a hydrate thereof, comprises no more than about 0.6% area under the curve when measured by HPLC of the compound of Formula (VII). In some embodiments, the compound of Formula (I), or a hydrate thereof, comprises no more than about 0.7% area under the curve when measured by HPLC of the compound of Formula (VII). In some embodiments, the compound of Formula (I), or a hydrate thereof, comprises no more than about 0.8% area under the curve when measured by HPLC of the compound of Formula (VII). In some embodiments, the compound of Formula (I), or a hydrate thereof, comprises no more than about 0.9% area under the curve when measured by HPLC of the compound of Formula (VII). In some embodiments, the compound of Formula (I), or a hydrate thereof, comprises no more than about 1% area under the curve when measured by HPLC of the compound of Formula (VII). In some embodiments, the compound of Formula (I), or a hydrate thereof, comprises no more than about 2% area under the curve when measured by HPLC of the compound of Formula (VII). In some embodiments, the compound of Formula (I), or a hydrate thereof, comprises no more than about 3% area under the curve when measured by HPLC of the compound of Formula (VII). In some embodiments, the compound of Formula (I), or a hydrate thereof, comprises no more than about 4% area under the curve when measured by HPLC of the compound of Formula (VII). In some embodiments, the compound of Formula (I), or a hydrate thereof, comprises no more than about 5% area under the curve when measured by HPLC of the compound of Formula (VII). In some embodiments, the compound of Formula (I), or a hydrate thereof, comprises no more than about 6% area under the curve when measured by HPLC of the compound of Formula (VII). In some embodiments, the compound of Formula (I), or a hydrate thereof, comprises no more than about 7% area under the curve when measured by HPLC of the compound of Formula (VII). In some embodiments, the compound of Formula (I), or a hydrate thereof, comprises no more than about 8% area under the curve when measured by HPLC of the compound of Formula (VII). In some embodiments, the compound of Formula (I), or a hydrate thereof, comprises no more than about 9% area under the curve when measured by HPLC of the compound of Formula (VII). In some embodiments, the compound of Formula (I), or a hydrate thereof, comprises no more than about 10% area under the curve when measured by HPLC of the compound of Formula (VII).

In some embodiments, the compound of Formula (I), or a hydrate thereof, comprises no more than about 0.05% to about 0.3% area under the curve when measured by HPLC of a compound of Formula (VIII)

(VIII)

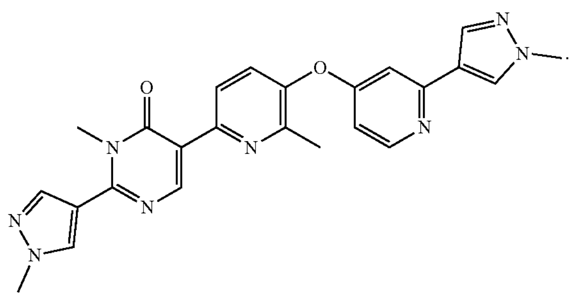

In some embodiments, the compound of Formula (I), or a hydrate thereof, comprises no more than about 0.1% to about 0.25% area under the curve when measured by HPLC of the compound of Formula (VIII). In some embodiments, the compound of Formula (I), or a hydrate thereof, comprises no more than about 0.1% to about 0.2% area under the curve when measured by HPLC of the compound of Formula (VIII). In some embodiments, the compound of Formula (I), or a hydrate thereof, comprises no more than about 0.1% to about 0.18% area under the curve when measured by HPLC of the compound of Formula (VIII). In some embodiments, the compound of Formula (I), or a hydrate thereof, comprises no more than about 0.1% to about 0.15% area under the curve when measured by HPLC of the compound of Formula (VIII).

In some embodiments, the compound of Formula (I), or a hydrate thereof, comprises no more than about 0.3% area under the curve when measured by HPLC of the compound of Formula (VIII). In some embodiments, the compound of Formula (I), or a hydrate thereof, comprises no more than about 0.25% area under the curve when measured by HPLC of the compound of Formula (VIII). In some embodiments, the compound of Formula (I), or a hydrate thereof, comprises no more than about 0.2% area under the curve when measured by HPLC of the compound of Formula (VIII). In some embodiments, the compound of Formula (I), or a hydrate thereof, comprises no more than about 0.18% area under the curve when measured by HPLC of the compound of Formula (VIII). In some embodiments, the compound of Formula (I), or a hydrate thereof, comprises no more than about 0.15% area under the curve when measured by HPLC of the compound of Formula (VIII). In some embodiments, the compound of Formula (I), or a hydrate thereof, comprises no more than about 0.12% area under the curve when measured by HPLC of the compound of Formula (VIII). In some embodiments, the compound of Formula (I), or a hydrate thereof, comprises no more than about 0.1% area under the curve when measured by HPLC of the compound of Formula (VIII). In some embodiments, the compound of Formula (I), or a hydrate thereof, comprises no more than about 0.07% area under the curve when measured by HPLC of the compound of Formula (VIII). In some embodiments, the compound of Formula (I), or a hydrate thereof, comprises no more than about 0.05% area under the curve when measured by HPLC of the compound of Formula (VIII).

In some embodiments, the compound of Formula (I), or a hydrate thereof, comprises no more than about 0.4% area under the curve when measured by HPLC of the compound of Formula (VIII). In some embodiments, the compound of Formula (I), or a hydrate thereof, comprises no more than about 0.5% area under the curve when measured by HPLC of the compound of Formula (VIII). In some embodiments, the compound of Formula (I), or a hydrate thereof, comprises no more than about 0.6% area under the curve when measured by HPLC of the compound of Formula (VIII). In some embodiments, the compound of Formula (I), or a hydrate thereof, comprises no more than about 0.7% area under the curve when measured by HPLC of the compound of Formula (VIII). In some embodiments, the compound of Formula (I), or a hydrate thereof, comprises no more than about 0.8% area under the curve when measured by HPLC of the compound of Formula (VIII). In some embodiments, the compound of Formula (I), or a hydrate thereof, comprises no more than about 0.9% area under the curve when measured by HPLC of the compound of Formula (VIII). In some embodiments, the compound of Formula (I), or a hydrate thereof, comprises no more than about 1% area under the curve when measured by HPLC of the compound of Formula (VIII). In some embodiments, the compound of Formula (I), or a hydrate thereof, comprises no more than about 2% area under the curve when measured by HPLC of the compound of Formula (VIII). In some embodiments, the compound of Formula (I), or a hydrate thereof, comprises no more than about 3% area under the curve when measured by HPLC of the compound of Formula (VIII). In some embodiments, the compound of Formula (I), or a hydrate thereof, comprises no more than about 4% area under the curve when measured by HPLC of the compound of Formula (VIII). In some embodiments, the compound of Formula (I), or a hydrate thereof, comprises no more than about 5% area under the curve when measured by HPLC of the compound of Formula (VIII). In some embodiments, the compound of Formula (I), or a hydrate thereof, comprises no more than about 6% area under the curve when measured by HPLC of the compound of Formula (VIII). In some embodiments, the compound of Formula (I), or a hydrate thereof, comprises no more than about 7% area under the curve when measured by HPLC of the compound of Formula (VIII). In some embodiments, the compound of Formula (I), or a hydrate thereof, comprises no more than about 8% area under the curve when measured by HPLC of the compound of Formula (VIII). In some embodiments, the compound of Formula (I), or a hydrate thereof, comprises no more than about 9% area under the curve when measured by HPLC of the compound of Formula (VIII). In some embodiments, the compound of Formula (I), or a hydrate thereof, comprises no more than about 10% area under the curve when measured by HPLC of the compound of Formula (VIII).

In some embodiments, the compound of Formula (I), or a hydrate thereof, comprises no more than about 0.05% to about 0.3% area under the curve when measured by HPLC of a compound of Formula (IX)

(IX)

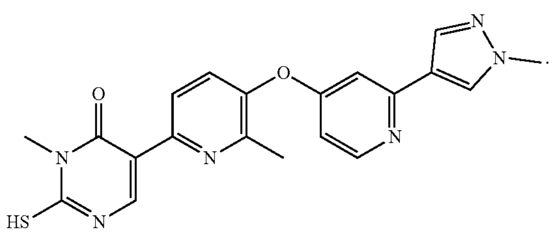

In some embodiments, the compound of Formula (I), or a hydrate thereof, comprises no more than about 0.1% to about 0.25% area under the curve when measured by HPLC of the compound of Formula (IX). In some embodiments, the compound of Formula (I), or a hydrate thereof, comprises no more than about 0.1% to about 0.2% area under the curve when measured by HPLC of the compound of Formula (IX). In some embodiments, the compound of Formula (I), or a hydrate thereof, comprises no more than about 0.1% to about 0.18% area under the curve when measured by HPLC of the compound of Formula (IX). In some embodiments, the compound of Formula (I), or a hydrate thereof, comprises no more than about 0.1% to about 0.15% area under the curve when measured by HPLC of the compound of Formula (IX).

In some embodiments, the compound of Formula (I), or a hydrate thereof, comprises no more than about 0.3% area under the curve when measured by HPLC of the compound of Formula (IX). In some embodiments, the compound of Formula (I), or a hydrate thereof, comprises no more than about 0.25% area under the curve when measured by HPLC of the compound of Formula (IX). In some embodiments, the compound of Formula (I), or a hydrate thereof, comprises no more than about 0.2% area under the curve when measured by HPLC of the compound of Formula (IX). In some embodiments, the compound of Formula (I), or a hydrate thereof, comprises no more than about 0.18% area under the curve when measured by HPLC of the compound of Formula (IX). In some embodiments, the compound of Formula (I), or a hydrate thereof, comprises no more than about 0.15% area under the curve when measured by HPLC of the compound of Formula (IX). In some embodiments, the compound of Formula (I), or a hydrate thereof, comprises no more than about 0.13% area under the curve when measured by HPLC of the compound of Formula (IX). In some embodiments, the compound of Formula (I), or a hydrate thereof, comprises no more than about 0.1% area under the curve when measured by HPLC of the compound of Formula (IX). In some embodiments, the compound of Formula (I), or a hydrate thereof, comprises no more than about 0.07% area under the curve when measured by HPLC of the compound of Formula (IX). In some embodiments, the compound of Formula (I), or a hydrate thereof, comprises no more than about 0.05% area under the curve when measured by HPLC of the compound of Formula (IX).

In some embodiments, the compound of Formula (I), or a hydrate thereof, comprises no more than about 0.4% area under the curve when measured by HPLC of the compound of Formula (IX). In some embodiments, the compound of Formula (I), or a hydrate thereof, comprises no more than about 0.5% area under the curve when measured by HPLC of the compound of Formula (IX). In some embodiments, the compound of Formula (I), or a hydrate thereof, comprises no more than about 0.6% area under the curve when measured by HPLC of the compound of Formula (IX). In some embodiments, the compound of Formula (I), or a hydrate thereof, comprises no more than about 0.7% area under the curve when measured by HPLC of the compound of Formula (IX). In some embodiments, the compound of Formula (I), or a hydrate thereof, comprises no more than about 0.8% area under the curve when measured by HPLC of the compound of Formula (IX). In some embodiments, the compound of Formula (I), or a hydrate thereof, comprises no more than about 0.9% area under the curve when measured by HPLC of the compound of Formula (IX). In some embodiments, the compound of Formula (I), or a hydrate thereof, comprises no more than about 1% area under the curve when measured by HPLC of the compound of Formula (IX). In some embodiments, the compound of Formula (I), or a hydrate thereof, comprises no more than about 2% area under the curve when measured by HPLC of the compound of Formula (IX). In some embodiments, the compound of Formula (I), or a hydrate thereof, comprises no more than about 3% area under the curve when measured by HPLC of the compound of Formula (IX). In some embodiments, the compound of Formula (I), or a hydrate thereof, comprises no more than about 4% area under the curve when measured by HPLC of the compound of Formula (IX). In some embodiments, the compound of Formula (I), or a hydrate thereof, comprises no more than about 5% area under the curve when measured by HPLC of the compound of Formula (IX). In some embodiments, the compound of Formula (I), or a hydrate thereof, comprises no more than about 6% area under the curve when measured by HPLC of the compound of Formula (IX). In some embodiments, the compound of Formula (I), or a hydrate thereof, comprises no more than about 7% area under the curve when measured by HPLC of the compound of Formula (IX). In some embodiments, the compound of Formula (I), or a hydrate thereof, comprises no more than about 8% area under the curve when measured by HPLC of the compound of Formula (IX). In some embodiments, the compound of Formula (I), or a hydrate thereof, comprises no more than about 9% area under the curve when measured by HPLC of the compound of Formula (IX). In some embodiments, the compound of Formula (I), or a hydrate thereof, comprises no more than about 10% area under the curve when measured by HPLC of the compound of Formula (IX).

Provided herein, in some embodiments, are compositions comprising a compound of Formula (I)

(I)

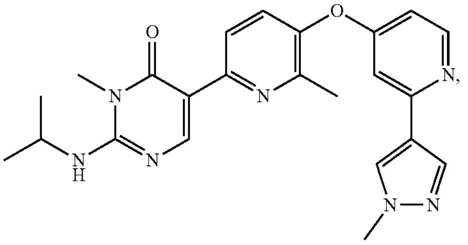

or a hydrate thereof, having a purity of greater than or equal to about 95% area under the curve when measured by HPLC, and one or more impurities, wherein the one or more impurities are present in the composition at no more than about 5% area under the curve when measured by HPLC.

In some embodiments, the compound of Formula (I), or a hydrate thereof, is characterized by a purity of greater than or equal to about 96% area under the curve when measured by HPLC. In some embodiments, the compound of Formula (I), or a hydrate thereof, is characterized by a purity of greater than or equal to about 97% area under the curve when measured by HPLC. In some embodiments, the compound of Formula (I), or a hydrate thereof, is characterized by a purity of greater than or equal to about 98% area under the curve when measured by HPLC. In some embodiments, the compound of Formula (I), or a hydrate thereof, is characterized by a purity of greater than or equal to about 99% area under the curve when measured by HPLC.

In some embodiments, the one or more impurities are present in the composition at no more than about 4.5% area under the curve when measured by HPLC. In some embodiments, the one or more impurities are present in the composition at no more than about 4% area under the curve when measured by HPLC. In some embodiments, the one or more impurities are present in the composition at no more than about 3.5% area under the curve when measured by HPLC. In some embodiments, the one or more impurities are present in the composition at no more than about 3% area under the curve when measured by HPLC. In some embodiments, the one or more impurities are present in the composition at no more than about 2.5% area under the curve when measured by HPLC. In some embodiments, the one or more impurities are present in the composition at no more than about 2% area under the curve when measured by HPLC. In some embodiments, the one or more impurities are present in the composition at no more than about 1.5% area under the curve when measured by HPLC. In some embodiments, the one or more impurities are present in the composition at no more than about 1% area under the curve when measured by HPLC. In some embodiments, the one or more impurities are present in the composition at no more than about 0.5% area under the curve when measured by HPLC.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

Provided herein, in some embodiments, are compositions consisting essentially of a compound of Formula (I)

(I)

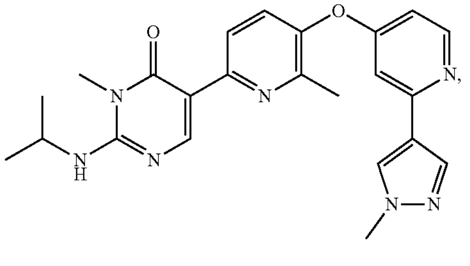

or a hydrate thereof, having a purity of greater than or equal to about 95% area under the curve when measured by HPLC, and one or more impurities, wherein the one or more impurities are present in the composition at no more than about 5% area under the curve when measured by HPLC.

In some embodiments, the compound of Formula (I), or a hydrate thereof, is characterized by a purity of greater than or equal to about 96% area under the curve when measured by HPLC. In some embodiments, the compound of Formula (I), or a hydrate thereof, is characterized by a purity of greater than or equal to about 97% area under the curve when measured by HPLC. In some embodiments, the compound of Formula (I), or a hydrate thereof, is characterized by a purity of greater than or equal to about 98% area under the curve when measured by HPLC. In some embodiments, the compound of Formula (I), or a hydrate thereof, is characterized by a purity of greater than or equal to about 99% area under the curve when measured by HPLC.

In some embodiments, the one or more impurities are present in the composition at no more than about 4.5% area under the curve when measured by HPLC. In some embodiments, the one or more impurities are present in the composition at no more than about 4% area under the curve when measured by HPLC. In some embodiments, the one or more impurities are present in the composition at no more than about 3.5% area under the curve when measured by HPLC. In some embodiments, the one or more impurities are present in the composition at no more than about 3% area under the curve when measured by HPLC. In some embodiments, the one or more impurities are present in the composition at no more than about 2.5% area under the curve when measured by HPLC. In some embodiments, the one or more impurities are present in the composition at no more than about 2% area under the curve when measured by HPLC. In some embodiments, the one or more impurities are present in the composition at no more than about 1.5% area under the curve when measured by HPLC. In some embodiments, the one or more impurities are present in the composition at no more than about 1% area under the curve when measured by HPLC. In some embodiments, the one or more impurities are present in the composition at no more than about 0.5% area under the curve when measured by HPLC.

In some embodiments, the compound of Formula (I), or a hydrate thereof, is characterized by a purity of greater than or equal to about 96% area under the curve when measured by HPLC. In some embodiments, the compound of Formula (I), or a hydrate thereof, is characterized by a purity of greater than or equal to about 97% area under the curve when measured by HPLC. In some embodiments, the compound of Formula (I), or a hydrate thereof, is characterized by a purity of greater than or equal to about 98% area under the curve when measured by HPLC. In some embodiments, the compound of Formula (I), or a hydrate thereof, is characterized by a purity of greater than or equal to about 99% area under the curve when measured by HPLC.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)$\cdot nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

Provided herein, in some embodiments, are compositions comprising a compound of Formula (I)

(I)

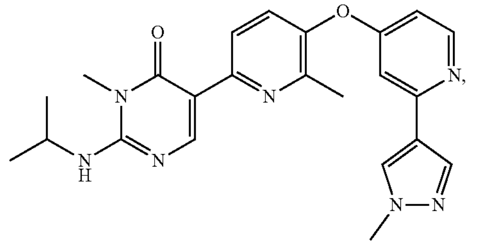

or a hydrate thereof, having greater than or about 95% purity, and one or more impurities, wherein the total amount of impurities is present in the composition at less than about 5% area under the curve when measured by HPLC.

In some embodiments, the compound of Formula (I), or a hydrate thereof, is characterized by a purity of greater than or equal to about 96% purity. In some embodiments, the compound of Formula (I), or a hydrate thereof, is characterized by a purity of greater than or equal to about 97% purity. In some embodiments, the compound of Formula (I), or a hydrate thereof, is characterized by a purity of greater than or equal to about 98% purity. In some embodiments, the compound of Formula (I), or a hydrate thereof, is characterized by a purity of greater than or equal to about 99% purity.

In some embodiments, the one or more impurities are present in the composition at no more than about 4.5% area under the curve when measured by HPLC. In some embodiments, the one or more impurities are present in the composition at no more than about 4% area under the curve when measured by HPLC. In some embodiments, the one or more impurities are present in the composition at no more than about 3.5% area under the curve when measured by HPLC. In some embodiments, the one or more impurities are present in the composition at no more than about 3% area under the curve when measured by HPLC. In some embodiments, the one or more impurities are present in the composition at no more than about 2.5% area under the curve when measured by HPLC. In some embodiments, the one or more more impurities are present in the composition at no more than about 2% area under the curve when measured by HPLC. In some embodiments, the one or more impurities are present in the composition at no more than about 1.5% area under the curve when measured by HPLC. In some embodiments, the one or more impurities are present in the composition at no more than about 1% area under the curve when measured by HPLC. In some embodiments, the one or more impurities are present in the composition at no more than about 0.5% area under the curve when measured by HPLC.

In some embodiments, the one or more impurities is any one of peaks 2-8 substantially as shown in Table 1.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

Provided herein, in some embodiments, are compositions consisting essentially of a compound of Formula (I)

(I)

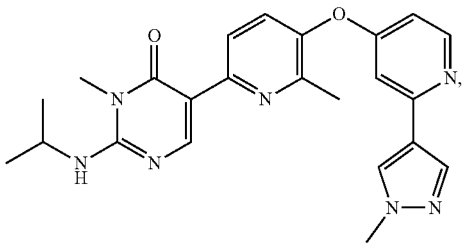

or a hydrate thereof, having greater than or about 95% purity, and one or more impurities, wherein the total amount of impurities is present in the composition at less than about 5% area under the curve when measured by HPLC.

In some embodiments, the one or more impurities are present in the composition at no more than about 4.5% area under the curve when measured by HPLC. In some embodiments, the one or more impurities are present in the composition at no more than about 4% area under the curve when measured by HPLC. In some embodiments, the one or more impurities are present in the composition at no more than about 3.5% area under the curve when measured by HPLC. In some embodiments, the one or more impurities are present in the composition at no more than about 3% area under the curve when measured by HPLC. In some embodiments, the one or more impurities are present in the composition at no more than about 2.5% area under the curve when measured by HPLC. In some embodiments, the one or more impurities are present in the composition at no more than about 2% area under the curve when measured by HPLC. In some embodiments, the one or more impurities are present in the composition at no more than about 1.5% area under the curve when measured by HPLC. In some embodiments, the one or more impurities are present in the composition at no more than about 1% area under the curve when measured by HPLC. In some embodiments, the one or more impurities are present in the composition at no more than about 0.5% area under the curve when measured by HPLC.

In some embodiments, the compound of Formula (I), or a hydrate thereof, is characterized by a purity of greater than or equal to about 96% purity. In some embodiments, the compound of Formula (I), or a hydrate thereof, is characterized by a purity of greater than or equal to about 97% purity. In some embodiments, the compound of Formula (I), or a hydrate thereof, is characterized by a purity of greater than or equal to about 98% purity. In some embodiments, the compound of Formula (I), or a hydrate thereof, is characterized by a purity of greater than or equal to about 99% purity.

In some embodiments, the one or more impurities is any one of peaks 2-8 substantially as shown in Table 1.

In some embodiments, the one or more impurities is selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof.

In some embodiments, the compound of Formula (I) is present in the pharmaceutically acceptable formulation as a hydrate form (the compound of Formula (I)·$nH_2O$), wherein the pharmaceutically acceptable formulation comprises one or more impurities selected from the group consisting of a compound of Formula (II), a compound of Formula (III), a compound of Formula (IV), a compound of Formula (V), a compound of Formula (VI), a compound of Formula (VII), a compound of Formula (VIII), and a compound of Formula (IX), or any combination thereof. For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

Pharmaceutical Compositions

In some embodiments, provided herein are pharmaceutical compositions comprising a compound of Formula (I), or a hydrate thereof, and a pharmaceutically acceptable carrier.

In some embodiments, provided herein are pharmaceutical compositions consisting essentially of a compound of Formula (I), or a hydrate thereof, and a pharmaceutically acceptable carrier.

In some embodiments, provided herein are pharmaceutical compositions comprising a compound of Formula (I), or a hydrate thereof, and a pharmaceutically acceptable carrier, wherein the compound of Formula (I), or a hydrate thereof, is present in the pharmaceutical composition in an amount to provide about 2 mg of the compound.

In some embodiments, provided herein are pharmaceutical compositions consisting essentially of a compound of Formula (I), or a hydrate thereof, and a pharmaceutically acceptable carrier, wherein the compound of Formula (I), or a hydrate thereof, is present in the pharmaceutical composition in an amount to provide about 2 mg of the compound.

In some embodiments, provided herein are pharmaceutical compositions comprising a compound of Formula (I), or a hydrate thereof, and a pharmaceutically acceptable carrier, wherein the compound of Formula (I), or a hydrate thereof, is present in the pharmaceutical composition in an amount to provide about 10 mg of the compound.

In some embodiments, provided herein are pharmaceutical compositions consisting essentially of a compound of Formula (I), or a hydrate thereof, and a pharmaceutically acceptable carrier, wherein the compound of Formula (I), or a hydrate thereof, is present in the pharmaceutical composition in an amount to provide about 10 mg of the compound.

In some embodiments, provided herein are pharmaceutical compositions comprising a compound of Formula (I), or a hydrate thereof, and a pharmaceutically acceptable carrier, wherein the compound of Formula (I), or a hydrate thereof, is present in the pharmaceutical composition in an amount to provide about 14 mg of the compound.

In some embodiments, provided herein are pharmaceutical compositions consisting essentially of a compound of Formula (I), or a hydrate thereof, and a pharmaceutically acceptable carrier, wherein the compound of Formula (I), or a hydrate thereof, is present in the pharmaceutical composition in an amount to provide about 14 mg of the compound.

In some embodiments, provided herein are pharmaceutical compositions comprising a compound of Formula (I), or a hydrate thereof, and a pharmaceutically acceptable carrier, wherein the compound of Formula (I), or a hydrate thereof, is present in the pharmaceutical composition in an amount to provide about 20 mg of the compound.

In some embodiments, provided herein are pharmaceutical compositions consisting essentially of a compound of Formula (I), or a hydrate thereof, and a pharmaceutically acceptable carrier, wherein the compound of Formula (I), or a hydrate thereof, is present in the pharmaceutical composition in an amount to provide about 20 mg of the compound.

In some embodiments, provided herein are pharmaceutical compositions comprising a compound of Formula (I), or a hydrate thereof, and a pharmaceutically acceptable carrier, wherein the compound of Formula (I), or a hydrate thereof, is present in the pharmaceutical composition in an amount to provide about 30 mg of the compound.

In some embodiments, provided herein are pharmaceutical compositions consisting essentially of a compound of Formula (I), or a hydrate thereof, and a pharmaceutically acceptable carrier, wherein the compound of Formula (I), or a hydrate thereof, is present in the pharmaceutical composition in an amount to provide about 30 mg of the compound.

In some embodiments, provided herein are oral dosage forms comprising a compound of Formula (I), or a hydrate thereof, and a pharmaceutically acceptable carrier.

In some embodiments, provided herein are oral dosage forms consisting essentially of a compound of Formula (I), or a hydrate thereof, and a pharmaceutically acceptable carrier.

In some embodiments, the oral dosage form is a tablet or a capsule. In some embodiments, the oral dosage form is a capsule. In some embodiments, the oral dosage form is a tablet.

The pharmaceutical compositions provided herein can contain one or more fillers, which are added, for example, to increase the bulk weight of the blend resulting in a practical size for encapsulation or compression. Fillers that may be used include, but are not limited to, calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc.

A disintegrant may be present in an amount necessary to expedite dissolution (e.g., increase the rate of tablet or capsule disintegration). The term "disintegrant" as used herein refers to an excipient which can oppose the physical forces of particle bonding in a tablet or capsule when the oral formulation is placed in an aqueous environment. Disintegrants include, but are not limited to, sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharide.

The pharmaceutical compositions can also include a lubricant. The term "lubricant" as used herein is typically added to prevent the tablet or capsule materials from sticking to punches or pins, minimize friction during tablet compression or encapsulation, and to allow for removal of the compressed tablet from the die or improve flowability of blends in capsules for improved processing properties. Examples of lubricants include, but are not limited to, colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogentated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate.

Flavoring agents and flavor enhancers may also be added for the dosage form to be more palatable to the patient. Common flavoring agents and flavor enhancers for pharmaceutical products that can be included in the formulation of the present disclosure include maltol, vanillin, ethyl vanillin, menthol, citric acid, fumaric acid, ethyl maltol, and tartaric acid.

Solid and liquid formulations can also be dyed using any pharmaceutically acceptable colorant to improve their appearance and/or facilitate patient identification of the product and unit dosage level.

In liquid formulations of the present disclosure, the active ingredient and any other solid excipients may be dissolved or suspended in a liquid carrier such as water, vegetable oil, alcohol, polyethylene glycol, propylene glycol, or glycerin.

Liquid formulations can contain emulsifying agents to disperse uniformly throughout the formulation an active ingredient or other excipient that is not soluble in the liquid carrier. Emulsifying agents that can be useful in liquid formulations of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid formulations of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid formulation can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid formulations of the present disclosure include powders, granulates, aggregates, and compacted formulations. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present disclosure is oral.

Diluents increase the bulk of a solid formulation and can make a pharmaceutical dosage form containing the formulation easier for the patient and caregiver to handle. Diluents for solid formulations include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid formulations that are compacted into a dosage form, such as a tablet, can include excipients whose functions include helping to bind the active ingredient and other excipients together after compression. Binders for solid formulations include acacia, alginic acid, carbomer (e.g., Carbopol), carboxymethylcellulose sodium, dextrin, ethyl cellulose, gelatin, guar gum, hydrogenated vegetable oil, hydroxyethyl cellulose, hydroxypropyl cellulose (e.g., Klucel®), hydroxypropyl methyl cellulose (e.g., Methocel®), liquid glucose, magnesium aluminum silicate, maltodextrin, methylcellulose, polymethacrylates, povidone (e.g., Kollidon®, Plasdone®), pregelatinized starch, sodium alginate, and starch.

The dissolution rate of a compacted solid formulation in the patient's stomach can be increased by the addition of a disintegrant to the formulation. Disintegrants include alginic acid, carboxymethylcellulose calcium, carboxymethylcellulose sodium (e.g., Ac-Di-Sol®, Primellose®), colloidal silicon dioxide, croscarmellose sodium, Crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid formulation and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered formulation, the formulation is subjected to pressure from a punch and dye. Some excipients and active ingredients tend to adhere to the surfaces of the punch and dye, which can cause the product to have pitting and other surface irregularities. A lubricant can be added to the formulation to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

A formulation for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting formulation can be prepared conventionally by dry blending. For example, the blended formulation of the actives and excipients can be compacted into a slug or a sheet and then comminuted into compacted granules. The compacted granules can subsequently be compressed into a tablet.

As an alternative to dry granulation, a blended formulation can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

Dosage forms include solid dosage forms like tablets, powders, capsules, suppositories, sachets, troches, and lozenges, as well as liquid syrups, suspensions, and elixirs.

The dosage form of the present disclosure can be a capsule containing the formulation, such as a powdered or granulated solid formulation of the disclosure, within either a hard or soft shell. The shell can be made from gelatin and optionally contain a plasticizer such as glycerin and sorbitol, and an opacifying agent or colorant.

In further embodiments, a pharmaceutical formulation of the compound represented by Formula (I) is formulated for administration to a mammal, such as a human. The compound represented by Formula (I) can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringe ability), fluidity, boiling point, miscibility, and purity. Suitable solvents include alcohol USP (United States Pharmacopeia), benzyl alcohol NF, benzyl benzoate USP, and Castor oil USP. Additional substances can be added to the formulation such as buffers, solubilizers, and antioxidants, among others. Ansel et al, Pharmaceutical Dosage Forms and Drug Delivery Systems, $7^{th}$ ed.

Methods of Use

Provided herein, in part, are methods for the treatment or prevention of a variety of diseases and disorders, which comprise administering to a patient in need of such treatment or prevention a therapeutically effective amount of a compound of Formula (I), or a hydrate thereof, a composition comprising a compound of Formula (I), or a hydrate thereof, or an oral dosage form comprising a compound of Formula (I), or a hydrate thereof.

In some embodiments, provided herein is a method of treating a tenosynovial giant cell tumor in a patient in need thereof, comprising administering to the patient a therapeutically effective amount of a compound of Formula (I), or a hydrate thereof, a therapeutically effective amount of a composition described herein, a therapeutically effective amount of a pharmaceutical composition described herein, or a therapeutically effective amount of an oral dosage form described herein.

In some embodiments, the tenosynovial giant cell tumor is a diffuse-type tenosynovial giant cell tumor.

In some embodiments, the tenosynovial giant cell tumor is a localized tenosynovial giant cell tumor.

In some embodiments, provided herein is a method of treating graft versus host disease (GVHD) in a patient in need thereof, comprising administering to the patient a therapeutically effective amount of a compound of Formula (I), or a hydrate thereof, a therapeutically effective amount of a composition described herein, a therapeutically effective amount of a pharmaceutical composition described herein, or a therapeutically effective amount of an oral dosage form described herein.

In some embodiments, the graft versus host disease is chronic graft versus host disease (cGVHD).

In some embodiments, the graft versus host disease is acute graft versus host disease (aGVHD).

In some embodiments, provided herein is a method of treating a neurodegenerative disease or condition in a patient in need thereof, comprising administering to the patient a therapeutically effective amount of a compound of Formula (I), or a hydrate thereof, a therapeutically effective amount of a composition described herein, a therapeutically effective amount of a pharmaceutical composition described herein, or a therapeutically effective amount of an oral dosage form described herein.

In some embodiments, the neurodegenerative disease condition is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof, comprising administering to the patient a therapeutically effective amount of a compound of Formula (I), or a hydrate thereof, a therapeutically effective amount of a composition described herein, a therapeutically effective amount of a pharmaceutical composition described herein, or a therapeutically effective amount of an oral dosage form described herein.

In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, the solid tumor has progressed after prior administration of another cancer therapy.

Also provided herein, in some embodiments, is a method of treating tumors known to have expression of colony-stimulating factor 1 receptor (CSF-1R) or its ligands, colony stimulating factor-1 (CSF-1), or interleukin (IL)-34 (IL-34), in a patient in need thereof, comprising administering to the patient a therapeutically effective amount of a compound of Formula (I), or a hydrate thereof, a therapeutically effective amount of a composition described herein, a therapeutically effective amount of a pharmaceutical composition described herein, or a therapeutically effective amount of an oral dosage form described herein.

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, in a patient in need thereof, comprising administering to the patient a therapeutically effective amount of a compound of Formula (I), or a hydrate thereof, a therapeutically effective amount of a composition described herein, a therapeutically effective amount of a pharmaceutical composition described herein, or a therapeutically effective amount of an oral dosage form described herein.

In some embodiments, the methods described herein further comprise administering to the patient a therapeutically effective amount of one or more additional therapeutic agents.

In some embodiments, the methods described herein further comprise administering to the patient a therapeutically effective amount of one or more additional therapeutic agents wherein the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet Alight, sirolimus, rituximab, methylprednisolone, budesonide, thalidomide, halofuginone, and hydroxychloroquine.

In some embodiments, the one or more additional therapeutic agents is belumosudil.

In some embodiments, the methods described herein further comprise administering an immunomodulatory therapeutic.

In some embodiments, the methods described herein further comprise administering a chemotherapeutic agent.

In some embodiments, the methods described herein further comprise administering an immunomodulatory therapeutic and a chemotherapeutic agent.

In some embodiments, the compound of Formula (I), or a hydrate thereof, the composition described herein, the composition described herein, or the pharmaceutical composition described herein, is administered orally.

In some embodiments, provided herein is a compound of Formula (I), or a hydrate thereof, a composition disclosed herein, a pharmaceutical composition disclosed herein, or oral dosage form disclosed herein, for use in treating a tenosynovial giant cell tumor in a patient in need thereof.

In some embodiments, provided herein is a compound of Formula (I), or hydrate thereof, composition, pharmaceutical composition, or oral dosage form for use disclosed herein, wherein the tenosynovial giant cell tumor is a diffuse-type tenosynovial giant cell tumor.

In some embodiments, provided herein is the compound of Formula (I) or hydrate thereof, composition, pharmaceutical composition, or oral dosage form for use disclosed herein, wherein the tenosynovial giant cell tumor is a localized tenosynovial giant cell tumor.

In some embodiments, provided herein is a compound of Formula (I), or a hydrate thereof, a composition disclosed herein, a pharmaceutical composition disclosed herein, or an oral dosage form disclosed herein, for use in treating graft versus host disease (GVHD) in a patient in need thereof.

In some embodiments, provided herein is the compound of Formula (I) or hydrate thereof, composition, pharmaceutical composition, or oral dosage form for use disclosed herein, wherein the graft versus host disease is chronic graft versus host disease (cGVHD).

In some embodiments, provided herein is the compound of Formula (I) or hydrate thereof, composition, pharmaceutical composition, or oral dosage form for use disclosed herein, wherein the graft versus host disease is acute graft versus host disease (aGVHD).

In some embodiments, provided herein is a compound of Formula (I), or a hydrate thereof, a composition disclosed herein, a pharmaceutical composition disclosed herein, or an oral dosage form disclosed herein, for use in treating a neurodegenerative disease or condition in a patient in need thereof.

In some embodiments, provided herein is the compound of Formula (I) or hydrate thereof, composition, pharmaceutical composition, or oral dosage form for use disclosed herein, wherein the neurodegenerative disease condition is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a compound of Formula (I), or a hydrate thereof, a composition disclosed herein, a pharmaceutical composition disclosed herein, or an oral dosage form disclosed herein, for use in treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof.

In some embodiments, provided herein is the compound of Formula (I) or hydrate thereof, composition, pharmaceutical composition, or oral dosage form for use disclosed herein, wherein the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is the compound of Formula (I) or hydrate thereof, composition, pharmaceutical composition, or oral dosage form for use disclosed herein, wherein the solid tumor has progressed after prior administration of another cancer therapy.

In some embodiments, provided herein is a compound of Formula (I), or a hydrate thereof, a composition disclosed herein, a pharmaceutical composition disclosed herein, or an oral dosage form disclosed herein, for use in treating tumors known to have expression of colony-stimulating factor 1 receptor (CSF-1R) or its ligands, colony stimulating factor-1 (CSF-1), or interleukin (IL)-34 (IL-34), in a patient in need thereof.

In some embodiments, provided herein is a compound of Formula (I), or a hydrate thereof, a composition disclosed herein, a pharmaceutical composition disclosed herein, or an oral dosage form disclosed herein, for use in treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, in a patient in need thereof.

In some embodiments, provided herein is the compound of Formula (I) or hydrate thereof, composition, pharmaceutical composition, or oral dosage form for use disclosed herein, further comprising administering to the patient a therapeutically effective amount of one or more additional therapeutic agents.

In some embodiments, provided herein is the compound of Formula (I) or hydrate thereof, composition, pharmaceutical composition, or oral dosage form for use disclosed herein, further comprising administering to the patient a therapeutically effective amount of one or more additional therapeutic agents wherein the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine.

In some embodiments, provided herein is the compound of Formula (I) or hydrate thereof, composition, pharmaceutical composition, or oral dosage form for use disclosed herein, wherein the one or more additional therapeutic agents is belumosudil.

In some embodiments, provided herein is the compound of Formula (I) or hydrate thereof, composition, pharmaceutical composition, or oral dosage form for use disclosed herein, further comprising administering an immunomodulatory therapeutic.

In some embodiments, provided herein is the compound of Formula (I) or hydrate thereof, composition, pharmaceutical composition, or oral dosage form for use disclosed herein, further comprising administering a chemotherapeutic agent.

In some embodiments, provided herein is the compound of Formula (I) or hydrate thereof, composition, pharmaceutical composition, or oral dosage form for use disclosed herein, further comprising administering an immunomodulatory therapeutic and a chemotherapeutic agent.

In some embodiments, provided herein is the compound of Formula (I) or hydrate thereof, composition, pharmaceutical composition, or oral dosage form for use disclosed herein, wherein the compound, or a hydrate thereof, the composition, or the pharmaceutical composition disclosed herein is administered orally.

In some embodiments, provided herein is the use of a compound of Formula (I), or a hydrate thereof, a composition disclosed herein, a pharmaceutical composition disclosed herein, or oral dosage form disclosed herein, in the manufacture of a medicament for treating a tenosynovial giant cell tumor in a patient in need thereof.

In some embodiments, provided herein is the use of a compound of Formula (I) or hydrate thereof, composition, pharmaceutical composition, or oral dosage form, in the manufacture of a medicament for treating a tenosynovial giant cell tumor in a patient in need thereof, wherein the tenosynovial giant cell tumor is a diffuse-type tenosynovial giant cell tumor.

In some embodiments, provided herein is the use of the compound of Formula (I) or hydrate thereof, composition, pharmaceutical composition, or oral dosage form, in the manufacture of a medicament for treating a tenosynovial giant cell tumor in a patient in need thereof, wherein the tenosynovial giant cell tumor is a localized tenosynovial giant cell tumor.

In some embodiments, provided herein is the use of a compound of Formula (I), or a hydrate thereof, a composition disclosed herein, a pharmaceutical composition disclosed herein, or an oral dosage form disclosed herein, in the manufacture of a medicament for treating graft versus host disease (GVHD) in a patient in need thereof.

In some embodiments, provided herein is the use of the compound of Formula (I) or hydrate thereof, composition, pharmaceutical composition, or oral dosage form, in the manufacture of a medicament for treating graft versus host disease (GVHD) in a patient in need thereof, wherein the graft versus host disease is chronic graft versus host disease (cGVHD).

In some embodiments, provided herein is the use of the compound of Formula (I) or hydrate thereof, composition, pharmaceutical composition, or oral dosage form, in the manufacture of a medicament for treating graft versus host disease (GVHD) in a patient in need thereof, wherein the graft versus host disease is acute graft versus host disease (aGVHD).

In some embodiments, provided herein is the use of a compound of Formula (I), or a hydrate thereof, a composition, a pharmaceutical composition, or an oral dosage form disclosed herein, in the manufacture of a medicament for treating a neurodegenerative disease or condition in a patient in need thereof.

In some embodiments, provided herein is the use of the compound of Formula (I) or hydrate thereof, composition, pharmaceutical composition, or oral dosage form, in the manufacture of a medicament for treating a neurodegenerative disease or condition in a patient in need thereof, wherein the neurodegenerative disease condition is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is the use of a compound of Formula (I), or a hydrate thereof, a composition, a pharmaceutical composition, or an oral dosage form disclosed herein, in the manufacture of a medicament for treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof.

In some embodiments, provided herein is the use of the compound of Formula (I) or hydrate thereof, composition, pharmaceutical composition, or oral dosage form disclosed herein, in the manufacture of a medicament for treating solid tumors, wherein the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is the use of the compound of Formula (I) or hydrate thereof, composition, pharmaceutical composition, or oral dosage form disclosed herein, in the manufacture of a medicament for treating solid tumors, wherein the solid tumor has progressed after prior administration of another cancer therapy.

In some embodiments, provided herein is the use of a compound of Formula (I), or a hydrate thereof, a composition, a pharmaceutical composition, or an oral dosage form disclosed herein, in the manufacture of a medicament for treating tumors known to have expression of colony-stimulating factor 1 receptor (CSF-1R) or its ligands, colony stimulating factor-1 (CSF-1), or interleukin (IL)-34 (IL-34), in a patient in need thereof.

In some embodiments, provided herein is the use of a compound of Formula (I), or a hydrate thereof, a composition, a pharmaceutical composition, or an oral dosage form disclosed herein, in the manufacture of a medicament for treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, in a patient in need thereof.

In some embodiments, provided herein is the use of the compound of Formula (I) or hydrate thereof, composition, pharmaceutical composition, or oral dosage form disclosed herein, in the manufacture of a medicament for treating diseases disclosed herein, further comprising administering to the patient a therapeutically effective amount of one or more additional therapeutic agents.

In some embodiments, provided herein is the use of the compound of Formula (I) or hydrate thereof, composition, pharmaceutical composition, or oral dosage form, in the manufacture of a medicament for treating diseases disclosed herein, further comprising administering to the patient a therapeutically effective amount of one or more additional therapeutic agents wherein the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine.

In some embodiments, provided herein is the use of the compound or hydrate thereof, composition, pharmaceutical composition, or oral dosage form, in the manufacture of a medicament for treating diseases disclosed herein, wherein the one or more additional therapeutic agents is belumosudil.

In some embodiments, provided herein is the use of the compound or hydrate thereof, composition, pharmaceutical composition, or oral dosage form, in the manufacture of a medicament for treating diseases disclosed herein, further comprising administering an immunomodulatory therapeutic.

In some embodiments, provided herein is the use of the compound or hydrate thereof, composition, pharmaceutical composition, or oral dosage form, in the manufacture of a medicament for treating diseases disclosed herein, further comprising administering a chemotherapeutic agent.

In some embodiments, provided herein is the use of the compound or hydrate thereof, composition, pharmaceutical composition, or oral dosage form, in the manufacture of a medicament for treating diseases disclosed herein, further comprising administering an immunomodulatory therapeutic and a chemotherapeutic agent.

In some embodiments, provided herein is the use of the compound or hydrate thereof, composition, pharmaceutical composition, or oral dosage form, in the manufacture of a medicament for treating diseases disclosed herein, wherein the compound of Formula (I) or a hydrate thereof, the composition, or the pharmaceutical composition disclosed herein, is administered orally.

In some embodiments, provided herein is a composition comprising a compound of Formula (I):

(I)

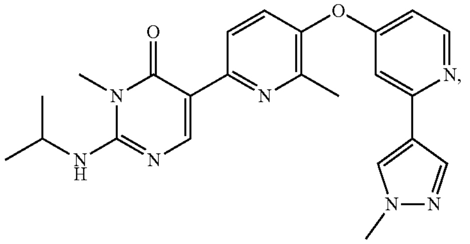

or a hydrate thereof, having a purity of greater than or equal to about 95% weight/weight of the composition, and a compound of Formula (II):

(II)

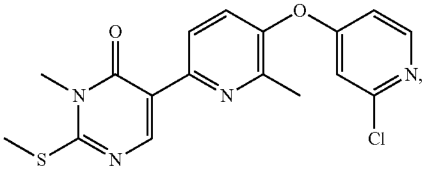

wherein the compound of Formula (II) is present in the composition at no more than about 5% weight/weight of the composition.

In some embodiments, provided herein is a composition consisting essentially of a compound of Formula (I):

(I)

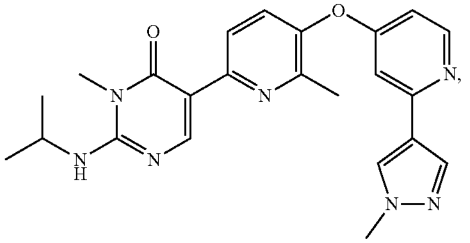

or a hydrate thereof, having a purity of greater than or equal to about 95% weight/weight of the composition, and a compound of Formula (II):

(II)

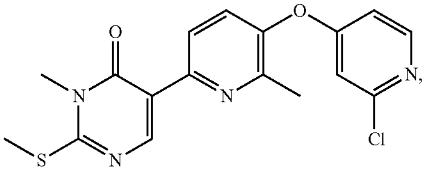

wherein the compound of Formula (II) is present in the composition at no more than about 5% weight/weight of the composition.

In some embodiments, provided herein is a composition comprising a compound of Formula (I):

(I)

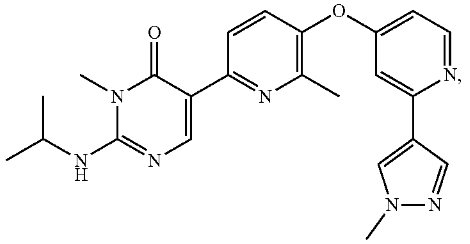

or a hydrate thereof, having a purity of greater than or equal to about 95% weight/weight of the composition, and a compound of Formula (II):

(II)

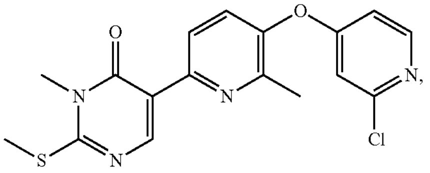

wherein the compound of Formula (II) is present in the composition at no more than about 300 ppm.

In some embodiments, provided herein is a composition consisting essentially of a compound of Formula (I):

(I)

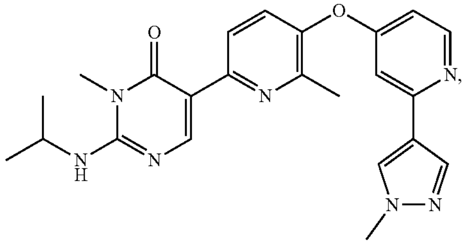

or a hydrate thereof, having a purity of greater than or equal to about 95% weight/weight of the composition, and a compound of Formula (II):

(II)

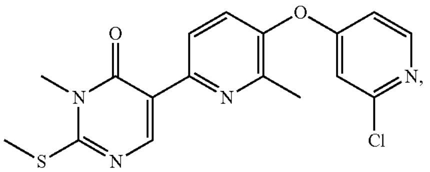

wherein the compound of Formula (II) is present in the composition at no more than about 300 ppm.

In some embodiments, provided herein is a composition comprising a compound of Formula (I):

(I)

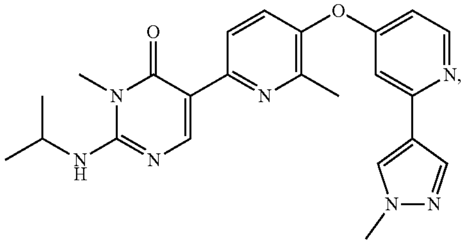

or a hydrate thereof, having a purity of greater than or equal to about 95% weight/weight of the composition, and a compound of Formula (III):

(III)

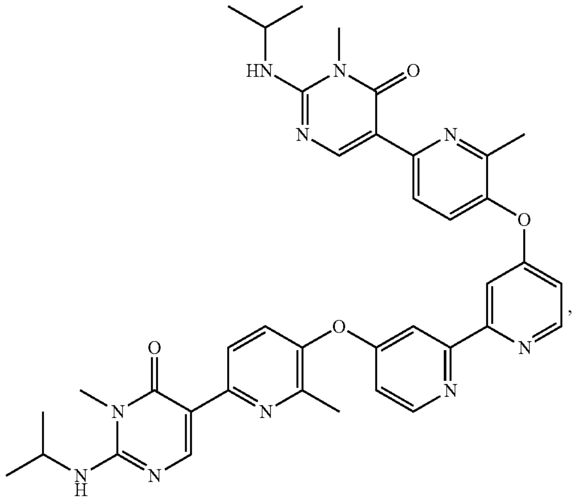

wherein the compound of Formula (III) is present in the composition at less than about 5% area under the curve when measured by HPLC.

In some embodiments, provided herein is a composition consisting essentially of a compound of Formula (I):

(I)

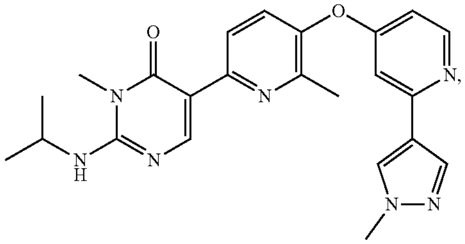

or a hydrate thereof, having a purity of greater than or equal to about 95% weight/weight of the composition, and a compound of Formula (III):

(III)

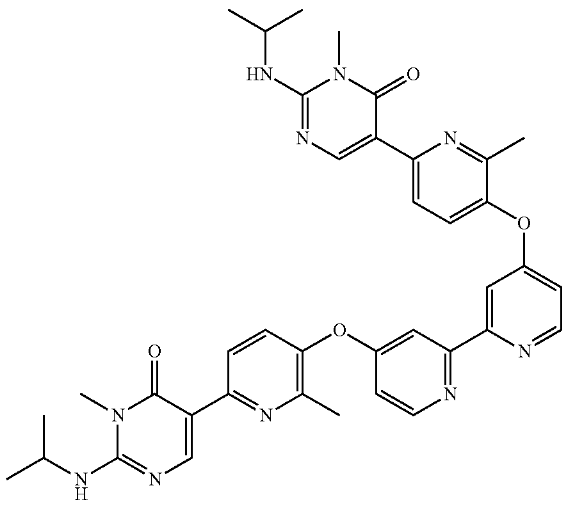

wherein the compound of Formula (III) is present in the composition at less than about 5% area under the curve when measured by HPLC.

In some embodiments, provided herein is a composition comprising a compound of Formula (I):

(I)

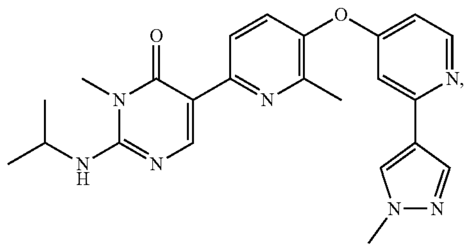

or a hydrate thereof, having a purity of greater than or equal to about 95% weight/weight of the composition, and a compound of Formula (IV):

(IV)

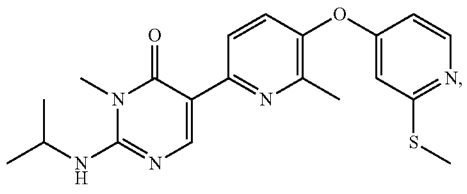

wherein the compound of Formula (IV) is present in the composition at less than about 5% area under the curve when measured by HPLC.

In some embodiments, provided herein is a composition consisting essentially of a compound of Formula (I):

(I)

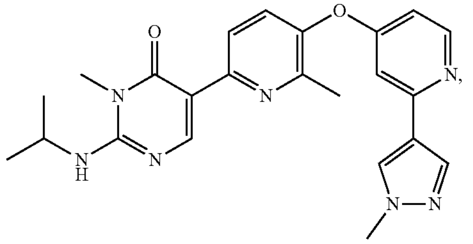

or a hydrate thereof, having a purity of greater than or equal to about 95% weight/weight of the composition, and a compound of Formula (IV):

(IV)

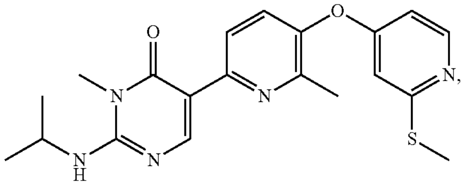

wherein the compound of Formula (IV) is present in the composition at less than about 5% area under the curve when measured by HPLC.

In some embodiments, provided herein is a composition comprising a compound of Formula (I):

(I)

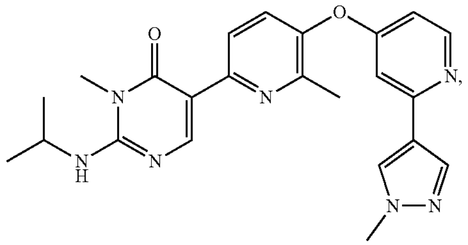

or a hydrate thereof, having a purity of greater than or equal to about 95% weight/weight of the composition, and a compound of Formula (V):

(V)

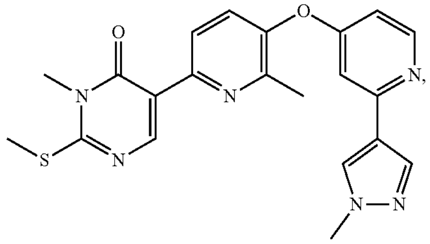

wherein the compound of Formula (V) is present in the composition at less than about 5% area under the curve when measured by HPLC.

In some embodiments, provided herein is a composition consisting essentially of a compound of Formula (I):

(I)

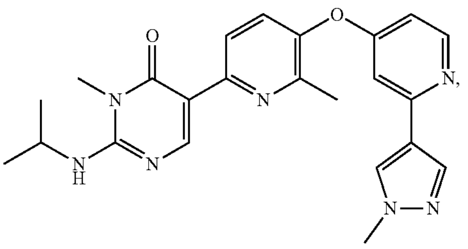

or a hydrate thereof, having a purity of greater than or equal to about 95% weight/weight of the composition, and a compound of Formula (V):

(V)

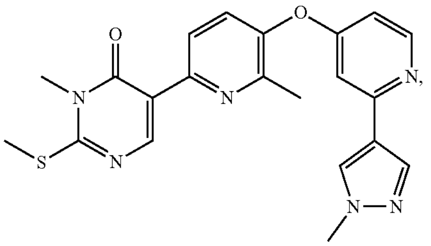

wherein the compound of Formula (V) is present in the composition at less than about 5% area under the curve when measured by HPLC.

In some embodiments, provided herein is a composition comprising a compound of Formula (I):

(I)

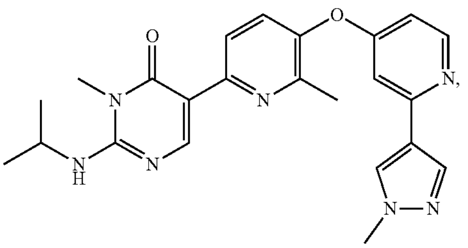

or a hydrate thereof, having a purity of greater than or equal to about 95% weight/weight of the composition, and a compound of Formula (VI):

(VI)

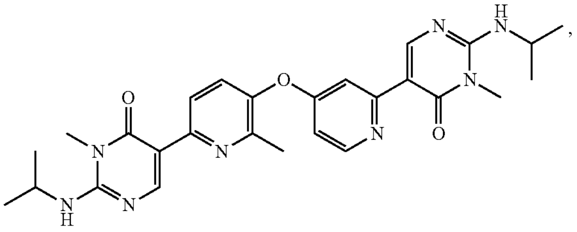

wherein the compound of Formula (VI) is present in the composition at less than about 5% area under the curve when measured by HPLC.

In some embodiments, provided herein is a composition consisting essentially of a compound of Formula (I):

(I)

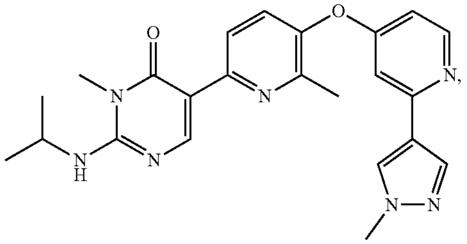

or a hydrate thereof, having a purity of greater than or equal to about 95% weight/weight of the composition, and a compound of Formula (VI):

(VI)

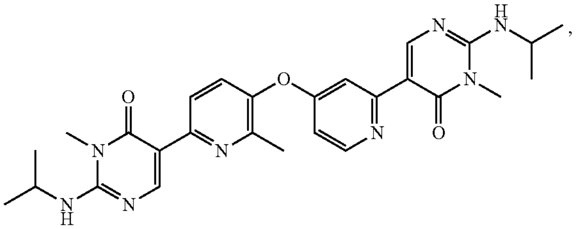

wherein the compound of Formula (VI) is present in the composition at less than about 5% area under the curve when measured by HPLC.

In some embodiments, provided herein is a composition comprising a compound of Formula (I):

(I)

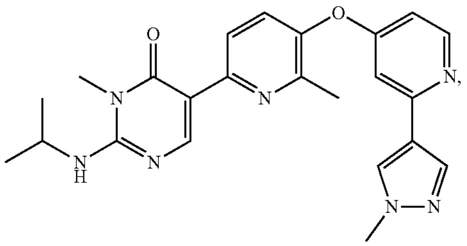

or a hydrate thereof, having a purity of greater than or equal to about 95% weight/weight of the composition, and a compound of Formula (VIII):

(VIII)

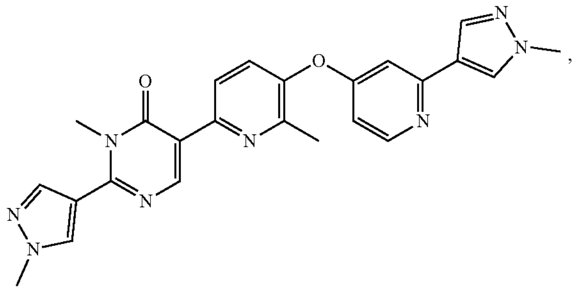

wherein the compound of Formula (VIII) is present in the composition at less than about 5% area under the curve when measured by HPLC.

In some embodiments, provided herein is a composition consisting essentially of a compound of Formula (I):

(I)

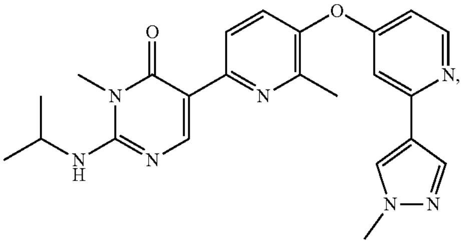

or a hydrate thereof, having a purity of greater than or equal to about 95% weight/weight of the composition, and a compound of Formula (VII):

(VIII)

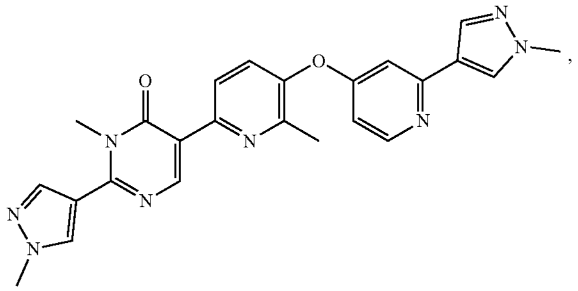

wherein the total amount of the compound of Formula (VIII) is present in the composition at less than about 5% area under the curve when measured by HPLC.

In some embodiments, provided herein is a composition comprising a compound of Formula (I):

(I)

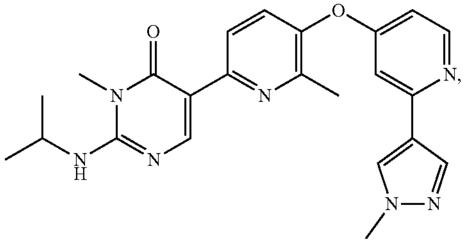

or a hydrate thereof, having a purity of greater than or equal to about 95% weight/weight of the composition, and a compound of Formula (IX):

(IX)

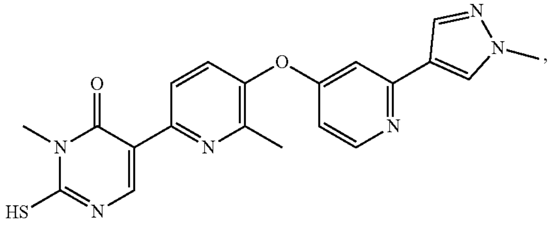

wherein the total amount of the compound of Formula (IX) is present in the composition at less than about 5% area under the curve when measured by HPLC.

In some embodiments, provided herein is a composition consisting essentially of a compound of Formula (I):

(I)

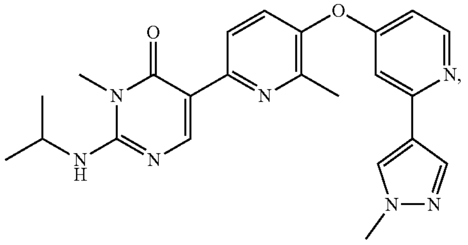

or a hydrate thereof, having a purity of greater than or equal to about 95% weight/weight of the composition, and a compound of Formula (IX):

(IX)

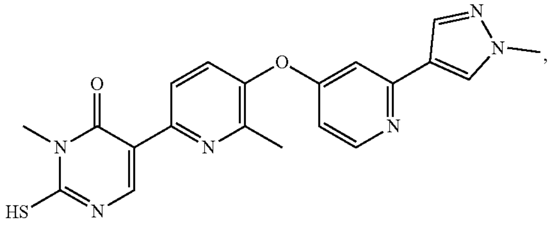

wherein the compound of Formula (IX) is present in the composition at less than about 5% area under the curve when measured by HPLC.

In some embodiments, provided herein is a composition comprising a compound of Formula (I):

(I)

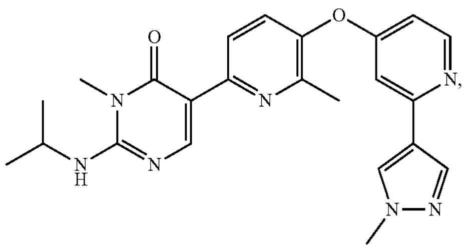

or a hydrate thereof, having greater than or about 95% purity, and one or more impurities, wherein the total amount of impurities is present in the composition at less than about 5% area under the curve when measured by HPLC;

and a means for preparing the compound of Formula (I).

In some embodiments, provided herein is a composition disclosed herein, wherein the one or more impurities is any one of peaks 2-8 substantially as shown in FIG. 1.

In some embodiments, provided herein is a composition consisting essentially of a compound of Formula (I):

(I)

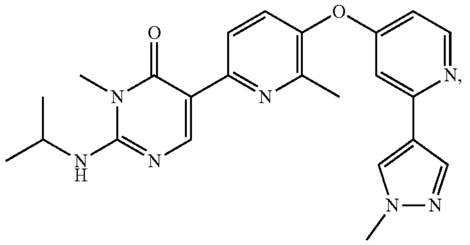

or a hydrate thereof, having greater than or about 95% purity, and one or more impurities, wherein the total amount of impurities is present in the composition at less than about 5% area under the curve when measured by HPLC;

and a means for preparing the compound of Formula (I).

In some embodiments, provided herein is a composition disclosed herein, wherein the one or more impurities is any one of peaks 2-8 substantially as shown in FIG. 1.

In some embodiments, provided herein is a composition disclosed herein, wherein the one or more impurities is selected from the group consisting of a compound of Formula (II), a compound of Formula (III), a compound of Formula (IV), a compound of Formula (V), a compound of Formula (VI), a compound of Formula (VIII), and a compound of Formula (IX), and any combination thereof.

In some embodiments, provided herein is a composition comprising a compound of Formula (I):

(I)

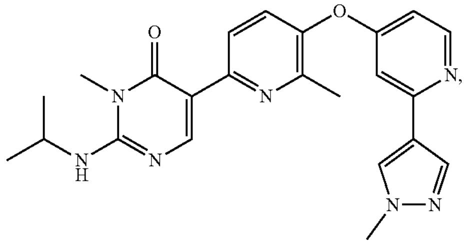

or a hydrate thereof, having a purity of greater than or equal to about 95% weight/weight of the composition, and a compound of Formula (II):

(II)

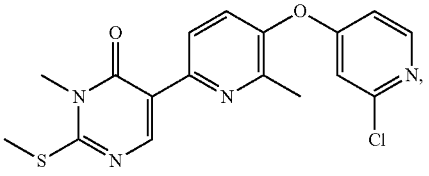

wherein the compound of Formula (II) is present in the composition at no more than about 5% weight/weight of the composition;

and a means for preparing the compound of Formula (I).

In some embodiments, provided herein is a composition consisting essentially of a compound of Formula (I):

(I)

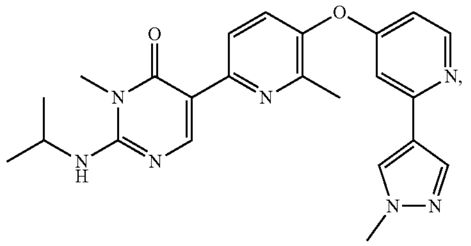

or a hydrate thereof, having a purity of greater than or equal to about 95% weight/weight of the composition, and a compound of Formula (II):

(II)

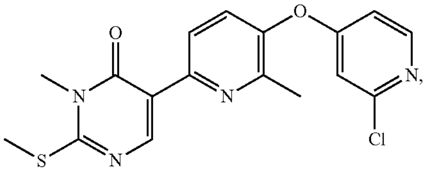

wherein the compound of Formula (II) is present in the composition at no more than about 5% weight/weight of the composition;

and a means for preparing the compound of Formula (I).

In some embodiments, provided herein is a composition comprising a compound of Formula (I):

(I)

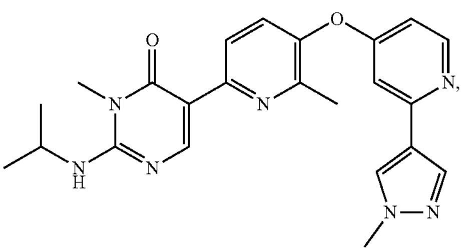

or a hydrate thereof, having a purity of greater than or equal to about 95% weight/weight of the composition, and a compound of Formula (II):

(II)

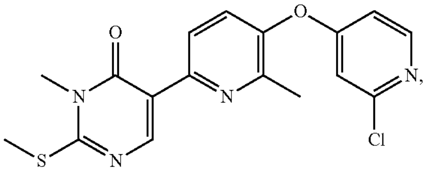

wherein the compound of Formula (II) is present in the composition at no more than about 50 ppm to about 1000 ppm;

and a means for preparing the compound of Formula (I).

In some embodiments, provided herein is a composition consisting essentially of a compound of Formula (I):

(I)

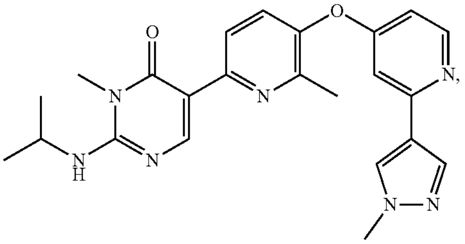

or a hydrate thereof, having a purity of greater than or equal to about 95% weight/weight of the composition, and a compound of Formula (II):

(II)

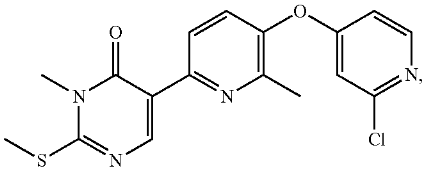

wherein the compound of Formula (II) is present in the composition at no more than about 50 ppm to about 1000 ppm;

and a means for preparing the compound of Formula (I).

In some embodiments, provided herein is a composition comprising a compound of Formula (I):

(I)

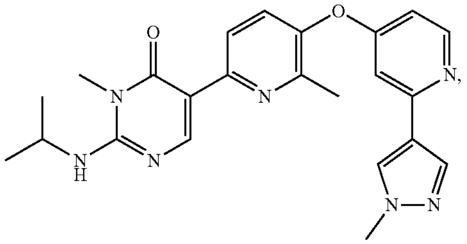

or a hydrate thereof, having a purity of greater than or equal to about 95% weight/weight of the composition, and a compound of Formula (II):

(II)

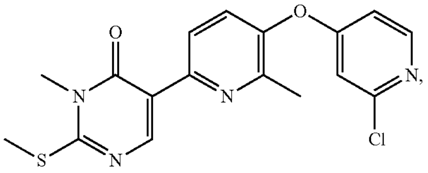

wherein the compound of Formula (II) is present in the composition at less than about 5% area under the curve when measured by HPLC;

and a means for preparing the compound of Formula (I).

In some embodiments, provided herein is a composition consisting essentially of a compound of Formula (I):

(I)

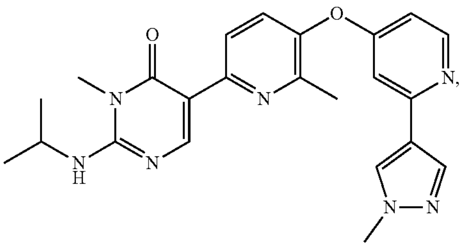

or a hydrate thereof, having a purity of greater than or equal to about 95% weight/weight of the composition, and a compound of Formula (II):

(II)

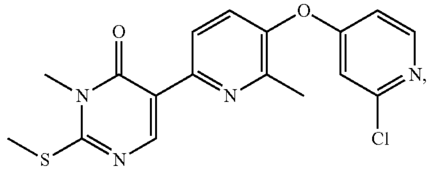

wherein the compound of Formula (II) is present in the composition at less than about 5% area under the curve when measured by HPLC;

and a means for preparing the compound of Formula (I).

In some embodiments, provided herein is a composition comprising a compound of Formula (I):

(I)

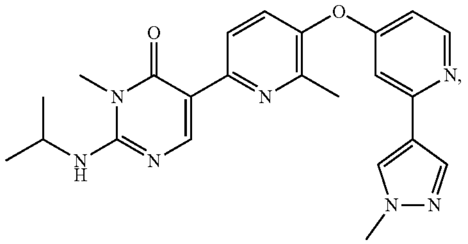

or a hydrate thereof, having a purity of greater than or equal to about 95% weight/weight of the composition, and a compound of Formula (III):

(III)

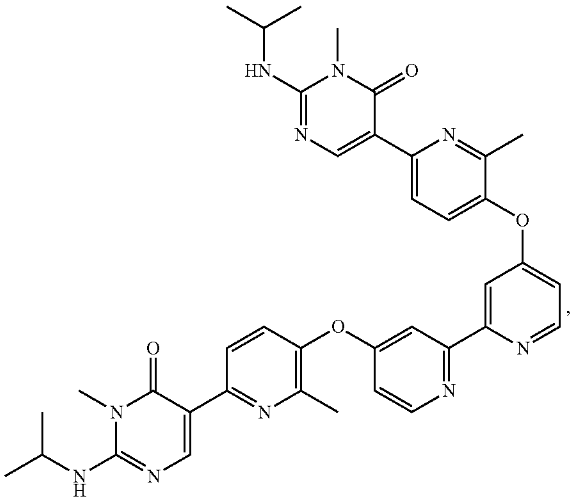

wherein the compound of Formula (III) is present in the composition at less than about 5% area under the curve when measured by HPLC;

and a means for preparing the compound of Formula (I).

In some embodiments, provided herein is a composition consisting essentially of a compound of Formula (I):

(I)

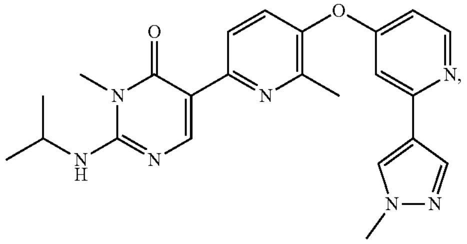

or a hydrate thereof, having a purity of greater than or equal to about 95% weight/weight of the composition, and a compound of Formula (III):

(III)

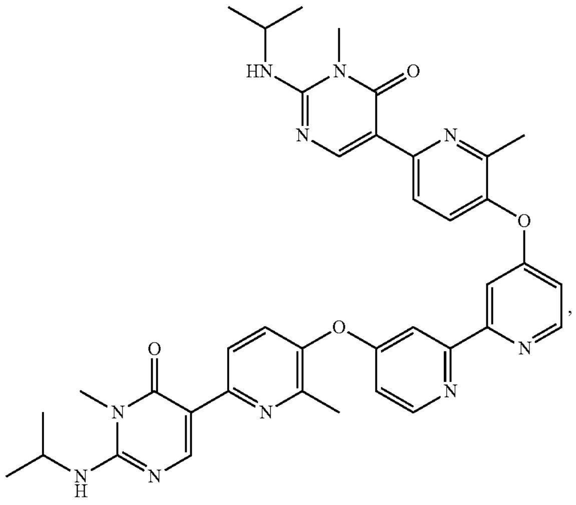

wherein the compound of Formula (III) is present in the composition at less than about 5% area under the curve when measured by HPLC;

and a means for preparing the compound of Formula (I).

In some embodiments, provided herein is a composition comprising a compound of Formula (I):

(I)

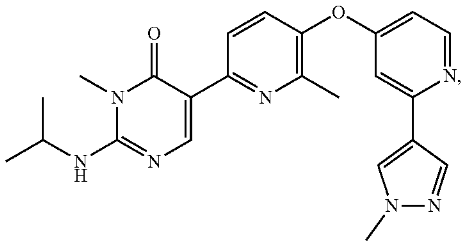

or a hydrate thereof, having a purity of greater than or equal to about 95% weight/weight of the composition, and a compound of Formula (IV):

(IV)

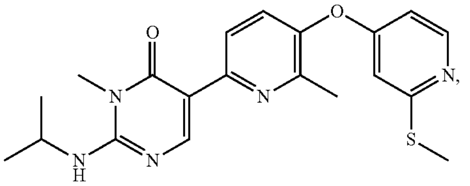 [SMILES: CSc1cc(Oc2ccc(-c3cnc(NC(C)C)n(C)c3=O)nc2C)ccn1]

wherein the compound of Formula (IV) is present in the composition at less than about 5% area under the curve when measured by HPLC;

and a means for preparing the compound of Formula (I).

In some embodiments, provided herein is a composition consisting essentially of a compound of Formula (I):

(I)

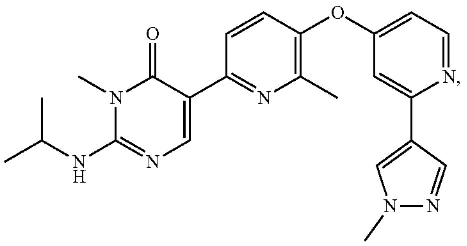

or a hydrate thereof, having a purity of greater than or equal to about 95% weight/weight of the composition, and a compound of Formula (IV):

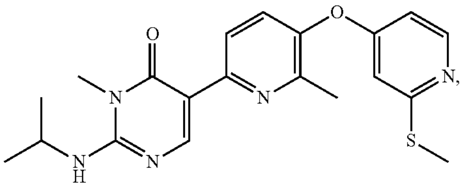

wherein the compound of Formula (IV) is present in the composition at less than about 5% area under the curve when measured by HPLC;

and a means for preparing the compound of Formula (I).

In some embodiments, provided herein is a composition comprising a compound of Formula (I):

(I)

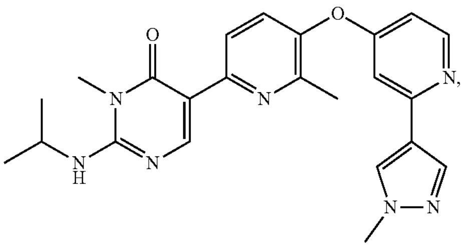

or a hydrate thereof, having a purity of greater than or equal to about 95% weight/weight of the composition, and a compound of Formula (V):

(V)

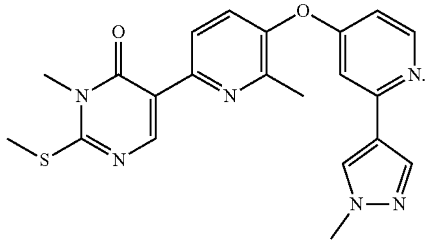

wherein the compound of Formula (V) is present in the composition at less than about 5% area under the curve when measured by HPLC;

and a means for preparing the compound of Formula (I).

In some embodiments, provided herein is a composition consisting essentially of a compound of Formula (I):

(I)

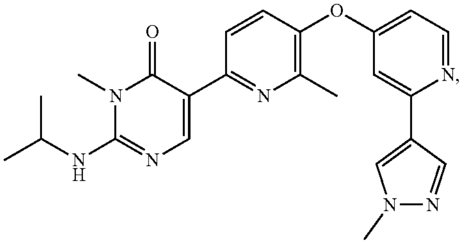

or a hydrate thereof, having a purity of greater than or equal to about 95% weight/weight of the composition, and a compound of Formula (V):

(V)

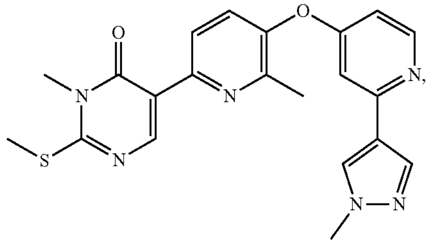

wherein the compound of Formula (V) is present in the composition at less than about 5% area under the curve when measured by HPLC;

and a means for preparing the compound of Formula (I).

In some embodiments, provided herein is a composition comprising a compound of Formula (I):

(I)

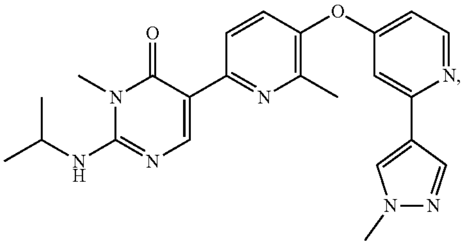

or a hydrate thereof, having a purity of greater than or equal to about 95% weight/weight of the composition, and a compound of Formula (VI):

(VI)

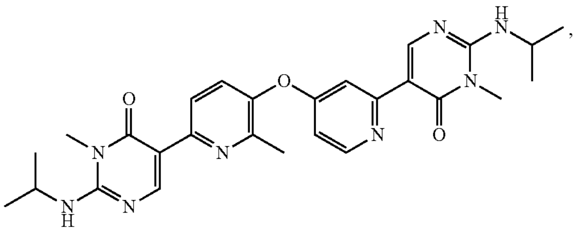

wherein the compound of Formula (VI) is present in the composition at less than about 5% area under the curve when measured by HPLC;

and a means for preparing the compound of Formula (I).

In some embodiments, provided herein is a composition consisting essentially of a compound of Formula (I):

(I)

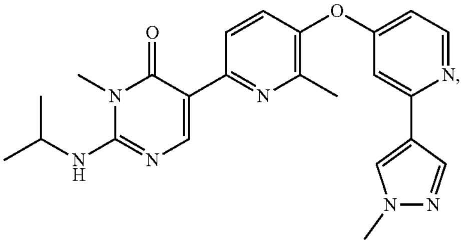

or a hydrate thereof, having a purity of greater than or equal to about 95% weight/weight of the composition, and a compound of Formula (VI):

(VI)

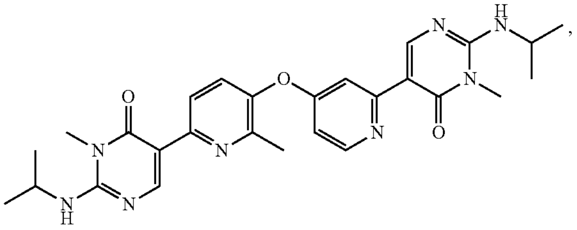

wherein the compound of Formula (VI) is present in the composition at less than about 5% area under the curve when measured by HPLC;

and a means for preparing the compound of Formula (I).

In some embodiments, provided herein is a composition comprising a compound of Formula (I):

(I)

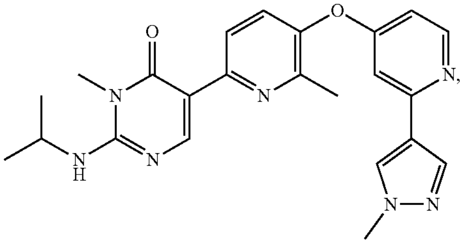

or a hydrate thereof, having a purity of greater than or equal to about 95% weight/weight of the composition, and a compound of Formula (VIII):

(VIII)

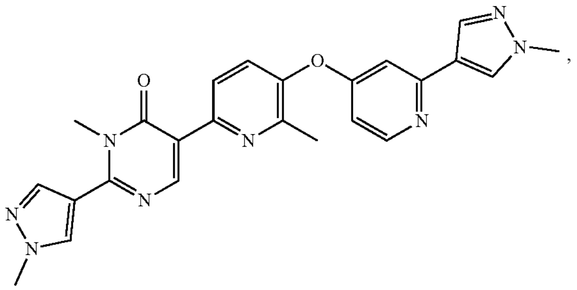

wherein the compound of Formula (VIII) is present in the composition at less than about 5% area under the curve when measured by HPLC;

and a means for preparing the compound of Formula (I).

In some embodiments, provided herein is a composition consisting essentially of a compound of Formula (I):

(I)

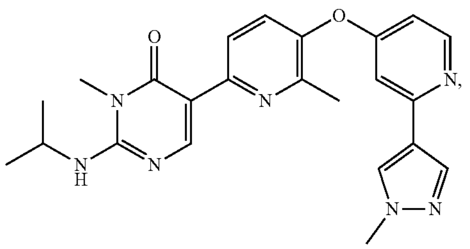

or a hydrate thereof, having a purity of greater than or equal to about 95% weight/weight of the composition, and a compound of Formula (VIII):

(VIII)

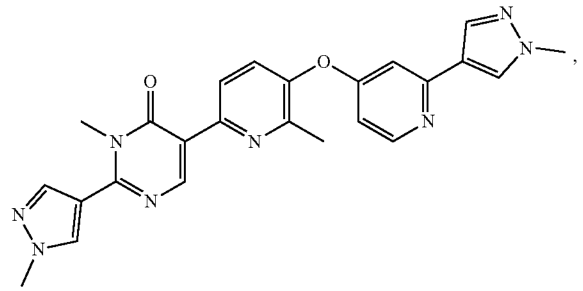

wherein the compound of Formula (VIII) is present in the composition at less than about 5% area under the curve when measured by HPLC;

and a means for preparing the compound of Formula (I).

In some embodiments, provided herein is a composition comprising a compound of Formula (I):

(I)

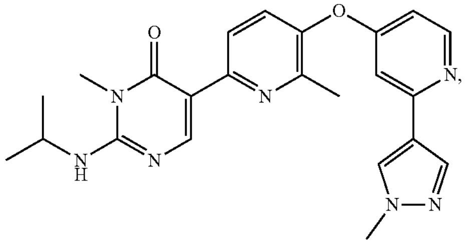

or a hydrate thereof, having a purity of greater than or equal to about 95% weight/weight of the composition, and a compound of Formula (IX):

(IX)

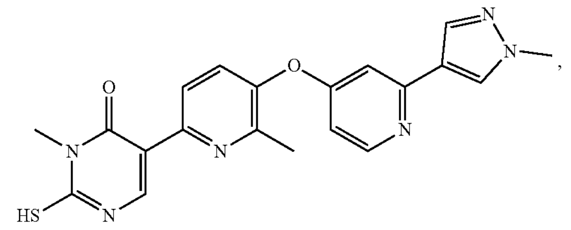

wherein the compound of Formula (IX) is present in the composition at less than about 5% area under the curve when measured by HPLC;

and a means for preparing the compound of Formula (I).

In some embodiments, provided herein is a composition consisting essentially of a compound of Formula (I):

(I)

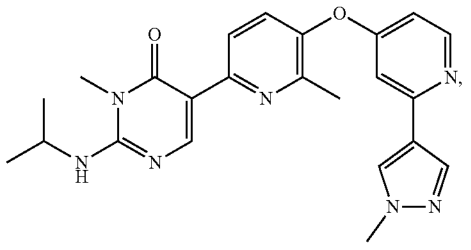

or a hydrate thereof, having a purity of greater than or equal to about 95% weight/weight of the composition, and a compound of Formula (IX):

(IX)

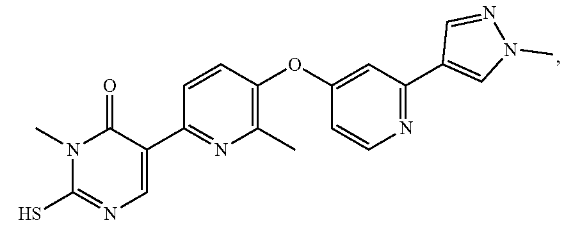

wherein the compound of Formula (IX) is present in the composition at less than about 5% area under the curve when measured by HPLC;

and a means for preparing the compound of Formula (I).

EXAMPLES

The present disclosure is not to be limited in scope by the specific embodiments disclosed in the examples which are intended as illustrations of a few aspects of the disclosure and any embodiments that are functionally equivalent are within the scope of this disclosure. Indeed, various modifications in addition to those shown and described herein will become apparent to those skilled in the art and are intended to fall within the scope of the appended claims.

The following abbreviations are used in this disclosure and have the following definitions: "ADP" is adenosine diphosphate, "AUC" is area under the curve, "$Cs_2CO_3$" is cesium carbonate, "conc." is concentrated, "DBN" is 1,5-diazabicyclo(4.3.0)non-5-ene, "DBU" is 1,8-diazabicyclo[5.4.0]undec-7-ene, "DCM" is dichloromethane, "DIEA" is N,N-diisopropylethylamine, "DMA" or "DMAc" or "DMAC" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphoryl azide, "ESI" is electrospray ionization, "$Et_2O$" is diethylether, "EtOAc" is ethyl acetate, "EtOH" is ethanol, "GST" is glutathione S-transferase, "h" is hour or hours, "Hex" is hexane, "$IC_{50}$" is half maximal inhibitory concentration, "$K_2CO_3$" is potassium carbonate, "LiMHDS" is lithium bis(trimethylsilyl) amide, "MeCN" is acetonitrile, "MeOH" is methanol, "MHz" is megahertz, "min" is minute or minutes, "MIBK" is methyl isobutyl ketone, "MS" is mass spectrometry, "MTBE" is methyl tert-butyl ether, "NADH" is nicotinamide adenine dinucleotide, "NBS" is N-bromosuccinimide, "NMP" is N-Methyl-2-pyrrolidone, "NMR" is nuclear magnetic resonance, "PBS" is phosphate buffered saline, "Pd/C" is palladium on carbon, "$Pd_2(dba)_3$" is tris(dibenzylideneacetone)dipalladium(0), "$Pd(PPh_3)_4$" is tetrakis(triphenylphosphine)palladium (0), "ppm" is parts per million, "prep-HPLC" is preparative high performance liquid chromatography, "room temperature" which is also known as "ambient temp," will be understood to consist of a range of normal laboratory temperatures ranging from 15-25° C., "RT" is retention time, "RRT" is relative retention time, "RRF" is relative response factor, "satd." is saturated, "sulfolane" is 1λ-Thiolane-1,1-dione, "t-BuOK" is potassium tert-butoxide, "TEA" is triethylamine, "TFA" is trifluoroacetic acid, "THF" is tetrahydrofuran, "Tris" is tris(hydroxymethyl)aminomethane, "SPhos" is dicyclohexyl(2',6'-dimethoxy[1,1'-bihenyl]-2-yl)phosphane, "Xantphos" is 4,5-bis(diphenylphosphino)-9,9-dimethylxanthene, and "X-Phos" is 2-dicyclohexylphosphino-2',4',6'-triisopropylbiphenyl.

Example 1. Exemplary Preparation of a Compound of Formula (I)

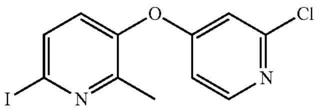 [SMILES: Cc1nc(I)ccc1Oc1ccnc(Cl)c1]

3-((2-chloropyridin-4-yl)oxy)-6-iodo-2-methylpyridine: 6-iodo-2-methylpyridin-3-ol (1.00 kg), 2-chloro-4-fluoropyridine (0.78 kg), dimethylacetamide (8.3 L) and potassium carbonate (0.59 kg) were charged in a reactor, and the reaction mixture was heated at about 100-105° C. for about 5 hours. The reaction mixture was then cooled to 10-20° C., quenched with deionized water, and filtered. The filter cake was washed with deionized water and dried at a temperature not more than 40° C. under vacuum. The title compound was obtained in a yield of 90% (1.3 kg).

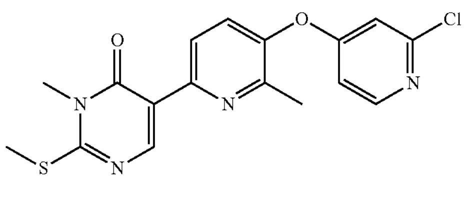 [SMILES: CSc1ncc(-c2ccc(Oc3ccnc(Cl)c3)c(C)n2)c(=O)n1C]

5-(5-((2-chloropyridin-4-yl)oxy)-6-methylpyridin-2-yl)-3-methyl-2-(methylthio)pyrimidin-4(3H)-one: 3-((2-chloropyridin-4-yl)oxy)-6-iodo-2-methylpyridine (1.00 kg), (1-methyl-2-(methylthio)-6-oxo-1,6-dihydropyrimidin-5-yl)boronic acid (0.64 kg), palladium-tetrakis(triphenylphosphine) (0.10 kg) and dioxane (15.3 L) were charged in a reactor, and the mixture was de-gassed by sparging nitrogen. In a separate vessel, a solution of sodium carbonate (0.92 kg) in deionized water (3.1 L) was prepared. The sodium carbonate solution was transferred to the reactor, and the mixture was de-gassed by sparging nitrogen. The resulting reaction mixture was heated at reflux for about 3 hours, cooled to 15-25° C. and quenched with deionized water and filtered. The filter cake was washed with deionized water. A suspension of the wet solid in deionized water was heated to 35-45° C., cooled to 15-25° C., then filtered again, washed with deionized water and dried under vacuum at a temperature of not more than 50° C. The resulting solid was taken up in methyl-tert-butyl ether (10.1 L). The mixture was stirred at 45-55° C., cooled to 15-25° C., and filtered. The filter cake was washed with methyl-tert-butyl ether and dried at a temperature not more than 40° C. under vacuum. The title compound was obtained in a yield of 82% (0.89 kg).

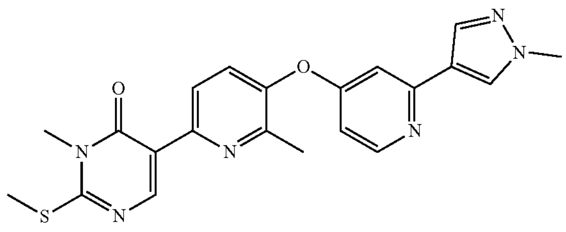

3-methyl-5-(6-methyl-5-((2-(1-methyl-1H-pyrazol-4-yl)pyridin-4-yl)oxy)pyridin-2-yl)-2-(methylthio)pyrimidin-4(3H)-one: 5-(5-((2-chloropyridin-4-yl)oxy)-6-methylpyridin-2-yl)-3-methyl-2-(methylthio)pyrimidin-4(3H)-one (1.00 kg), 1-methyl-4-(4,4,5,5-tetramethyl-1,3,2-dioxaborolan-2-yl)-1H-pyrazole (0.83 kg), palladium-tetrakis(triphenyl phosphine) (0.11 kg), and dioxane (12.0 L) were charged to a reactor, and the mixture was de-gassed by sparging nitrogen. Then, a potassium carbonate solution (1.48 kg) in deionized water (4.0 L) was added to the reactor, and the mixture was de-gassed by sparging nitrogen. The mixture was heated to reflux for about 15 hours, then cooled to 15-25° C., quenched with deionized water and stirred. The precipitated solid was filtered, washed with deionized water, and partially dried on filter. The solid was then charged in a vessel, together with deionized water and heated at 35-45° C., then cooled to 15-25° C., filtered, washed with deionized water, and dried with vacuum at a jacket temperature of not more than 40° C. The solid was re-charged in a vessel in isopropyl alcohol (5.0 L) and acetone (2.5 L) and was heated to 65-75° C., then cooled and stirred at 5-15° C., filtered, and washed with isopropyl alcohol. The wet solid was re-charged in the vessel with isopropyl alcohol (5.0 L) and acetone (2.5 L). The mixture was then heated at 65-75° C., then cooled and stirred at 5-15° C., filtered, and washed with isopropyl alcohol. The solid was dried under vacuum at a temperature lower than, or equal to, 40° C. The title compound was obtained in a yield of 66% (0.74 kg).

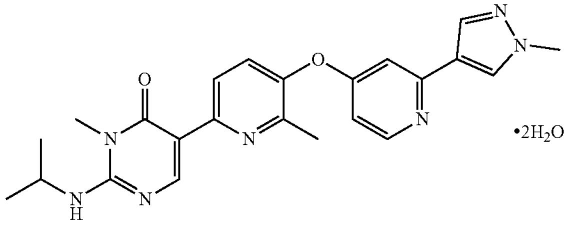 [SMILES: Cc1nc(-c2cnc(NC(C)C)n(C)c2=O)ccc1Oc1ccnc(-c2cnn(C)c2)c1]

2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one dihydrate: 3-methyl-5-(6-methyl-5-((2-(1-methyl-1H-pyrazol-4-yl)pyridin-4-yl)oxy)pyridin-2-yl)-2-(methylthio)pyrimidin-4(3H)-one (1.00 kg), isopropylamine (8.1 L), and N-methylpyrrolidone (8.1 L) were charged in a reactor, heated to 105-115° C. for about 28 hours in a sealed environment. The reaction mixture was cooled to 20-30° C. Distillation was performed under vacuum with a jacket temperature of not more than 35° C. until no more distillate was collected, then the temperature was adjusted to 15-25° C. Deionized water was added and the mixture was stirred at 15-25° C. The solid was isolated by filtration, washed with deionized water, and dried at a jacket temperature of not more than 40° C. The dried product and methyl-tert-butyl ether were stirred and then filtered and the solid was washed with methyl-tert-butyl ether. The solid was then charged in a reactor, together with dichloromethane and methanol and the mixture was stirred to obtain a clear solution. 3-Mercaptopropyl ethyl sulfide Silica was charged in the reactor and the reactor contents were stirred for about 17.5 hours. The mixture was filtered, followed by a rinse with dichloromethane, and the treatment was repeated with a fresh portion of 3-mercaptopropyl ethyl sulfide Silica. The filtered content was distilled under vacuum until minimum volume, and the distillation was repeated with a continuous addition of acetone while maintaining the volume. The resulting residue was diluted with a mixture of acetone and water and stirred and heated to 50° C., followed by cooling. The solid was isolated by filtration and washed with a mixture of acetone and water. The resuspension in acetone and water was repeated, and the resulting solid was dried under vacuum with heat. The solid was dispensed into a vessel. DMAc (dimethylacetamide) and water were charged to the vessel to give 5 volumes of DMAc-$H_2O$ (4.25 volumes DMAc and 0.75 volumes $H_2O$) ratio. The system was stirred to give complete suspension of material and heated to about 80° C. to access clear solution. The system was then cooled to about 65° C. and held for about 15 minutes. Milled seed material of the title compound (about 5 wt. %) was charged to the vessel. The system was held for 15-60 minutes. Water (2 volumes) was charged to the vessel at 65° C. over about 4 hours (0.5 volumes/hour). The system was allowed to cool to about 25° C. at about 0.1° C./min over about 6.5 hours before the mixture was stirred at room temperature for about 5 hours. The solid precipitate was isolated via filtration, washed with water (about 10 volumes then about 5 volumes) and dried under vacuum at a temperature no higher than 40° C. until moisture content by Karl Fischer analysis (KF) was no more than about 8% and no less than about 6%. The title compound was obtained in a yield of 70% (0.78 kg). At least the procedure in Example 1 provides the means for preparing the compound of Formula (I).

FIGS. 1-4 show UHPLC chromatograms of exemplary batches of a dihydrate of the compound of Formula (I) which were prepared according to Example 1. Representative UHPLC conditions: Column Acquity UPLC CSH C18, 1.7 μm, 2.1 mm×100 mm, or equivalent. Mobile Phase (MP) A: 10.5 mM Ammonium Formate pH 3.5. MP B: acetonitrile.

Table 1 shows a retention time profile of an exemplary batch of a dihydrate of the compound of Formula (I) as prepared according to Example 1 and as shown in FIG. 1.

TABLE 1

| Peak | Formula | Approximate RT (min) | Approximate RRT | RRF | Acceptance Criteria % w/w to % area |
|---|---|---|---|---|---|
| 2 | VII | 12.64 | 0.91 | 1.007 | 0.15% to ≈0.15% |
| 3 | VIII | 12.82 | 0.92 | 0.822 | 0.15% to ≈0.12% |
| 1 | I | 13.90 | 1.00 | 1.000 | — |
| 4 | IX | 14.42 | 1.04 | 0.854 | 0.15% to ≈0.13% |
| 5 | VI | 14.91 | 1.07 | 0.679 | 0.30% to ≈0.20% |
| 6 | V | 15.63 | 1.12 | 0.967 | 0.30% to ≈0.29% |
| 7 | IV | 17.24 | 1.24 | 0.983 | 0.15% to ≈0.15% |
| 8 | III | 20.99 | 1.51 | 0.835 | 0.30% to ≈0.25% |

RT = retention time (RT); RRT = relative retention time; RRF = relative response factor.

Figure 2:
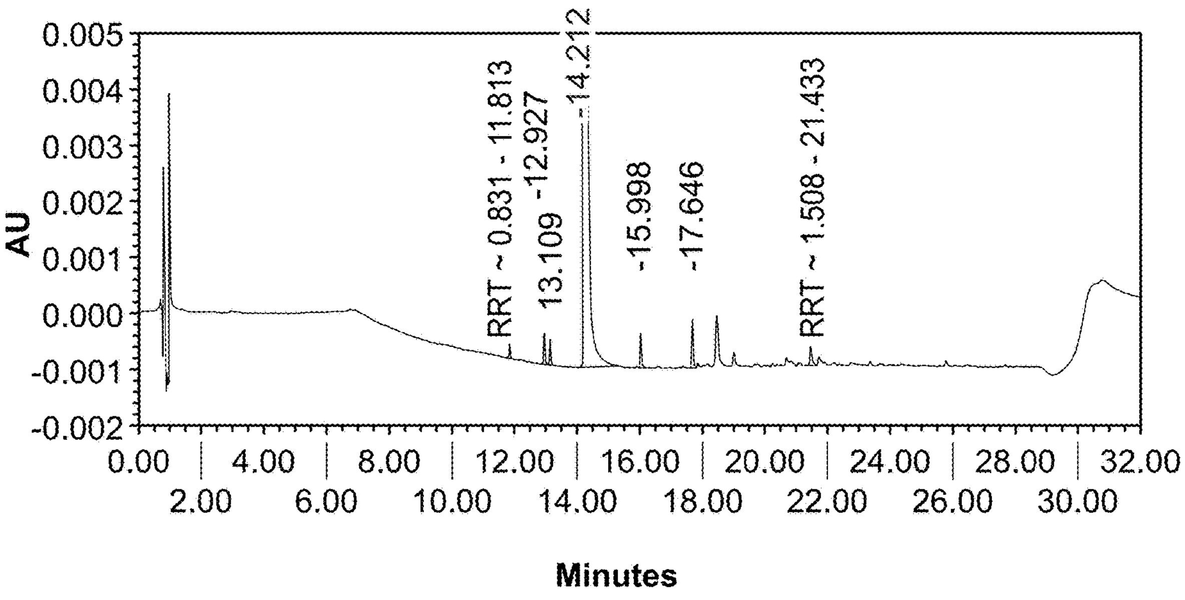
FIG. 2 shows an UHPLC chromatogram of exemplary batch 1a of a dihydrate of the compound of Formula (I).
Figure 3:
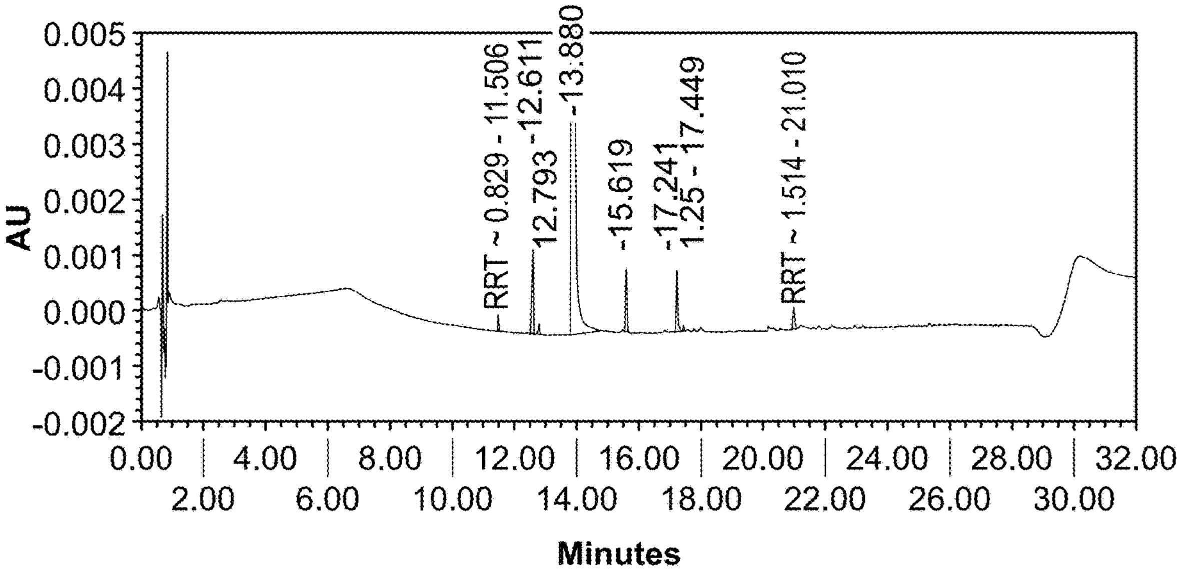
FIG. 3 shows an UHPLC chromatogram of exemplary batch 1b of a dihydrate of the compound of Formula (I).
Figure 4:
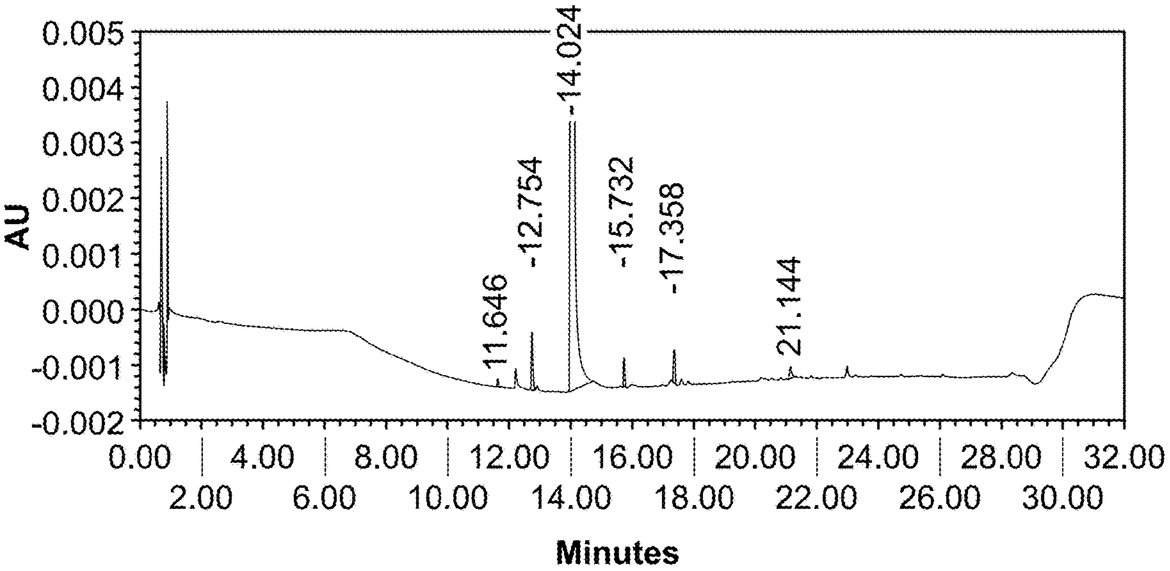
FIG. 4 shows an UHPLC chromatogram of exemplary batch 1c of a dihydrate of the compound of Formula (I).

Table 2 shows purity profiles using the above-described UHPLC method of additional exemplary batches of a dihydrate of the compound of Formula (I) as prepared according to Example 1 and as shown in FIGS. 2-4.

TABLE 2

| | Batches | | |
|---|---|---|---|
| Impurity | 1a (area %) | 1b (area %) | 1c (area %) |
| III | 0.07 | 0.07 | 0.05 |
| IV | 0.14 | 0.16 | 0.08 |
| V | 0.10 | 0.14 | 0.07 |
| VI | <0.05 | <0.05 | <0.05 |
| VII | 0.11 | 0.09 | 0.11 |
| VIII | 0.05 | <0.05 | <0.05 |
| IX | <0.05 | <0.05 | <0.05 |

Table 2a shows purity profiles using the above-described UHPLC method of additional exemplary batches of a dihydrate of the compound of Formula (I) as prepared according to Example 1 and as shown in FIGS. 2-4.

TABLE 2a

| | Batches | | |
|---|---|---|---|
| Impurity | 1a (AUC) | 1b (AUC) | 1c (AUC) |
| III | 0.07 | 0.07 | 0.05 |
| IV | 0.14 | 0.16 | 0.08 |
| V | 0.10 | 0.14 | 0.07 |
| VI | <0.05 | <0.05 | <0.05 |
| VII | 0.11 | 0.09 | 0.11 |
| VIII | 0.05 | <0.05 | <0.05 |
| IX | <0.05 | <0.05 | <0.05 |

Table 3 shows purity profiles of the compound of Formula (II) reported in ppm for exemplary batches of a dihydrate of the compound of Formula (I) as prepared according to Example 1 using the above-described UHPLC method.

TABLE 3

| | Batches | | |
|---|---|---|---|
| Impurity | 1a (ppm) | 1b (ppm) | 1c (ppm) |
| II | <30 | <30 | <30 |

EQUIVALENTS

Those skilled in the art will recognize or be able to ascertain using no more than routine experimentation, numerous equivalents to the specific embodiments described specifically in this disclosure. Such equivalents are intended to be encompassed in the scope of the following claims.

We claim:

1. A pharmaceutically acceptable oral dosage form, comprising:

(i) a dihydrate form of a compound of Formula (I):

(I)

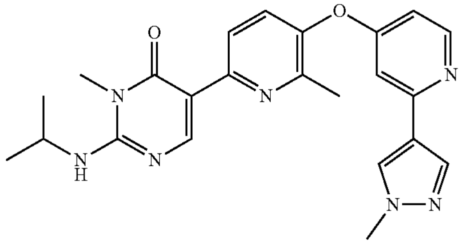

wherein the dihydrate form is present in the oral dosage form in an amount to provide a dose selected from the group consisting of 2 mg, 10 mg, 14 mg, 20 mg, and 30 mg of the compound;

(ii) about 10 ppm to about 500 ppm of a compound of Formula (II):

(II)

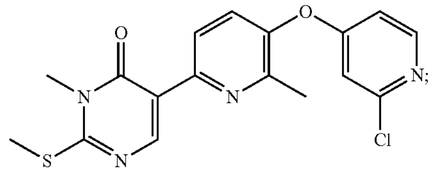

and (iii) a pharmaceutically acceptable excipient.

2. The oral dosage form of claim 1, about 150 ppm to about 400 ppm of the compound of Formula (II) is present in the oral dosage form.

3. The oral dosage form of claim 1, wherein no more than about 50 ppm of the compound of Formula (II) is present in the oral dosage form.

4. The oral dosage form of claim 1, wherein no more than about 150 ppm of the compound of Formula (II) is present in the oral dosage form.

5. The oral dosage form of claim 1, wherein no more than about 300 ppm of the compound of Formula (II) is present in the oral dosage form.

6. The oral dosage form of claim 1, wherein no more than about 330 ppm of the compound of Formula (II) is present in the oral dosage form.

7. The oral dosage form of claim 1, wherein no more than about 700 ppm of the compound of Formula (II) is present in the oral dosage form.

8. The oral dosage form of claim 1, wherein the dihydrate form is present in the pharmaceutical composition in an amount to provide 14 mg of the compound.

9. The oral dosage form of claim 1, wherein the dihydrate form is present in the pharmaceutical composition in an amount to provide 20 mg of the compound.

10. The oral dosage form of claim 1, wherein the dihydrate form is present in the pharmaceutical composition in an amount to provide 30 mg of the compound.

11. The oral dosage form of claim 1, wherein the oral dosage form is a capsule.

12. A pharmaceutical composition, comprising:

(i) a compound of Formula (I):

(I)

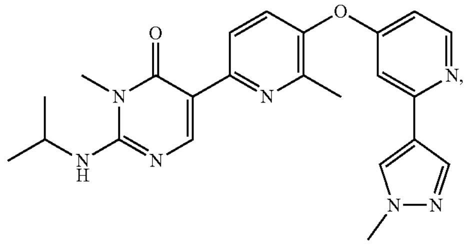

or a hydrate thereof, wherein the compound or hydrate thereof is present in the pharmaceutical composition in an amount to provide a dose selected from the group consisting of 2 mg, 10 mg, 14 mg, 20 mg, and 30 mg of the compound; and (ii) a compound of Formula (II):

(II)

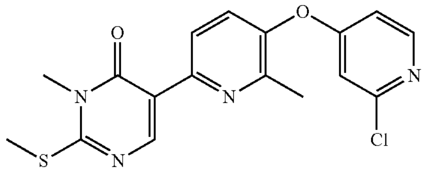

wherein the compound of Formula (II) is present in the pharmaceutical composition, in an amount less than about 800 ppm; and (iii) a pharmaceutically acceptable excipient.

13. The pharmaceutical composition of claim 12, wherein less than about 50 ppm of the compound of Formula (II) is present in the pharmaceutical composition.

14. The pharmaceutical composition of claim 12, wherein less than about 150 ppm of the compound of Formula (II) is present in the pharmaceutical composition.

15. The pharmaceutical composition of claim 12, wherein less than about 300 ppm of the compound of Formula (II) is present in the pharmaceutical composition.

16. The pharmaceutical composition of claim 12, wherein less than about 330 ppm of the compound of Formula (II) is present in the pharmaceutical composition.

17. The pharmaceutical composition of claim 12, wherein less than about 500 ppm of the compound of Formula (II) is present in the pharmaceutical composition.

18. The pharmaceutical composition of claim 12, wherein less than about 700 ppm of the compound of Formula (II) is present in the pharmaceutical composition.

19. The pharmaceutical composition of claim 12, comprising a dihydrate form of the compound in an amount to provide 14 mg of the compound.

20. The pharmaceutical composition of claim 12, comprising a dihydrate form of the compound in an amount to provide 20 mg of the compound.

21. The pharmaceutical composition of claim 12, comprising a dihydrate form of the compound in an amount to provide 30 mg of the compound.

* * * * *